US008236312B2

(12) United States Patent
Park et al.

(10) Patent No.: US 8,236,312 B2
(45) Date of Patent: Aug. 7, 2012

(54) VEGF-SPECIFIC HUMAN ANTIBODY

(75) Inventors: Young Woo Park, Daejeon (KR);
So-Young Choi, Daejeon (KR);
Eun-Jung Song, Daejeon (KR); Jung Yu, Daejeon (KR); Myung-Ho Sohn, Daejeon (KR); Jae Won Jeon, Daejeon (KR); Joon-Goo Jung, Daejeon (KR); Myeoung Hee Jang, Daejeon (KR); Sungsub Kim, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 187 days.

(21) Appl. No.: 12/580,959

(22) Filed: Oct. 16, 2009

(65) Prior Publication Data
US 2010/0129373 A1 May 27, 2010

(30) Foreign Application Priority Data
Nov. 26, 2008 (KR) ........................ 10-2008-0118124

(51) Int. Cl.
*A61K 39/395* (2006.01)
*C07K 16/22* (2006.01)
*C12N 15/13* (2006.01)
(52) U.S. Cl. ................ 424/142.1; 424/145.1; 435/69.1; 530/388.15; 530/388.24
(58) Field of Classification Search .................. None
See application file for complete search history.

(56) References Cited

U.S. PATENT DOCUMENTS 5,659,013 A * 8/1997 Senger et al. .................. 530/350
7,169,901 B2 1/2007 Baca et al.
2005/0215769 A1* 9/2005 Breece et al. ............ 530/388.22

FOREIGN PATENT DOCUMENTS
KR 10-2002-0019905 3/2002

OTHER PUBLICATIONS

Afanasieva et al., "Single-chain antibody and its derivatives directed against vascular endothelial growth factor: application for antiangiogenic gene therapy," *Gene Therapy*, 10(21):1850-1859, Oct. 2003.

Borgstrom et al., "Complete inhibition of angiogenesis and growth of microtumors by anti-vascular endothelial growth factor neutralizing antibody: novel concepts of angiostatic therapy from intravital videomicroscopy," *Cancer Res.*, 56:4032-4039, Sep. 1996.
Fan et al., "Expression and function of vascular endothelial growth factor receptor-1 on human colorectal cancer," *Oncogene*, 24:2647-2653, Apr. 2005.
Fuh et al., "Structure-function studies of two synthetic anti-vascular endothelial growth factor Fabs and comparison with the Avastin Fab," *Journal of Biological Chemistry*, 281(10):6625-6631, Dec. 22, 2005.
Kim et al., "Inhibition of vascular endothelial growth factor-induced angiogenesis suppresses tumour growth in vivo," *Nature*, 362:841-844, Mar. 8, 1993.
Liang et al., "Cross-species vascular endothelial growth factor (VEGF)-blocking antibodies completely inhibit the growth of human tumor xenografts and measure the contribution of stromal VEGF," *Journal of Biological Chemistry*, 281(2):951-961, Nov. 7, 2005.
Soker et al., "VEGF165 mediates formation of complexes containing VEGFR-2 and neuropilin-1 that enhance VEGF165-receptor binding," *J. Cell Biochem*, 85:357-368, 2002.
Sowter et al., "Expression and localization of the vascular endothelial growth factor family in ovarian epithelial tumors," *Lab Invest.*, 77:607-614, Dec. 1997.
Tomisawa et al., "Expression pattern of vascular endothelial growth factor isoform is closely correlated with tumour stage and vascularisation in renal cell carcinoma," *Eur J Cancer*, 35:133-137, Jan. 1999.
Volm et al., "Prognostic value of vascular endothelial growth factor and its receptor Flt-1 in squamous cell lung cancer," *Cancer*, 74:64-68, Feb. 1997.
Wey et al., "Vascular endothelial growth factor receptor-1 promotes migration and invasion in pancreatic carcinoma cell lines," *Cancer*, 104:427-438, Jul. 2005.
Yoshiji et al., "Expression of vascular endothelial growth factor, its receptor, and other angiogenic factors in human breast cancer," *Cancer Res.*, 56:2013-2016, May 1996.

* cited by examiner

*Primary Examiner* — Christine J Saoud
(74) *Attorney, Agent, or Firm* — Klarquist Sparkman, LLP

(57) ABSTRACT

The present invention relates to a vascular endothelial growth factor (VEGF)-specific human antibody, and more particularly to a human antibody including a complementarity determining region (CDR) and a framework region (FR) derived from a human antibody specifically bound to VEGF. The VEGF-specific human antibody of the present invention may be used in diagnosis of diseases caused by the VEGF-overexpression, classification of the diseases, visualization, treatment, and prognostic evaluation.

15 Claims, 16 Drawing Sheets

1. CD24(20ng)
2. pYK602-VEGF 1st
3. pYK602-VEGF 2nd
4. pYK602-His-VEGF 1st
5. pYK602-His-VEGF 2nd
6. pYK603-VEGF 1st
7. pYK603-VEGF 2nd

1. BSA 0.5 μg
2. BSA 1 μg
3. pYK602-His-VEGF 0.5 μg
4. pYK602-His-VEGF 1 μg

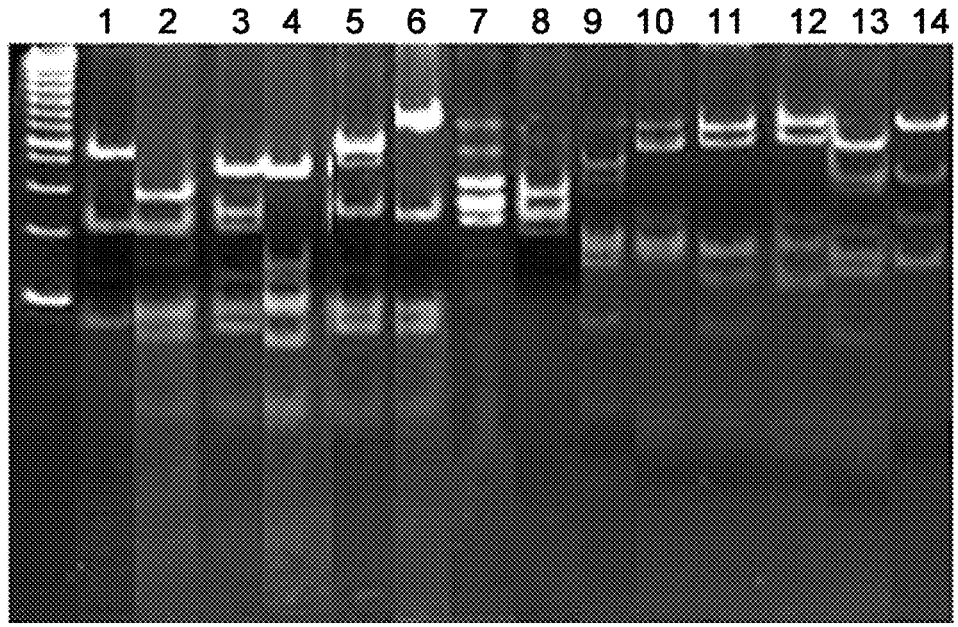

*Heavy Chain*

|  |  | ~~~~~~~~~~~~ FR 1 ~~~~~~~~~~~~ | - CDR1 - | ~~~ FR 2 ~~~ |
|---|---|---|---|---|
| VEGF- A4 | (1) | MA QMQLVESGGGVVQPGGSLRLSCAASGFIFN | D-YAMH | WVRQAPGKGLE |
| VEGF-B12 | (1) | MA QVQLVQSGAEVKKPGSSVKVSCKASGGTFS | S-YAIS | WVRQAPGQGLE |
| VEGF-C11 | (1) | MA QMQLVQSGAEVKKPGSSVKVSCKASGGTFS | S-DAIS | WVRQAPGQGLE |
| VEGF-C12 | (1) | MA QMQLVESGGGLVKPGGSLRLSCAASGFSFS | S-YGMN | WVRQAPGKGLE |
| VEGF- C5 | (1) | MA QVQLVESGGGVVQPGRSLRLSCAASGFTFT | S-YSMH | WVRQAPGKGLE |
| VEGF- C9 | (1) | MA QVQLVKSEGGVVQPGRSLRLSCAASGFTFS | S-YAMH | WVRQAPGKGLE |
| VEGF-D12 | (1) | MA QMQLVESGGGVVQPGGSLRLSCAASGFSFD | E-YAMH | WVRQAPGKGLE |
| VEGF- E9 | (1) | MA QVTLRESGPTMVKPTQTLTLTCTFSGFSLS | TSGVAVG | WIRQPPGQALE |
| VEGF- F2 | (1) | MA QVQLVESGGGLVQPGGSLRLSCAASGFSFN | S-YAMS | WIRQAPGKGLE |
| VEGF- F6 | (1) | MA QVTLRESGPTMVKPTQTLTLTCTFSGFSLS | TSGVAVG | WIRQPPGQALE |
| VEGF- F9 | (1) | MA QVQLVKSGAEVKKPGSSVKVSCKASGGTFR | T-TAIT | WVRQAPGQALE |
| VEGF-G12 | (1) | MA QVQLVQSGAEVKKPGSSVKVSCTAAGGTFN | N-YAIS | WLRQAPGQGLE |
| VEGF- G9 | (1) | MA QVQLVESGGGVVQPGRSLTLSCAASGFTFS | T-YALH | WVRQAPGKGLE |
| VEGF- H7 | (1) | MA QMQLVKSGGGVVQPGRSLRLSCAASGFTFS | K-YGMH | WVRQAPGKGLE |

Fig. 7b

```
              ---  ----- CDR 2 ----- -------------- FR 3 -----------
VEGF- A4  (49)  WVS  FINEDGGNIYYGDSVKG  RFTISRDNSKNSLYLQMNSLRAEDTAVYYCAR
VEGF-B12  (49)  WMG  GIIPIFGTANYAQKFQG  RVTITADESTSTAYMELSSLRSEDTAVYYCAR
VEGF-C11  (49)  WMG  GVIPIFATTTYAQGFQG  RLTITADTSTRTAYMELTNLRSEDTAVYYCAR
VEGF-C12  (49)  WVS  SISSSSSSIHYADSVKG  RFSISRDNAKNSVYLQMNSLRAEDTAVYYCAR
VEGF- C5  (49)  WVA  GISYDGSSKQFGDSVKG  RFTISRDNSKSTLYLQMNSLRAEDTAVYYCAK
VEGF- C9  (49)  WVA  VISYDGSNKYYADSVKG  RFTISRDNSKNTLYLQMNSLRAEDTAVYYCAK
VEGF-D12  (49)  WVS  LISGDDYNTFYADSVKG  RFTISRDNSKNSLYLQMNSLRAEDTAVYYCAK
VEGF- E9  (51)  WLA  LIYWDN-DKRYSPSLKN  RLTVAKDTSKSQVVLTMTNMDPMDTATYYCAH
VEGF- F2  (49)  WVS  YISSSGHDIYYADPVKG  RFTISRDNAKNSLYLQMNSLRAEDTAVYYCVR
VEGF- F6  (51)  WLA  LIYWDN-DKRYSPSLKN  RLTVAKDTSKSQVVLTMTNMDPMDTATYYCAH
VEGF- F9  (49)  WVG  WITPFNGNTFYAQKFQD  RVTITRDRSMSTAYMELSSLRSEDTAVYYCAK
VEGF-G12  (49)  WMG  RIIPIYGTPTYAQKFRD  RVTITADESTSTAYMELSNLRSEDTAVYYCAR
VEGF- G9  (49)  WVA  VISHDGTTDYYRDSVKG  RFTISRDNSKNTLYLQMNSLRAEDTAVYYCSR
VEGF- H7  (49)  WLA  FIWFDGSNKFYADSVKG  RFTVSRDNSKNTLFLQMNSLRAEDTAVYYCAK
```

Fig. 7c

```
              ----CDR 3 ----    --- FR 4---   -------- Linker---
VEGF- A4  (99)   EPSGSLT----FDY   WGQGTLVTVSS  GLGGLGGGSGGGGSGGS (SEQ ID No. 44)
VEGF-B12  (99)   DRSG-YTA---MDY   WGQGTLVTVSS  GLGGLGGGSGGGGSGGS (SEQ ID No. 45)
VEGF-C11  (99)   GQMDRGGG---LDP   WGQGTLVTVSS  GLGGLGGGSGGGGSGGS (SEQ ID No. 46)
VEGF-C12  (99)   LGPYD------AFDF  WGQGTVVTVSS  GLGGLGGGSGGGGSGGS (SEQ ID No. 47)
VEGF- C5  (99)   DGVPGHSYGIGMDV   WGQGTTVIVSS  GLGGLGGGSGGGGSGGS (SEQ ID No. 48)
VEGF- C9  (99)   DVDSWSQG-WFPH    WGQGTLVTVSS  GLGGLGGGSGGGGSGGS (SEQ ID No. 49)
VEGF-D12  (99)   DAGPAGGG-GLDH    WGQGTLVTVSS  GLGGLGGGSGGGGSGGS (SEQ ID No. 50)
VEGF- E9  (100)  GDG-------WLFDF  WGQGTLVTVSS  GLGGLGGGSGGGGSGGS (SEQ ID No. 51)
VEGF- F2  (99)   DKLATPG---AFDI   WGQGTMVTVSS  GLGGLGGGSGGGGSGGS (SEQ ID No. 52)
VEGF- F6  (100)  GDG-------WLFDF  WGQGTLVTVSS  GLGGLGGGSGGGGSGGS (SEQ ID No. 51)
VEGF- F9  (99)   SQAAELGT-GAFDI   WGQGTLVTVSS  GLGGLGGGSGGGGSGGS (SEQ ID No. 53)
VEGF-G12  (99)   ERS----FW-NWFAP  WGQGTLITVSS  GLGGLGGGSGGGGSGGS (SEQ ID No. 54)
VEGF- G9  (99)   DGSG------YFFDY  WGPGTQVTVSS  GLGGLGGGSGGGGSGGS (SEQ ID No. 55)
VEGF- H7  (99)   DRDYYGSG-PLDY    WGQGTQITVSS  GLGGLGGGSGGGGSGGS (SEQ ID No. 56)
```

Fig. 8a

*Light Chain*

|  |  |  | ---------- FR 1 ---------- | ---- CDR 1 ---- | --- FR 2- |
|---|---|---|---|---|---|
| VEGF-A4 | (145) | GVGS | DIQMTQSPSSLPASVGDTVTISC | RAS---QTISSYLN | WYQQKPGKAP |
| VEGF-B12 | (145) | GVGS | DIQMTQSPSSLSASVGDRVTITC | RAS---QGISSYLA | WYQQKPGKAP |
| VEGF-C11 | (146) | GVGS | DIQMTQSPSSLSASVGDRVTITC | RAS---QGIGNYLN | WYQQKPGKAP |
| VEGF-C12 | (144) | GVGS | QLVLTQ-PPSVSGTPGQRVTISC | PGG-TSNIDSKYVH | WYQQLPGTAP |
| VEGF-C5 | (149) | GVGS | DIQMTQSPSSVSASVGDRVTITC | RAS---QGISSWLA | WYQQKPGKAP |
| VEGF-C9 | (147) | GVGS | DIQMTQSPSSLSASVGDRVTITC | RAS---QTISTFVN | WYQQKPGKAP |
| VEGF-D12 | (147) | GVGS | DIQMTQSPSSLSASVGDRVTITC | RTS---QTITNFLN | WYQQKPGKAP |
| VEGF-E9 | (144) | GVGS | QLVLTQ-PPSVSGAPGQRVTISC | TGSNSNIGAGHDVH | WYQQLPGAAP |
| VEGF-F2 | (146) | GVGS | DIQMTQSPSSLSASVGDRVSITC | RAS---QSISNWLA | WYQQKPGKAP |
| VEGF-F6 | (144) | GVGS | QLVLTQ-PPSVSGAPGQRVTISC | TGSNSNIGAGHDVH | WYQQLPGAAP |
| VEGF-F9 | (148) | GVGS | QLVLTQ-PSSVSGTPGQRVTISC | SGSYSNIGTNY-VY | WYHQLPGTAP |
| VEGF-G12 | (145) | GVGS | QLVLTQ-PPSVSGAPGQRVIISC | TGSSSNIGAGYDVH | WYQQLPGTAP |
| VEGF-G9 | (144) | GVGS | NFMLTQ-PASVSGSPRQSITISC | TGSSDVGGYNYVS | WYQQHPGKAP |
| VEGF-H7 | (147) | GVGS | DIQMTQSPSSLSASVGDRVTITC | RAS---QRIATYLH | WYQQKPGKAP |

Fig. 8b

|  |  | -----CDR 2- | ------------- FR 3 ------------- | -- CDR 3 |
|---|---|---|---|---|
| VEGF-A4 | (192) | KLLIY AASRLQS | GVPSRFSGSGSGTDFTLTISSLQPEDFATYYC | QQSYS--- |
| VEGF-B12 | (192) | KLLIY AASTLQS | GVPSRFSGSGSGSHFTLTITNLQPEDFATYYC | QQGHT--- |
| VEGF-C11 | (193) | KLLVY AASSLQR | GVPSRFSGRGSGTDFTLTISGLPDDFALYYC | QQSYT-TP |
| VEGF-C12 | (192) | KLLIY RNDQRPS | GVPDRFSGSKSGTSASLAITGLQAADEAAYYC | QSYDTSLS |
| VEGF-C5 | (196) | KLLIY AASILQT | GVPSRFSGSGSGTDFTLTISSLQSDDFATYYC | QQANS-FP |
| VEGF-C9 | (194) | KLLIY SASSLQS | GVPSRFSGSGSGTDFTLTINSLQPEDFATYYC | QQNYS--- |
| VEGF-D12 | (194) | KLLIY GASSLQS | GVPSRFGSGSGTDFTLTINSLQPEDFATYYC | QQSHG--- |
| VEGF-E9 | (193) | RVVIY GNTNRAS | GVPERFSGSKSATSASLAITGLQAEDEADYYC | QSYDN-SL |
| VEGF-F2 | (193) | KLLIY EASSLES | GVPSRFSGSGSGTDFTLTISSLQPEDFASYFC | QQSHG--- |
| VEGF-F6 | (193) | RVVIY GNTNRAS | GVPERFSGSKSATSASLAITGLQAEDEADYYC | QSYDN-SL |
| VEGF-F9 | (196) | KLVIQ KNTQRPS | GVSDRFSGSRSGTSASLAISGLRSEDEGNYFC | SAWDD-SL |
| VEGF-G12 | (194) | KLLIY GNNNRPS | GVPDRFSGSKSGTSASLAITGLQAEDEADYYC | QSYDS-RL |
| VEGF-G9 | (193) | QLIIY DVTKRPS | GVSNRFSGSKSGNSASLTISGLQAEDEADYYC | SSYSSS-- |
| VEGF-H7 | (194) | KLLIY AASSLQS | GVPSRFSGSGSGTDFTLTISSLQPEDFATYYC | QQSYS--- |

Fig. 8c

```
             ---- -- FR 4 ---   ---- Myc Tag ----
VEGF- A4  (239)   TPYT  FGQGTKVDIKR  GGASLVEFEQKLISEEDL    (SEQ ID No. 94)
VEGF-B12  (239)   TPYT  FGQGTKLEIKR  GGASLVEFEQKLISEEDL    (SEQ ID No. 95)
VEGF-C11  (240)   --YS  FGPGTKVEIKR  GGASLVEFEQKLISEEDL    (SEQ ID No. 96)
VEGF-C12  (242)   APYV  FGTGTKVTVLG  GGASLVEFEQKLISEEDL    (SEQ ID No. 97)
VEGF- C5  (243)   --YT  FGQGTKVEIKR  GGASLVEFEQKLISEEDL    (SEQ ID No. 98)
VEGF- C9  (241)   TPLT  FGGGTRLEIKR  GGASLVEFEQKLISEEDL    (SEQ ID No. 99)
VEGF-D12  (241)   TPYT  FGQGTKLEIKR  GGASLVEFEQKLISEEDL    (SEQ ID No. 100)
VEGF- E9  (242)   SGYV  FGTGTKVTVLG  GGASLVEFEQKLISEEDL    (SEQ ID No. 101)
VEGF- F2  (240)   TPYT  FGQGTKLEIKR  GGASLVEFEQKLISEEDL    (SEQ ID No. 102)
VEGF- F6  (242)   SGYV  FGTGTKVTVLG  GGASLVEFEQKLISEEDL    (SEQ ID No. 101)
VEGF- F9  (245)   SAVL  FGGGTKLTVLG  GGASLVEFEQKLISEEDL    (SEQ ID No. 103)
VEGF-G12  (243)   G-VV  FGGGTKLTVLG  GGASLVEFEQKLISEEDL    (SEQ ID No. 104)
VEGF- G9  (241)   TFYV  FGTGTKVTVLG  GGASLVEFEQKLISEEDL    (SEQ ID No. 105)
VEGF- H7  (241)   TPYT  FAQGTKVEIKR  GGASLVEFEQKLISEEDL    (SEQ ID No. 106)
```

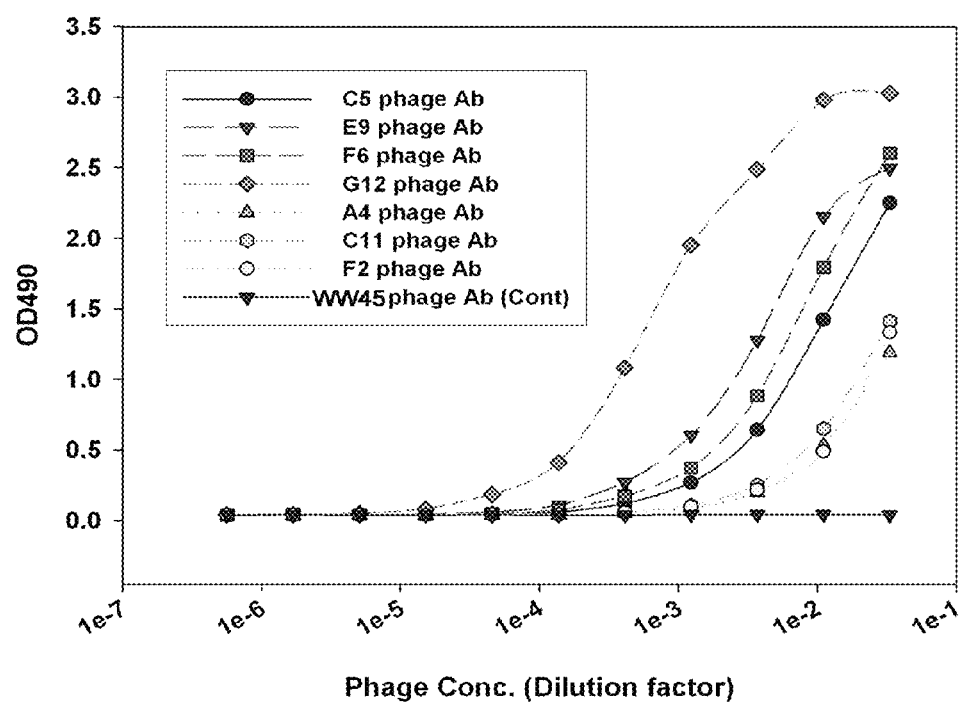

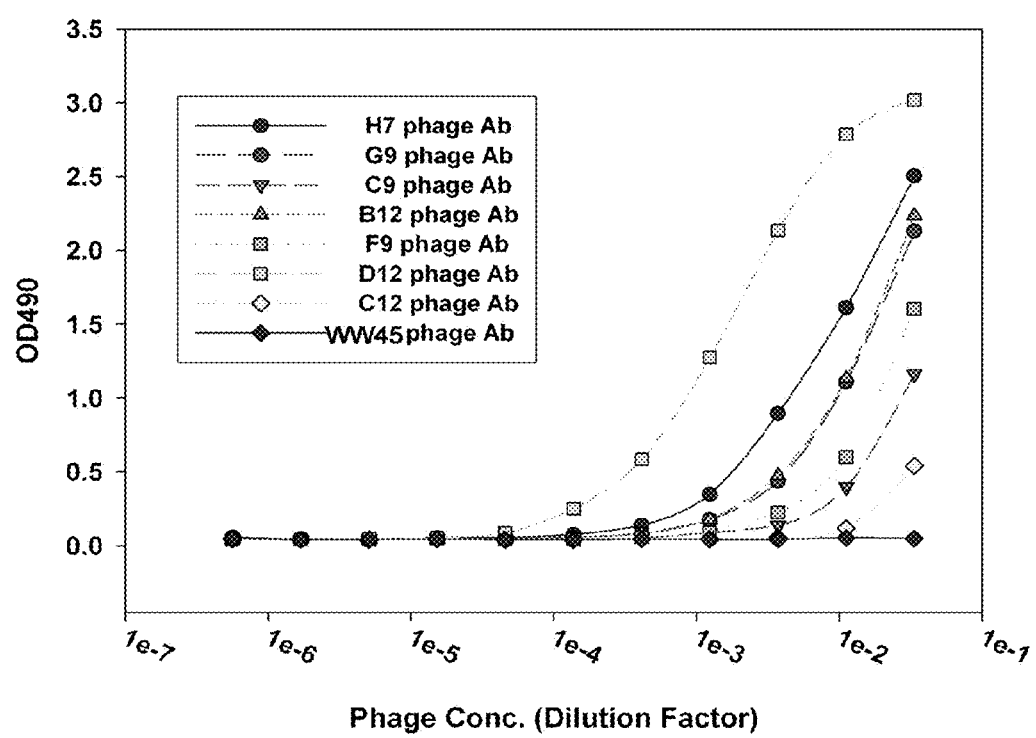

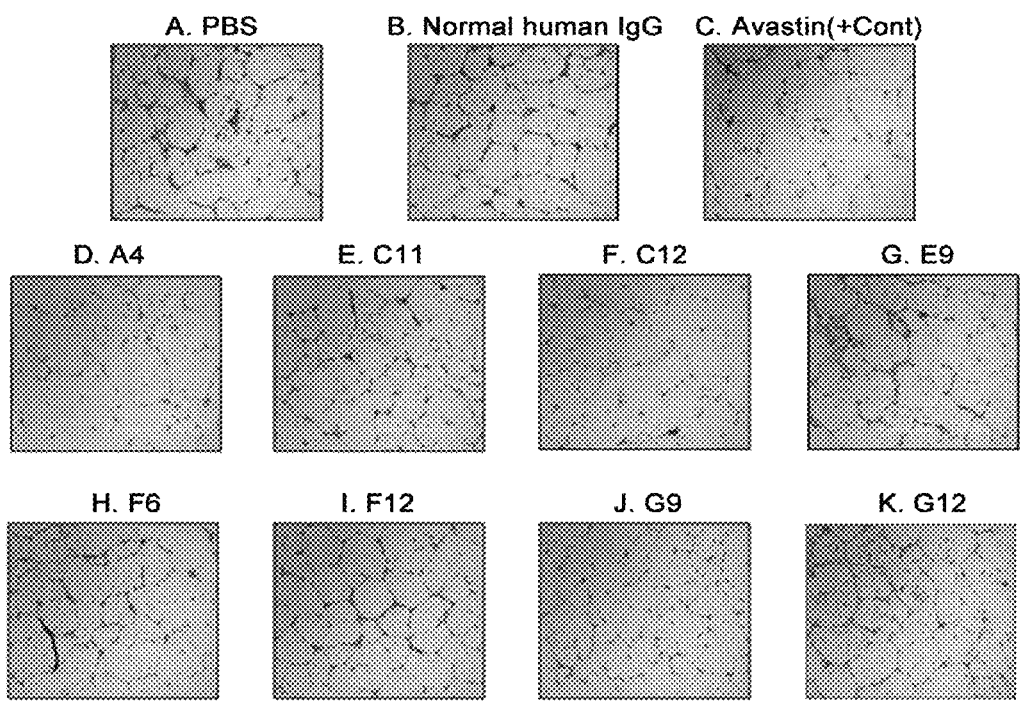

Fig. 11
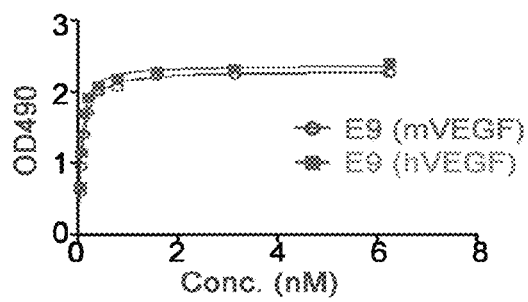
A. VEGF-E9 for mVEGF & hVEGF
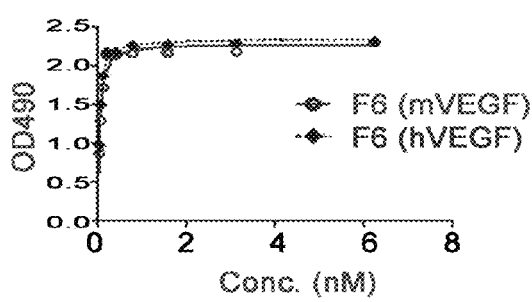
B. VEGF-F6 for mVEGF & hVEGF
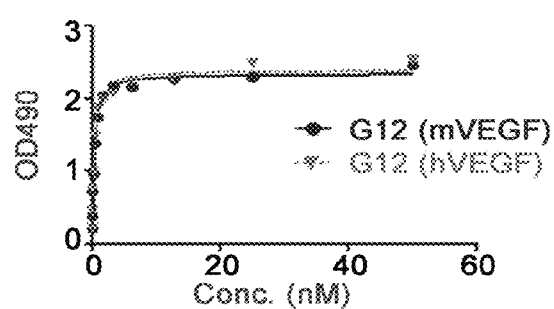
C. VEGF-G12 for mVEGF & hVEGF
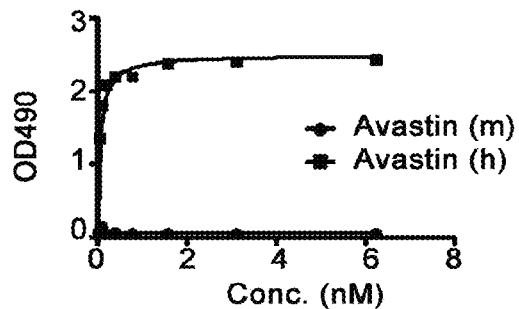
D. Avastin for mVEGF & hVEGF H chain vector

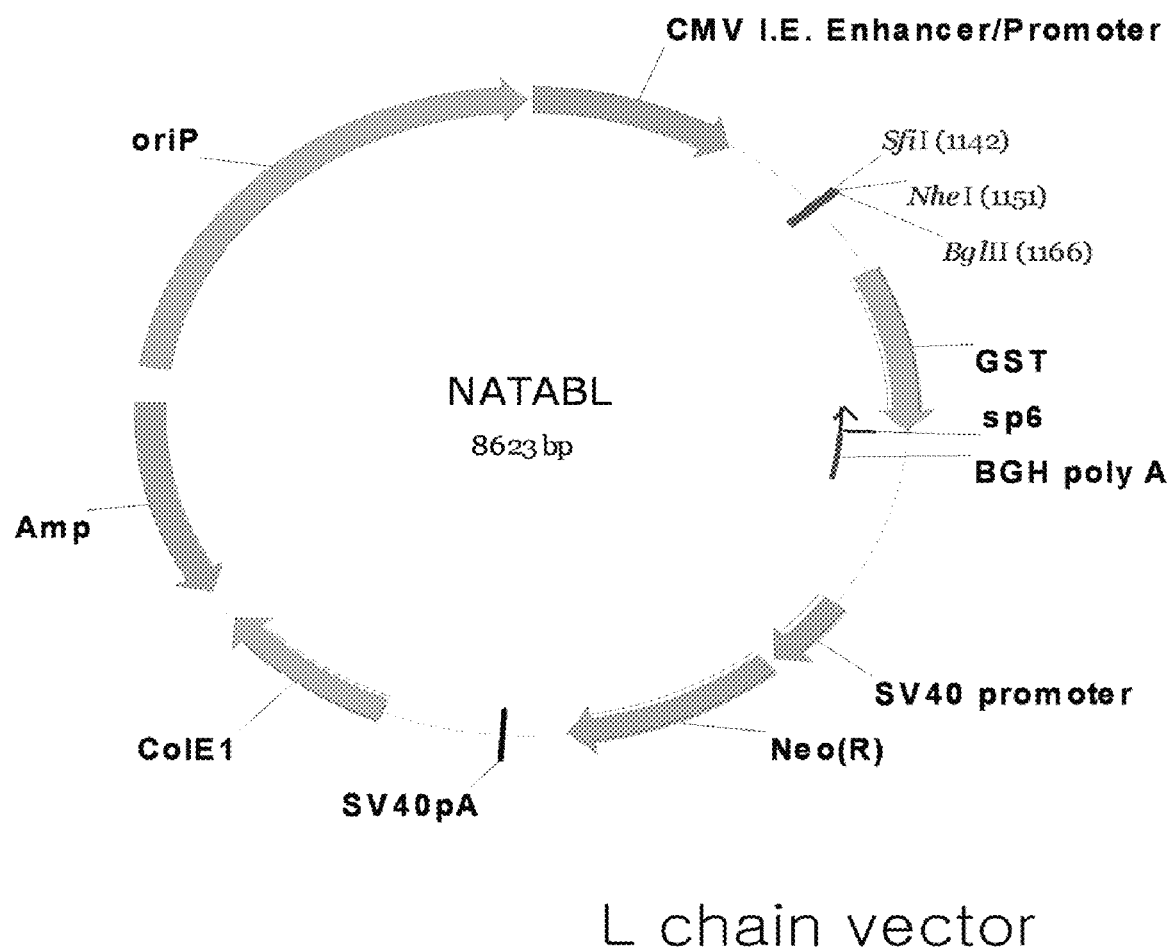

Fig. 16

```
Light chain
                     ----------- FR 1 ---------    ----- CDR 1-----        --- FR2-
VEGF-F06  (144)  GVGS QLVLTQ-PPSVSGAPGQRVTISC     TGSNSNIGAG--HDVH         WYQQLPGAAP
VEGF-2A09 (144)  GVGS QFVLTQ-PPSVSGAPGQKVTISC     TGSSSNIGAG--YDVH         WYQQVPGTAP
VEGF-2B05 (144)  GVGS QLVLTQ-PSSVSGAPGQRVTISC     TGGDSNIGAG--YDVH         WYQQLQGGAP
VEGF-2C11 (144)  GVGS DIVMTQTPLSSPVTPGESASISC     RSSQSLVRSDGTYYLS         WLQQRPGQPP
VEGF-2D10 (144)  GVGS QLVLTQ-PPSVSGAPGQCVTISC     TGSSSNLGAP--NDVH         WYQQRPGTAP
VEGF-2E11 (144)  GVGS QLVLTQ-PPSVSGAPGQKVTFSC     TGSSSNIGAG--YDVH         WYQSRPGTAP
VEGF-2F01 (144)  GVGS QLVLTQ-PPSVSGAPGQRVTISC     TGSSSNIGAP--NDVH         WYQQLPGYAP
VEGF-2G03 (144)  GVGS DIVMTQTPLSSPVTLGQPASISC     RSSQSLVRSDGTTYLS         WLQQRPGQPP
VEGF-2G04 (144)  GVGS QLVLTQ-PPSVSGAPGQRVTISC     TGSRSNPGAG--HDVH         WYQQLPGTAP
VEGF-2G12 (144)  GVGS QLVLTQ-PPSVSGAPGQRVTISC     TGSRSNIGAG--SDVH         WYQQLPGTAP
VEGF-2H07 (144)  GVGS QLVLTQ-PPSVSGAPGQRVTISC     TGSSYNIGAG--YDVH         WYQQLPGKAP
VEGF-2H08 (144)  GVGS QFVLTQ-PSSVSGAPGKTVTISC     SESSSNIGAG--PDVH         WYQSLPGYAP
VEGF-2H09 (144)  GVGS DIQMTQ-PSFVSAAVGDRVTINC     RASQGIVS-----WLA         WYQQKPGKAP
VEGF-G12  (145)  GVGS QLVLTQPPS-VSGAPGQRVIISC     TGSSSNIGAG--YDVH         WYQQLPGTAP
VEGF-2C05 (145)  GVGS QAVVTQEPS-LTVSPGGTVTLTC     GSSAGAVTSG--NYPF         WFQKKPGQAP
VEGF-2F09 (145)  GVGS QFVLTQPPS-VSGAPGQRVTISC     TGSSSNLGAG--YDVH         WYQSLPGTAP
VEGF-2F10 (145)  GVGS DIQMTQSPSSLYAAVGDRVTITC     RASQ-PISN----WLA         WYQKKPEQAP ----- - CDR2-    --------------- FR 3 ----------      --CDR 3-
VEGF-F06  (193)  KVVIY GNTNRAS    GVPERFSGSKSATSASLAITGLQAEDEADYYC     QSYDNSLS
VEGF-2A09 (193)  KVVTY GNSNRPS    GVPDRFSASKSGASASLAITGLQAEDEADYYC     QSYDSSLS
VEGF-2B05 (193)  KLVIY GDTFRPS    GVPDRFSGSKSGTSAALAITGLQSEDEADYYC     QSYDSSLS
VEGF-2C11 (196)  RLLIY KISNRFS    GVPDRFSGSGAGTDFTLKISKVEAEDVGVYYC     MQATFPF
VEGF-2D10 (193)  RLLIY GSTNRPS    GVPDRFSGSKSATSASLAITGLQAEDEADYYC     QSYDNSLS
VEGF-2E11 (193)  TLLIY GNNNRPS    GVPDRFSGSKSDTSASLTITGLQAEDEADYYC     QSNDPSLG
VEGF-2F01 (193)  RLLIY GNTNRPS    GVPDRFSGSKSGTSASLAITGLRPEDEADYYC     QSYDNGLS
VEGF-2G03 (196)  RLLIY KISNRFS    GVPDRFSGSGAGTDFTLKISKVEAEDVGVYYC     MQATFPF
VEGF-2G04 (193)  KLLIY GNNNRPS    GVPDRFSGSKSGTSASLAITGLRVEDEGDYYC     QSPDNTLW
VEGF-2G12 (193)  KLLIY GNNNRPS    GVPDRFSGSKSGTSASLAITGLQYDDEADYYC     QSYDSSLS
VEGF-2H07 (193)  KVVIY GNSNRPS    GVPDRFSASKSGASASLAISGLRAEDEADYYC     QSYDSSLS
VEGF-2H08 (193)  KVLIY GNTDRPS    GVPDRFSGSKSGASASLAITGLQAEDEADYYC     QSYDSSLR
VEGF-2H09 (190)  RLLIF AASELQS    GVPSRFSGSASGTEFTLTISSLQPEDFATYYC     QQLBNFLF
VEGF-G12  (194)  KLLIY GNNNRPS    GVPDRFSGSKSGTSASLAITGLQAEDEADYYC     QSYDS-RL
VEGF-2C05 (194)  SYLIY DTSNREF    WTPDRFSGSLLGCRAALTLSGAQPEDEADYYC     FVAYG---A
VEGF-2F09 (194)  KLLIY GDVNRPS    GVPARFSGSKSGTSASLAITGLKAEDEADYYC     QSYDTSLV
VEGF-2F10 (193)  KSLIY ATSILQS    GVPSRFSGYGSGTQFTLTISSLQPEDVATYYC     QQHED---Y ------  -- FR 4 --    ---- Myc Tag ---
VEGF-F06  (242)  ---GYV   FGTGTKVTVLG   GGASLVEFEQKLISEEDL
VEGF-2A09 (242)  ---AYV   FGTGTKVTVLG   GGASLVEFEQKLISEEDL
VEGF-2B05 (242)  ---GYV   FGTGTKVTVLG   GGASLVEFEQKLISEEDL
VEGF-2C11 (245)  I------  FGPGTKVEIKR   GGASLVEFEQKLISEEDL
VEGF-2D10 (242)  ---AYA   FGTGTKVTVLG   GGASLVEFEQKLISEEDL
VEGF-2E11 (242)  GL--HV   FGTGTKVTVLG   GGASLVEFEQKLISEEDL
VEGF-2F01 (242)  AS---YV  FXTGTKVTVLG   GGASLVEFEQKLISEEDL
VEGF-2G03 (245)  I------  FGPGTKVDIKR   GGASLVEFEQKLISEEDL
VEGF-2G04 (242)  G---WV   FGGGTKLTVLG   GGASLVEFEQKLISEEDL
VEGF-2G12 (242)  G---YV   FGTGTKVTVLG   GGASLVEFEQKLISEEDL
VEGF-2H07 (242)  G-SLYV   FGTGTKVTVLG   GGASLVEFEQKLISEEDL
VEGF-2H08 (242)  ---AYV   FGTGTKVTVLG   GGASLVEFEQKLISEEDL
VEGF-2H09 (239)  A------  FGPGTKVEIKR   GGASLVEFEQKLISEEDL
VEGF-G12  (243)  G---VV   FGGGTKLTVLG   GGASLVEFEQKLISEEDL
VEGF-2C05 (242)  I----WF  FGGGTELTVLG   GGASLVEFEQKLISEEDL
VEGF-2F09 (244)  G---SL   FGGGTKLTVLG   GGASLVEFEQKLISEEDL
VEGF-2F10 (242)  P---LT   FGGGTKVDIKR   GGASLVEFEQKLISEEDL
```

VEGF-SPECIFIC HUMAN ANTIBODY

CROSS REFERENCE TO RELATED APPLICATIONS

This application claims the benefit under 35 U.S.C. §119 of Korean Patent application number KR 10-2008-0118124, filed on Nov. 26, 2008, which is herein incorporated by reference in its entirety.

TECHNICAL FIELD

The present disclosure relates to a vascular endothelial growth factor (VEGF)-specific human antibody.

BACKGROUND ART

Vascular endothelial growth factor (VEGF) is known to play a critical role in vasculogenesis and angiogenesis of the developmental process (Soker S et al., *J Cell Biochem.* 85:357-368, 2002). As it has been reported that VEGFR1 is overexpressed not only in vascular endothelial cells, but also in colonic and pancreatic cancer cells, and is directly involved in tumor progression and metastasis, VEGFR1 is considered to play an important role in angiogenesis, tumor growth and metastasis, inflammation, etc (Wey J S et al., *Cancer* 104: 427-438, 2005; Fan F et al., *Oncogene* 24:2647-2653, 2005). VEGF is one of the most important factors in tumor angiogenesis, is expressed in most tumor tissues, such as renal cell cancer (Tomisawa M et al., *Eur J Cancer* 35:133-137, 1999), lung cancer (Volm M et al., *Int J Cancer* 74: 64-68, 1997), breast cancer (Yoshiji H et al., *Cancer Res.* 56:2013-2016, 1996), ovarian cancer (Sowter H M et al., *Lab Invest.* 77:607-614, 1997), etc., and is secreted not only in tumor cells, but also in tumor stromal cells. Although mouse anti-human VEGF monoclonal antibodies did not have much effect on the ex vivo growth of tumor cells in an attempt to use VEGF antagonists to inhibit tumor growth, the antibodies showed significant inhibiting effects for tumor angiogenesis and tumor growth in vivo (Kim K J et al., Nature 362: 841-844, 1993; Borgstrom P et al., Cancer Res. 56:4032-4039).

It is widely known that VEGF is strongly associated with not only tumors, but also other diseases, and various efforts have been made to develop therapeutics for these diseases. Representative examples of these diseases include rheumatoid arthritis (RA) which is a disease associated with angiogenesis, diabetic retinopathy, ischemic retinopathy, psoriasis, etc., and it has been revealed that VEGF functions as an important factor to theses diseases. In the case of RA, it was confirmed that the amount of serum VEGF from RA patients increased compared to that from patients in a control group (Ikeda M et al., *J pathol.* 191:426-33, 2000). The amount of serum VEGF from diabetic patients also increased and the increased blood sugar level caused toxic effects on the endothelium to induce a hyperglycemic pseudo-hypoxic state which induced VEGF production. This showed a correlation between endothelial damage in diabetes and dysfunction (Lim H S et al., *Diabetes Care* 27:2918-24; 2004). Excessive secretion of VEGF in the retina causes ocular neovascularization and hematoma, resulting in visual impairment/blindness. In an effort to prevent visual loss associated with proliferative diabetic retinopathy (PDR) and diabetic macular edema and avoid side effects associated with destructive treatments such as laser treatment, humanized monoclonal anti-VEGF antibody fragments which are selectively bound to all the subtypes of VEGF are used. The compound known as rhuFab V2, produced by Genetech Co., Ltd. is now under clinical research and known to show some effectiveness in prevention of PDR or diabetic macular edema (Heier J S, *Program and abstracts of the American Academy of Opthalmology* 2002 *Annual Meeting*; October 20-23, Orlando, Fla.).

Various types of 40 or more angiogenesis inhibitors are currently under clinical development for various kinds of tumors. VEGF and VEGF receptors are the most representative targets, and include agents which inhibit activity, signal transduction, and production. VEGF inhibitors include antibodies, aqueous VEGF receptors (VEGF traps), etc. Because bevacizumab (Avastin™, Genetech), which is a humanized anti-VEGF monoclonal antibody as an angiogenesis inhibitor for tumor treatment, showed life-prolonging effects on patients with metastatic colorectal cancer, the drug was approved by the FDA in February, 2004. Therefore, the development of these anti-VEGF human monoclonal antibodies has advantages in that the antibodies are a promising candidate for treatment of angiogenesis and various diseases associated with it and may be used in clinical and preclinical settings due to their minimal side effects, and thus the development of various therapeutic agents using these antibodies warrants due attention.

Thus, the present inventors have selected 14 kinds of human antibodies specifically bound to VEGF, confirmed that the human antibodies have binding and neutralizing capacities similar to those of Avastin™ and exhibit cross reactivity with the mouse VEGF, proposed that the human antibodies of the present invention may be effectively used in treatment of VEGF-overexpressed diseases, and have made the present invention.

DISCLOSURE

Technical Problem

One object of the present invention is to provide a VEGF-specific human antibody.

Another object of the present invention is to provide a polynucleotide encoding a heavy chain of the human antibody or a fragment thereof, and an expression vector including the polynucleotide and a constant region of human heavy chain.

Still another object of the present invention is to provide a polynucleotide encoding a light chain of the human antibody or a fragment thereof, and an expression vector including the polynucleotide and a constant region of human light chain.

Even another object of the present invention is to provide a transformant prepared by introducing an expression vector including a polynucleotide encoding the heavy chain of the human antibody or an immunologically active fragment thereof into a host cell.

Yet another object of the present invention is to provide a transformant prepared by introducing an expression vector including a polynucleotide encoding the light chain of the human antibody or an immunologically active fragment thereof into a host cell.

Further another object of the present invention is to provide a transformant prepared by introducing an expression vector including a polynucleotide encoding the heavy chain of the human antibody or a fragment thereof and an expression vector including a polynucleotide encoding the light chain or a fragment thereof simultaneously into a host cell.

Still further another object of the present invention is to provide a method for preparing a VEGF-specific human antibody by incubating the transformant.

The present invention also provides a composition including the human antibody.

The present invention also provides a pharmaceutical composition including the human antibody.

Another object of the present invention is to provide a method for treating diseases caused by VEGF-overexpression, the method including administering a pharmaceutically effective amount of the human antibody to a subject.

Still another object of the present invention is to provide a composition including the human antibody and a radioactive isotope.

Even another object of the present invention is to provide an immunodetection method for detecting an ex vivo VEGF-overexpressed cancer, including contacting a composition including the radioactive isotope with a cancer cell.

Yet another object of the present invention is to provide a method for imaging an in vivo VEGF-overexpressed cancer, including administering a composition including the radioactive isotope to a subject.

Further another object of the present invention is to provide a method for treating an in vivo VEGF-overexpressed cancer by using a composition including the radioactive isotope.

Still further another object of the present invention is to provide a method for prognostic evaluation of a VEGF-overexpressed cancer treatment using a composition including the radioactive isotope.

Even further another object of the present invention is to provide a method for measuring side effects of the human antibody, including administering the human antibody to an animal experiment model.

Technical Solution

To achieve the objects, the present invention provides a VEGF-specific human antibody including a heavy chain including a heavy chain variable region ($V_H$) including a heavy chain complementarity determining region (hereinafter, HCDR) 1 having an amino acid sequence selected from the group consisting of SEQ ID Nos. 5 to 17, HCDR 2 having an amino acid sequence selected from the group consisting of SEQ ID Nos. 18 to 30, and HCDR 3 having an amino acid sequence selected from the group consisting of SEQ ID Nos. 31 to 43, or a fragment thereof; and a light chain including a light chain variable region ($V_L$) including a light chain complementarity determining region (hereinafter, LCDR) 1 having an amino acid sequence selected from the group consisting of SEQ ID Nos. 57 to 69 and SEQ ID Nos. 130 to 142, LCDR 2 having an amino acid sequence selected from the group consisting of SEQ ID Nos. 70 to 82 and SEQ ID Nos. 143 to 152, and LCDR 3 having an amino acid sequence selected from the group consisting of SEQ ID Nos. 83 to 93 and SEQ ID Nos. 153 to 164, or a fragment thereof.

The present invention also provides a polynucleotide encoding a heavy chain of the human antibody or an immunologically active fragment thereof, and an expression vector including the polynucleotide.

The present invention also provides a polynucleotide encoding a light chain of the human antibody or an immunologically active fragment thereof, and an expression vector including the polynucleotide.

The present invention also provides a transformant prepared by introducing an expression vector including a polynucleotide encoding a heavy chain of the human antibody or an immunologically active fragment thereof into a host cell.

The present invention also provides a transformant prepared by introducing an expression vector including a polynucleotide encoding a light chain of the human antibody or an immunologically active fragment thereof into a host cell.

The present invention also provides a transformant prepared by introducing an expression vector including a polynucleotide encoding a heavy chain of the human antibody or an immunologically active fragment thereof and an expression vector including a polynucleotide encoding a light chain of the human antibody or an immunologically active fragment thereof simultaneously into a host cell.

The present invention also provides a method for preparing a VEGF-specific human antibody by incubating the transformant.

The present invention also provides a composition including the human antibody.

The present invention also provides a pharmaceutical composition including the human antibody.

The present invention also provides a method for treating a disease caused by VEGF-overexpression, including administering a pharmaceutically effective amount of the human antibody to a subject with the disease.

The present invention also provides a composition including the human antibody, a light or heavy chain of the human antibody or an immunologically active fragment thereof, and a radioactive isotope.

The present invention also provides an immunodetection method for detecting an ex vivo VEGF-overexpressed cancer, including contacting a composition including the radioactive isotope with a cancer cell.

The present invention also provides a method for imaging an in vivo VEGF-overexpressed cancer, the method including:

1) administering a diagnostically effective amount of a composition including the radioactive isotope to a subject; and 2) obtaining a detection image for the subject.

The present invention also provides a method for treating an in vivo VEGF-overexpressed cancer, the method including:

1) intravenously administering a composition including the radioactive isotope to a subject;

2) detecting the composition of Step 1) to identify tumor cells; and 3) eliminating the tumor cells identified in Step 2) by surgical operation.

The present invention also provides a method for prognostic evaluation of a cancer patient, the method including:

1) intravenously administering a composition including the radioactive isotope to a patient whose tumor has been eliminated;

2) detecting the composition of Step 1) to identify tumor cells; and 3) judging that all tumor cells have been eliminated when tumor cells are not detected in step 2).

Furthermore, the present invention provides a method for measuring side effects of the human antibody, including administering the human antibody to an animal experiment model with a disease caused by VEGF-overexpression.

Advantageous Effect

The VEGF-specific human antibody of the present invention may be used in diagnosis of diseases caused by the VEGF-overexpression, classification of the diseases, visualization, treatment, and prognostic evaluation.

DESCRIPTION OF DRAWINGS

The above and other objects, features and other advantages of the present invention will be more clearly understood from the following detailed description taken in conjunction with the accompanying drawings, in which:

FIG. 6 is a photo illustrating results of diversity of human VEGF monoclonal phage antibodies to VEGF, confirmed by fingerprinting.

FIG. 7 is a list of sequences illustrating analysis results of a polypeptide used in a heavy chain CDR of human VEGF monoclonal phage antibodies to VEGF.

FIG. 8 is a list of sequences illustrating analysis results of a polypeptide used in a light chain CDR of human VEGF monoclonal phage antibodies to VEGF.

FIG. 9 is a group of graphs illustrating results comparing binding specificities of human VEGF monoclonal antibodies:
  a: C5, E9, F6, G12, A4, C11, and F2; and b: H7, G9, C9, B12, F9, D12, and C12.

FIG. 10 is a group of photos illustrating results, confirming that neutralizing capacities inhibited the tube formation of human VEGF monoclonal antibodies in HUVEC cells.

FIG. 11 is a group of graphs illustrating results of the measurement of cross-reactivity of human VEGF monoclonal antibodies with hVEGF and mVEGF.

FIG. 16 is a group of drawings illustrating analysis results of a polypeptide used in a light chain CDR of an LC shuffling monoclonal phage antibody.

BEST MODE

Figure 1:
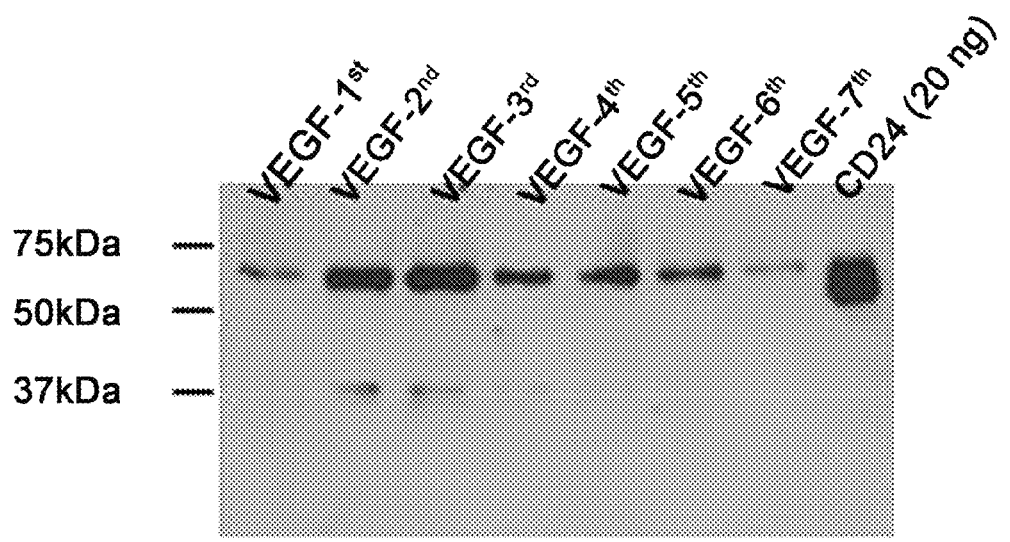
FIG. 1 is a photo illustrating results of VEGF protein expression in a pYK602-VEGF vector, confirmed by Western blot.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the terms of the present invention will be described.

"Variable region" means a region of an antibody molecule which specifically binds to an antigen and demonstrates modifications in sequence, which is exemplified by CDR1, CDR2, and CDR3. Between the CDRs, there is a framework region (FR) which supports the CDR loop.

"Complementarity determining region" is a loop-shaped site involved in antigen recognition, and specificity of an antibody against antigen depends on modification in that site.

"Panning" refers to a process of selecting only a phage expressing a peptide which binds to a target molecule (antibody, enzyme, cell-surface receptor, etc.) on the coat of the phage from a phage library displaying the peptide on the coat.

Hereinafter, the present invention will be described in detail.

The present invention provides a VEGF-specific human antibody, including: a heavy chain including a heavy chain variable region ($V_H$) including a heavy chain complementarity determining region (hereinafter, HCDR) 1 having an amino acid sequence selected from the group consisting of SEQ ID Nos. 5 to 17, HCDR 2 having an amino acid sequence selected from the group consisting of SEQ ID Nos. 18 to 30, and HCDR 3 having an amino acid sequence selected from the group consisting of SEQ ID Nos. 31 to 43, or a fragment thereof; and a light chain including a light chain variable region ($V_L$) including a light chain complementarity determining region (hereinafter, LCDR) 1 having an amino acid sequence selected from the group consisting of SEQ ID Nos. 57 to 69 and SEQ ID Nos. 130 to 142, LCDR 2 having an amino acid sequence selected from the group consisting of SEQ ID Nos. 70 to 82 and SEQ ID Nos. 143 to 152, and LCDR 3 having an amino acid sequence selected from the group consisting of SEQ ID Nos. 83 to 93 and SEQ ID Nos. 153 to 164, or a fragment thereof.

Preferably, the heavy chain variable region has an amino acid sequence selected from the group consisting of SEQ ID Nos. 44 to 56, and the light chain variable region has an amino acid sequence selected from the group consisting of SEQ ID Nos. 94 to 106 and SEQ ID Nos. 165 to 178.

The antibody includes not only a whole antibody, but also a functional fragment of the antibody molecule. The whole antibody has a structure with two full-length light chains and two full-length heavy chains, and each light chain is linked to heavy chain by disulfide bond. The functional fragment of an antibody molecule indicates a fragment retaining a antigen-binding function, and examples of the antibody fragment include (i) Fab fragment consisting of light chain variable region ($V_L$), heavy chain variable region ($V_H$), light chain constant region ($C_L$), and heavy chain $1^{st}$ constant region ($C_{H1}$); (ii) Fd fragment consisting of $V_H$ and $C_{H1}$ domains; (iii) Fv fragment consisting of $V_L$ and $V_H$ domains of a monoclonal antibody; (iv) dAb fragment consisting of $V_H$ domain (Ward E S et al., Nature 341:544-546 (1989)); (v) separated CDR region; (vi) F(ab')$_2$ fragment including two linked Fab fragments, as a divalent fragment; (vii) single chain Fv molecule (ScFv) in which $V_H$ and $V_L$ domains are linked by a peptide linker to form an antigen binding site; (viii) bi-specific single chain Fv dimmer (PCT/US92/09965), and (ix) multivalent or multi-specific diabody fragment (WO94/13804) prepared by gene fusion.

In the present invention, a human antibody against VEGF was obtained as ScFV by using phage display technology and screened as a mono phage clone. As a result, 14 kinds of VEGF-specific monoclonal phages were obtained.

In a specific example of the present invention, VEGF obtained through recombinant technology (see FIGS. 1 to 4) was used in preparation of monoclonal antibodies. The VEGF was reacted with a library phage constructed from human naive scFV library cells, followed by panning and screening of mono clones strongly binding to the VEGF antigen (see Tables 1 & 2 and FIG. 5). The selected mono clones were identified by fingerprinting (see FIG. 6), followed by sequencing to identify CDR regions of $V_H$ and $V_L$ of the antibody (see Table 5 and FIGS. 7 and 8). The Ig BLAST program of NCBI (//www.ncbi.nlm.nih.gov/igblast/) was used for identification of similarity between the antibody and a germ line antibody group (see Table 6). As a result, 14 kinds of VEGF-specific phage antibodies were obtained. The selected monoclonal antibodies exhibited binding capacities in the order of G12>D12>E9>F6>H7>C5>B12>G9>F9>C11>F2>A4>C9>C12 (see FIGS. 9a and 9b), and it was observed that they significantly inhibited a capillary-like tube formation of HUVEC cells, induced by VEGF (see FIG. 10). E9, F6, and G12 monoclonal antibodies showing binding capacities similar to that of Avastin™ all exhibited strong affinities for mouse VEGF similar to those for human VEGF, leading to a cross reaction (see Table 8 and FIG. 11). Because Avastin™ is not reacted with mouse VEGF at all, it has been difficult to perform animal experimental studies on side effects by Avastin™ However, the VEGF neutralizing human antibody of the present invention is cross reacted with the mouse, indicating that it is highly different from the conventional anti-cancer drug Avastin™ in terms of epitope. Because the VEGF neutralizing human antibody of the present invention exhibits a high cross reactivity with mouse VEGF, it may be used in animal experimental studies.

A library phage with a light chain shuffling was prepared for F6 and G12 monoclonal antibodies exhibiting neutralizing capacities similar to those of the Avastin™. The prepared library phage was reacted with VEGF for panning, followed by screening of monoclones strongly binding to VEGF antigen (see Tables 10 & 11 and FIG. 14). The selected monoclones were confirmed by a fingerprinting process (see FIG. 15), followed by sequencing to confirm CDR regions of $V_H$ and $V_L$ of the antibody. Because CDR regions of $V_H$ of the antibody selected by an LC shuffling were identical to each other, CDR regions of $V_L$ of the antibody were prepared (see Table 12 and FIG. 16). Homology between the antibody and germ line antibody group was investigated (see Table 13). As a result, 15 VEGF specific LC shuffling monoclonal phage antibodies were obtained and their VEGF binding capacities were confirmed (see FIG. 14). A confirmation result of human VEGF binding capacities of the LC shuffling monoclonal phage antibodies showed that the antibodies had high affinities similar to those of F6 and G12, except for 2C11, 2G03, 2C05, and 2F10.

The present invention also provides a polynucleotide encoding a heavy chain of the human antibody or an immunologically active fragment thereof, and an expression vector including the polynucleotide.

The present invention also provides a polynucleotide encoding a light chain of the human antibody or an immunologically active fragment thereof, and an expression vector including the polynucleotide.

Figure 5:
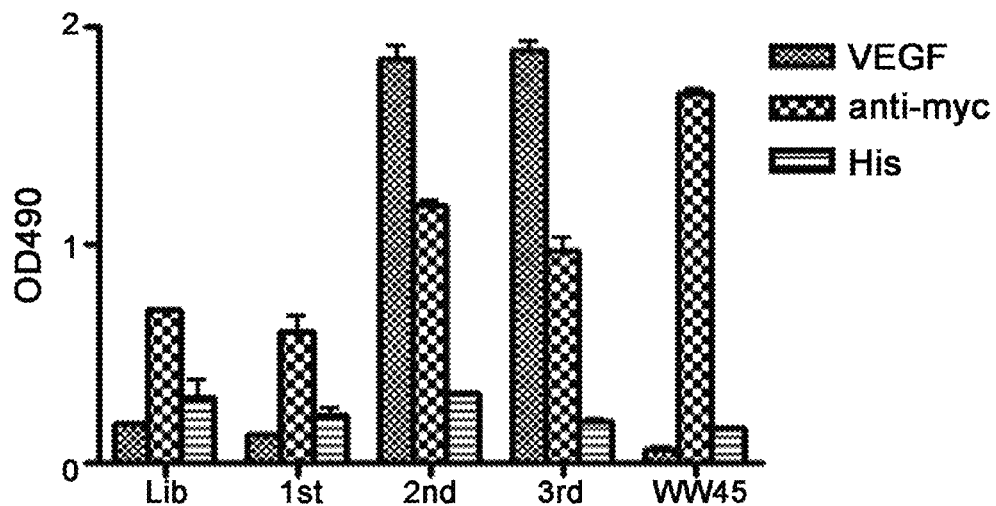
FIG. 5 is a graph illustrating results of phage screening in 1st to 3rd pannings.

In a specific embodiment of the present invention, VEGF obtained by recombinant technology was used to screen mono clones strongly binding to VEGF antigens (see Tables 1 and 2 and FIG. 5). The selected monoclones were identified by fingerprinting (see FIG. 6), followed by sequencing to identify CDR regions of $V_H$ and $V_L$ of the antibody (see Table 5 and FIGS. 7 and 8). The identification of similarity between the antibody and a germ line antibody group was performed (see FIG. 6). As a result, 14 kinds of VEGF-specific phage antibodies were obtained. Binding capacities to VEGF of the selected monoclonal antibodies were measured (see FIGS. 9a & 9b), and it was observed that the antibodies significantly inhibited a capillary-like tube formation of HUVEC cells, induced by VEGF (see FIG. 10). E9, F6, and G12 monoclonal antibodies showing binding capacities similar to that of Avastin™ all exhibited strong affinities for mouse VEGF similar to those for human VEGF, leading to a cross reaction (see Table 8 and FIG. 11). Because Avastin™ is not reacted with mouse VEGF at all, it has been difficult to perform animal experimental studies on side effects by Avastin™ However, the VEGF neutralizing human antibody of the present invention is cross reacted with the mouse, indicating that it is highly different from the conventional anti-cancer drug Avastin™ in terms of epitope. Because the VEGF neutralizing human antibody of the present invention exhibits a high cross reactivity with mouse VEGF, it may be used in animal experimental studies.

In the polynucleotide encoding light and heavy chains of the human antibody of the present invention or a fragment thereof, due to degeneracy of the codon or in consideration of a preferred codon in an organism where light and heavy chains of the human antibody or a fragment thereof are to be expressed, various modifications may be made in a coding region within a scope that the amino acid sequences of light and heavy chains or a fragment thereof are not changed, and various changes or modifications may be made even in portions other than the coding region within a scope that the gene expression is not affected. It will be appreciated by those skilled in the art that these modified genes are also included within the scope of the present invention. That is, one or more nucleotides may be modified by substitution, deletion, insertion, or a combination thereof as long as the polynucleotide of the present invention encodes a protein with an equivalent activity thereof, and they are also included in the present invention. The sequence of the polynucleotide may be a single or double chain, and a DNA or RNA (mRNA) molecule.

In preparation of the expression vector, an expression control sequence such as a promoter, a terminator, an enhancer, etc., a sequence for membrane targeting or secretion, etc. may be appropriately selected according to a kind of host cell in which light and heavy chains of the human antibody or a fragment thereof are to be produced, and may be variously combined according to its purpose.

The expression vector of the present invention includes, but is not limited to, a plasmid vector, a cosmid vector, a bacteriophage, and a viral vector. A suitable expression vector may include expression regulatory elements such as a promoter, an operator, an initiation codon, a stop codon, a polyadenylation signal, and an enhancer and a signal sequence or leader sequence for membrane targeting or secretion, and may be variously prepared according to its purpose. A promoter of the expression vector may be constitutive or inductive. Examples of the signal sequence for use may include, but is not limited to, a PhoA signal sequence and an OmpA signal sequence for genus *Escherichia* hosts; an α-amylase signal sequence and a subtilicin signal sequence for genus *Bacillus* hosts; an MFα signal sequence and an SUC2 signal sequence for yeast hosts; and an insulin signal sequence, an α-interferon signal sequence, and an antibody molecule signal sequence for animal cell hosts. In addition, the expression vector may include a selection marker for selecting host cells containing the vector, and a replication origin when it is a replicable expression vector.

The present invention also provides a transformant prepared by introducing an expression vector including a polynucleotide encoding a heavy chain of the human antibody or an immunologically active fragment thereof into a host cell.

The present invention also provides a transformant prepared by introducing an expression vector including a polynucleotide encoding a light chain of the human antibody or an immunologically active fragment thereof into a host cell.

The present invention also provides a transformant prepared by introducing an expression vector including a polynucleotide encoding a heavy chain of the human antibody or a fragment thereof and an expression vector including a polynucleotide encoding a light chain of the human antibody or a fragment thereof simultaneously into a host cell.

In a specific example of the present invention, genes encoding light and heavy chains of a monoclonal phage were obtained and linked to a vector, respectively, and then a whole human IgG antibody expressed by introducing the expression vectors simultaneously into a host cell was identified. The human antibody was obtained to identify a binding capacity (see FIGS. 9a & 9b), a neutralizing capacity to VEGF (see FIG. 10), and a cross reactivity with mouse and human VEGF (see Table 8 and FIG. 11).

The expression vector according to the present invention may be transformed into a suitable host cell, for example, *E. coli* or yeast cell, and the transformed host cell may be incubated to produce light and heavy chains of the human antibody of the present invention or a fragment thereof in mass quantities. Incubation methods and media conditions suitable for a kind of host cell may be easily chosen from those known to those skilled in the art. The host cell may be a prokaryote such as *E. coli* or *Bacillus subtilis*. In addition, it may be a eukaryotic cell derived from a yeast such as *Saccharomyces cerevisiae*, an insect cell, a vegetable cell, and an animal cell. More preferably, the animal cell may be an autologous or allogeneic animal cell. A transformant prepared through introduction into an autologous or allogeneic animal cell may be administered to a subject for use in cellular therapy for cancer. As for a method for introducing an expression vector into the host cell, it is possible to use any method if it is known to those skilled in the art.

The present invention also provides a method for preparing VEGF-specific human antibodies, the method including:

1) incubating the transformant; and
2) purifying the human antibody from the medium.

As for the culture medium, it is desirable to select and use a culture medium suitable for the transformant among those known to those skilled in the art. As for the method for purifying human antibodies, it is possible to use any method known to those skilled in the art.

In a specific example of the present invention, genes encoding light and heavy chains of a monoclonal phage were obtained and linked to a vector, respectively, and then a whole human IgG antibody expressed by introducing the expression vectors simultaneously into a host cell was identified. The human antibody was obtained to identify a binding capacity (see FIGS. 9a & 9b), a neutralizing capacity to VEGF (see FIG. 10), and a cross reactivity with mouse and human VEGF (see Table 8 and FIG. 11).

The present invention also provides a composition including the human antibody.

The present invention also provides a pharmaceutical composition including the human antibody.

The disease caused by VEGF-overexpression includes one associated with cancer or angiogenesis. The cancer is preferably one selected from the group consisting of, but not limited to, colorectal cancer, renal cell cancer, lung cancer, breast cancer, and ovarian cancer, and includes all the VEGF-overexpressed cancers. The diseases associated with angiogenesis also include rheumatoid arthritis (RA), diabetic retinopathy, ischemic retinopathy, psoriasis, proliferative diabetic retinopathy (PDR), diabetic macular edema, etc.

In a specific example of the present invention, it was observed that VEGF monoclonal antibodies exhibiting binding capacities to VEGF (see FIGS. 9a and 9b) significantly inhibited a capillary-like tube formation of HUVEC cells, induced by VEGF in a human umbilical vein endothelial cell line (see FIG. 10). E9, F6, and G12 monoclonal antibodies showing binding capacities similar to that of Avastin™ all exhibited strong affinities for mouse VEGF similar to those for human VEGF, leading to a cross reaction (see Table 8 and FIG. 11). Because Avastin™ is not reacted with mouse VEGF at all, it has been difficult to perform animal experimental studies on side effects by Avastin™. However, the VEGF neutralizing human antibody of the present invention is cross reacted with the mouse, indicating that it is highly different from the conventional anti-cancer drug Avastin™ in terms of epitope. Because the VEGF neutralizing human antibody of the present invention exhibits a high cross reactivity with mouse VEGF, it may be used in animal experimental studies. Thus, the monoclonal antibody of the present invention may be useful as a composition for prevention and treatment of VEGF-overexpressed diseases.

The pharmaceutical composition of the present invention may selectively contain the VEGF-specific human antibody or the transformant, and may additionally contain one or more effective ingredients exhibiting functions identical or similar to those of the ingredient. For administration, the pharmaceutical composition of the present invention may be formulated by including one or more pharmaceutically acceptable carriers in addition to the effective ingredients described above. For example, the pharmaceutically acceptable carrier includes saline solution, sterilized water, Ringer's solution, buffered saline solution, dextrose solution, maltodextrin solution, glycerol, ethanol, liposome, and at least one combination thereof, and other general additives such as antioxidants, buffer solution, bacteriostatic agents, etc. may be added if necessary. In addition, it may be formulated in the form of an injectable formulation such as aqueous solution, suspension, emulsion, etc. by additionally adding diluent, dispersing agent, surfactant, binder and lubricant, and antibodies and other ligands specific to a target cell may be used in combination with the carrier to be specifically reacted with the target cell. Furthermore, the composition may be preferably formulated according to each disease or ingredient using a suitable method in the art or a method which is taught in Remington's Pharmaceutical Science, Mack Publishing Company, Easton Pa.

The pharmaceutical composition of the present invention may be parenterally administered, and the parenteral administration is effected by subcutaneous injection, intravenous injection, intramuscular injection, or intrapleural injection. For parenteral administration, the pharmaceutical composition of the present invention may be mixed with a stabilizer or buffer to prepare a solution or suspension, which may then be provided as ampoules or vials each containing a unit dosage form.

The pharmaceutical composition of the present invention may be prepared in various forms according to the route of administration. For example, the pharmaceutical composition of the present invention may be formulated to a sterilized aqueous solution or dispersion for injection, or may be prepared in a freeze-dried form through a freeze-drying technique. The freeze-dried pharmaceutical composition may be stored typically at about 4° C. and may be reconstituted with a stabilizer that may contain an adjuvant such as saline solution and/or HEPE.

In a method of the present invention, factors affecting the amount of the pharmaceutical composition to be administered include, but are not limited to, administration mode, administration frequency, specific disease under treatment, severity of disease, history of disease, whether the subject is under treatment in combination with other therapeutics, the subject's age, height, weight, health, and physical conditions. As the patient's weight under treatment increases, the pharmaceutical composition of the present invention may preferably be administered in increasing amounts.

In addition, the pharmaceutical composition of the present invention may be administered in combination with chemotherapy.

The present invention also provides a method for treating a disease caused by VEGF-overexpression, the method including administering a pharmaceutically active amount of the human antibody to a subject with the disease caused by VEGF-overexpression.

The disease caused by VEGF-overexpression includes one associated with cancer or angiogenesis. The cancer is preferably one selected from the group consisting of, but not limited to colorectal cancer, renal cell cancer, lung cancer, breast cancer, and ovarian cancer, and includes all the VEGF-overexpressed cancers. The diseases associated with angiogenesis also include rheumatoid arthritis, diabetic retinopathy, ischemic retinopathy, psoriasis, proliferative diabetic retinopathy (PDR), diabetic macular edema, etc.

In a specific example of the present invention, it was observed that VEGF monoclonal antibodies showing binding capacities to VEGF (see FIGS. 9a & 9b) significantly inhibited a capillary-like tube formation of HUVEC cells, induced by VEGF in a human umbilical vein endothelial cell line (see FIG. 10). E9, F6, and G12 monoclonal antibodies showing binding capacities similar to that of Avastin™ all exhibited strong affinities for mouse VEGF similar to those for human VEGF, leading to a cross reaction (see Table 8 and FIG. 11). Because Avastin™ is not reacted with mouse VEGF at all, it has been difficult to perform animal experimental studies on side effects by Avastin™. However, the VEGF neutralizing human antibody of the present invention is cross reacted with the mouse, indicating that it is highly different from the conventional anti-cancer drug Avastin™ in terms of epitope. Because the VEGF neutralizing human antibody of the present invention exhibits a high cross reactivity with mouse VEGF, it may be used in animal experimental studies. Thus, the monoclonal antibody of the present invention may be useful as a composition for prevention and treatment of VEGF-overexpressed diseases.

The subject applicable in the present invention is a vertebrate, preferably a mammal, more preferably an experimental animal such as mouse, rabbit, guinea pig, hamster, dog, and cat, and most preferably a primate such as chimpanzee and gorilla.

The method for administering the human antibody of the present invention may be conducted by parenteral administration (for example, intravenous, subcutaneous, intraperitoneal, or local administration) according to the purpose of use, and preferably by intravenous administration. In administration for solid cancer, local administration may be often preferable for rapid and facilitated access of the antibody. The dose may vary depending on weight, age, sex, and health condition of a patient, diet, administration time, administration method, excretion rate, and severity of disease. The single dose is in the range of 5 to 500 mg/m$^2$, which may be administered daily or weekly. The effective amount may be controlled at the discretion of a doctor treating the patient.

The human antibody of the present invention may be used alone or in combination with surgery, hormone therapy, chemical therapy, and a biological response controller for treatment of a patient.

The present invention also provides a composition including the human antibody, light and heavy chains of the human antibody, or an immunologically active fragment thereof, and a radioactive isotope.

The composition may be used for radioimmuno treatment and detection of a disease caused by VEGF-overexpression. The disease caused by VEGF-overexpression includes one associated with cancer or angiogenesis. The cancer is preferably one selected from the group consisting of, but not limited to, colorectal cancer, renal cell cancer, lung cancer, breast cancer, and ovarian cancer, and includes all the VEGF-overexpressed cancers. The diseases associated with angiogenesis also include rheumatoid arthritis, diabetic retinopathy, ischemic retinopathy, psoriasis, proliferative diabetic retinopathy (PDR), diabetic macular edema, etc.

In a specific example of the present invention, it was confirmed that the monoclonal VEGF antibody showed strong binding capacity to VEGF (see FIGS. 9a and 9b). Thus, the monoclonal antibody of the present invention may be useful as a composition for radioimmuno treatment of diseases caused by VEGF-overexpression and including a radioactive isotope.

Examples of preferred radioactive isotopes include $^3$H, $^{11}$C, $^{14}$C, $^{18}$F, $^{64}$Cu, $^{76}$Br, $^{86}$Y, $^{99m}$Tc, $^{111}$In, $^{123}$I, $^{177}$Lu, and a mixture or combination thereof. The radioactive isotope is characterized by the fact that it is bound to a human antibody and included in a carrier to which the human antibody is bound.

The present invention also provides an immunodetection method for detecting an ex vivo VEGF-overexpressed cancer, the method including: contacting a composition including the radioactive isotope with cancer cells.

The VEGF-overexpressed cancer is preferably one selected from the group consisting of, but not limited to, colorectal cancer, renal cell cancer, lung cancer, breast cancer, and ovarian cancer, and includes all the VEGF-overexpressed cancers.

In a specific example of the present invention, it was confirmed that the monoclonal VEGF antibody showed strong binding capacity to VEGF (see FIGS. 9a and 9b). Thus, the monoclonal antibody of the present invention may be useful as a composition for radioimmuno treatment of VEGF-overexpressed diseases and including a radioactive isotope.

The composition including the radioactive isotope may be bound to a solid substrate in order to facilitate the subsequent steps such as washing or separation of complexes. The solid substrate includes, for example, synthetic resin, nitrocellulose, glass substrate, metal substrate, glass fiber, microsphere, microbead, etc. The synthetic resin includes polyester, polyvinyl chloride, polystyrene, polypropylene, PVDF, nylon, etc.

In addition, cancer cell may be appropriately diluted before it is contacted with a composition including the radioactive isotope.

The present invention also provides a method for imaging a VEGF-overexpressed cancer, the method including 1) administering a diagnostically effective amount of a compound including the radioactive isotope to a subject; and 2) obtaining a detection image for the subject.

The VEGF-overexpressed cancer is preferably one selected from the group consisting of, but not limited to, colorectal cancer, renal cell cancer, lung cancer, breast cancer, and ovarian cancer, and includes all the VEGF-overexpressed cancers.

In a specific example of the present invention, it was confirmed that the monoclonal VEGF antibody showed strong binding capacity to VEGF (see FIGS. 9a and 9b). Thus, the monoclonal antibody of the present invention may be useful in a method for imaging a VEGF-overexpressed cancer.

The detection image is characterized by the fact that it is obtained by near-infrared light imaging, PET, MRI, or ultrasonic imaging.

The present invention also provides a method for treating an in vivo VEGF-overexpressed cancer, the method including:

1) intravenously administering a composition including the radioactive isotope to a subject;
2) detecting the composition of Step 1) to identify tumor cells; and
3) eliminating the tumor cells identified in Step 2) by surgical operation.

The VEGF overexpressed cancer is preferably one selected from the group consisting of, but not limited to, colorectal cancer, renal cell cancer, lung cancer, breast cancer, and ovarian cancer, and includes all the VEGF-overexpressed cancers.

In a specific example of the present invention, it was observed that VEGF monoclonal antibodies showing binding capacities to VEGF (see FIGS. 9a and 9b) significantly inhibited a capillary-like tube formation of HUVEC cells, induced by VEGF in a human umbilical vein endothelial cell line (see FIG. 10). E9, F6, and G12 monoclonal antibodies showing binding capacities similar to that of Avastin™ all exhibited strong affinities for mouse VEGF similar to those for human VEGF, leading to a cross reaction (see Table 8 and FIG. 11). Because Avastin™ is not reacted with mouse VEGF at all, it has been difficult to perform animal experimental studies on side effects by Avastin™. However, the VEGF neutralizing human antibody of the present invention is cross reacted with the mouse, indicating that it is highly different from the conventional anti-cancer drug Avastin™ in terms of epitope. Because the VEGF neutralizing human antibody of the present invention exhibits a high cross reactivity with mouse VEGF, it may be used in animal experimental studies. Thus, the monoclonal antibody of the present invention may be useful as a composition for prevention and treatment of VEGF-overexpressed diseases. Thus, the monoclonal antibodies of the present invention may be useful in prevention and treatment of VEGF-overexpressed cancers.

The present invention also provides a method for prognostic evaluation of a cancer patient, the method including:

1) intravenously administering a composition including the radioactive isotope to a patient whose tumor has been eliminated;
2) detecting the composition of Step 1) to identify tumor cells; and
3) judging that all tumor cells have been eliminated when tumor cells are not detected in step 2).

In addition, the present invention provides a method for measuring side effects of the human antibody, the method including administering the human antibody to an animal experiment model.

The animal experiment model may be preferably an animal with a disease caused by VEGF-overexpression.

Mode For Invention

Hereinafter, the present invention will be described in more detail with reference to examples.

However, the following examples are provided for illustrative purposes only, and the scope of the present invention should not be limited thereto in any manner.

Example 1

Preparation of VEGF Antigen Protein

<1-1> VEGF Gene Cloning
<1-1-1> Cloning Using YK602

A plasmid (UG-0036-D12) containing human VEGF gene was provided from KUGI (Korean UniGene Information) of the Center for Functional Analysis of Human Genome in Korea Research Institute of Bioscience and Biotechnology. The plasmid was used as a template DNA. In order to express only the domain of the VEGF, a forward primer (SEQ ID No. 1: 5'-GCTCTAGAGTGATGAACTTTCTGCTGTCTT-3') and a reverse primer (SEQ ID No. 2: 5'-CGGAATTCCCGC-CTCGGCTTGTCACA-3') were used to amplify the gene under the following conditions. The gene was treated with XbaI and EcoRI, followed by subcloning into a pcDNA3.1/myc-His (−) vector (V80020: Invitrogen, USA) using a ligase. PCR conditions are as follows: when a total reaction reagent was 50 μl, 500 ng of the template was introduced and a reaction at 94° C. for 5 minutes, 25 cycles of reactions at 95° C. for 30 seconds, at 55° C. for 30 seconds, and at 72° C. for one and a half minutes, and at a reaction at 72° C. for 10 minutes were performed to get a PCR product.

Figure 13A:
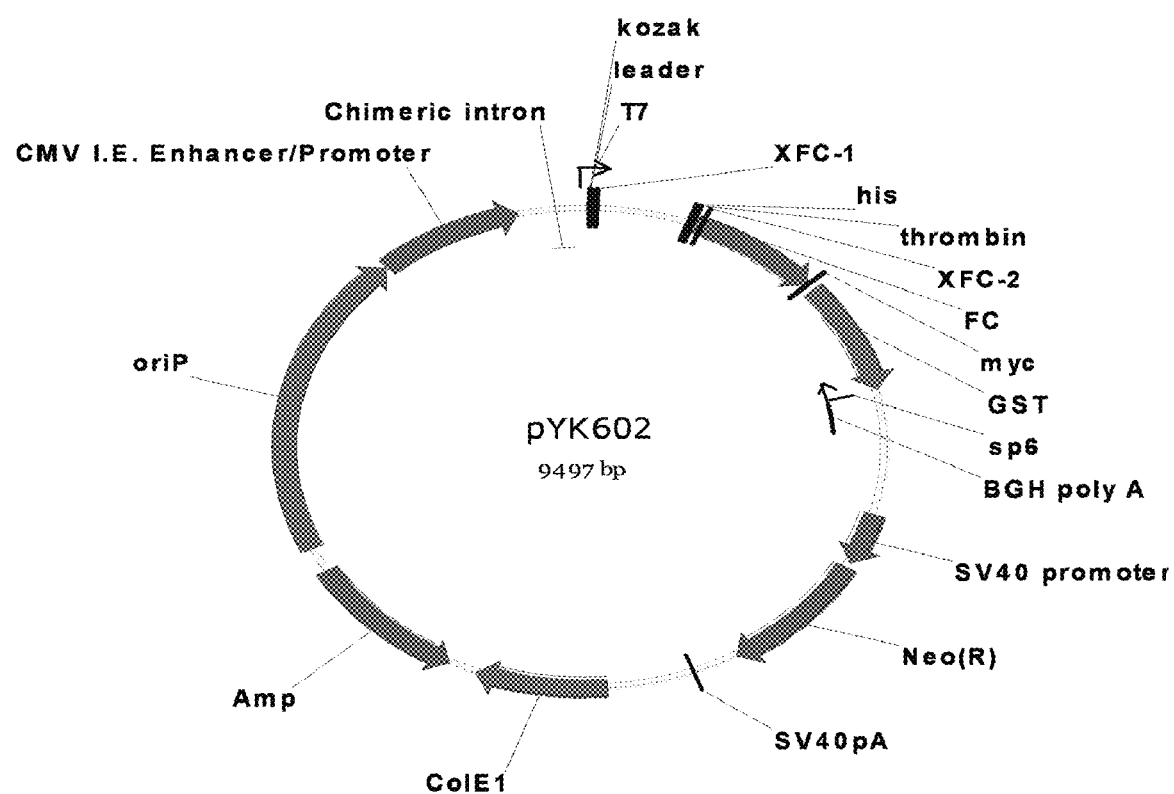
FIG. 13 is a group of drawings illustrating cleavage maps of pYK602, pYK602-His, and pYK603 vectors:
  a: pYK602 vector; b: pYK602-His vector; and c: pYK603 vector.

The pcDNA3.1-VEGF was used as a template DNA, and a forward primer (SEQ ID No. 3: 5'-CAGGGGGC-CGTGGGGGCCGCAGAAGGAGGAGGGCAG-3') and a reverse primer (SEQ ID No. 4: 5'-TAGCGGCCGACGCG-GCCAACCGCCTCGGCTTGTCACA-3') were used to amplify the gene under the following conditions. The gene was treated with SfiI, and a ligase was used to subclone the gene into a pYK602 vector (FIG. 13a). PCR conditions are as follows: when a total reaction reagent was 50 μl, 500 ng of the template was introduced and a reaction at 95° C. for 5 minutes, 25 cycles of reactions at 95° C. for 30 seconds, at 58° C. for 30 seconds, and at 72° C. for 1 minute, and at a reaction at 72° C. for 10 minutes were performed to get a PCR product. Furthermore, the base sequence of the subcloned pYK602-VEGF vector was identified.

Figure 13B:
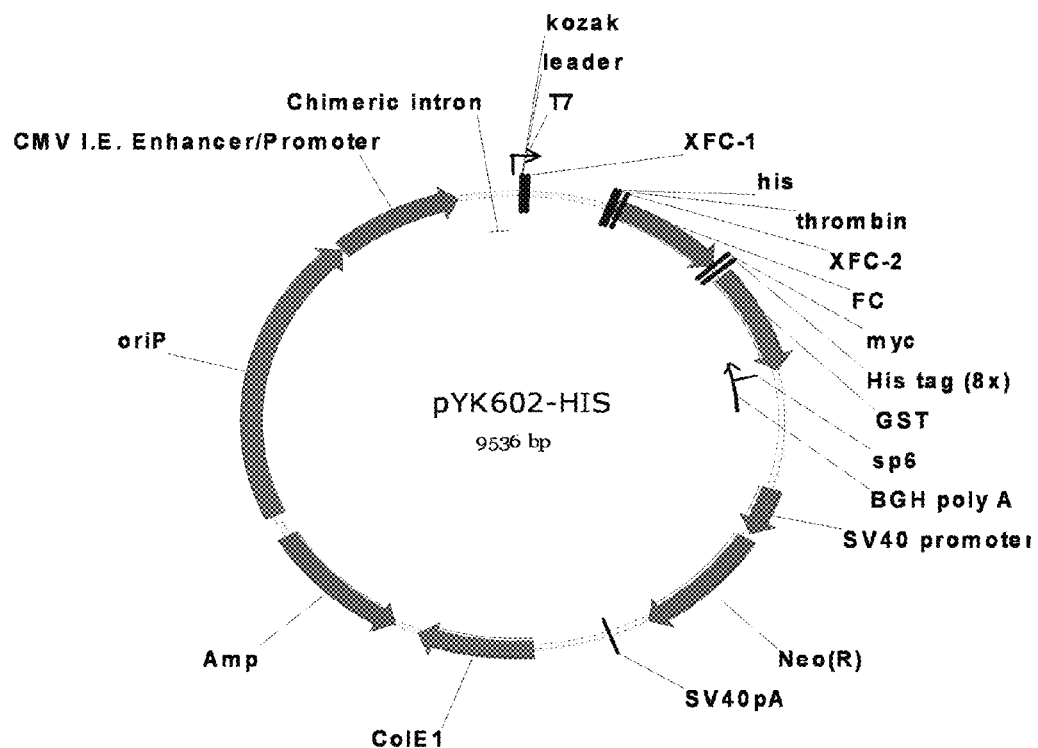
Figure 13C:
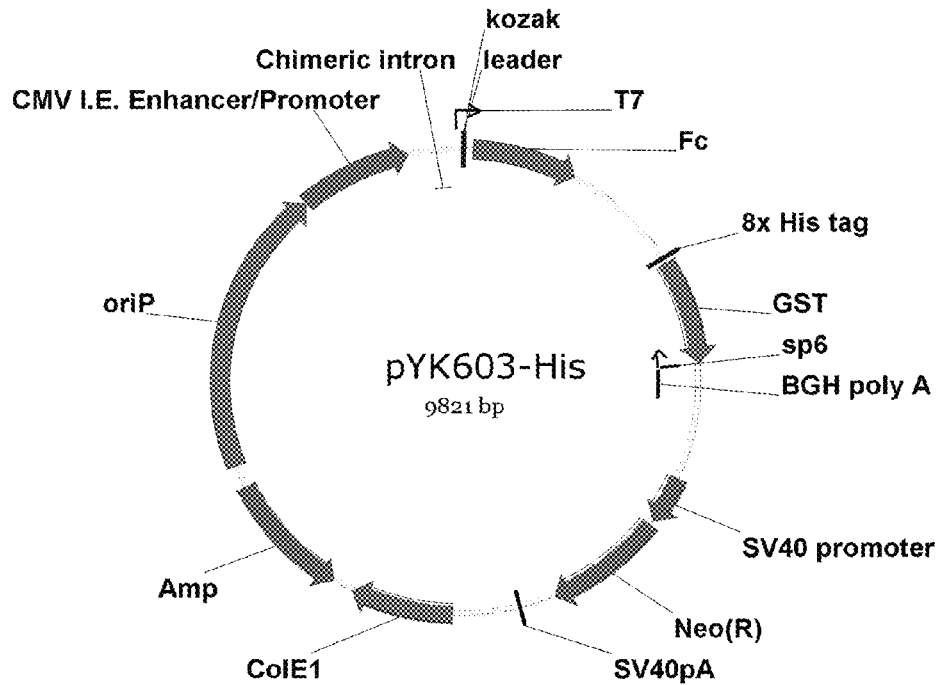

<1-1-2> Subcloning Using pYK602-His and pYK603 pcDNA3.1-VEGF was used as a template by the same manner as in Example 1-1-1 to subclone the VEGF into a pYK602-His vector (FIG. 13b) and a pYK603 vector (FIG. 13c). In addition, the base sequences of the subcloned pYK602-His-VEGF and pyK603-VEGF vectors were identified.

<1-2> Expression and Purification of VEGF Protein
<1-2-1> Identification of VEGF Expression Using pYK602

First, 5×10$^6$ 293E cells were plated in ten 150 mm dishes. The next day, 10 μg of the subcloned pYK602-VEGF vector was treated with PEI (23966: Polysciences, Inc, USA) for transformation. The subsequent day, the dishes were changed with a growth medium (serum-free DMEM) and then a supernatant was obtained every other day. The obtained supernatant was electrophoresized in a 10% SDS-PAGE gel and identified by Western blot.

Specifically, two sheets of 10% SDS-PAGE gel loaded with 20 μl of a supernatant VEGF of the 1st to 7th subcultures were electrophoresized at 100 V for 2 hours and then transferred at 85 V for 2 hours to NC membrane (HATF00010: Millipore, USA). Subsequently, the membrane was blocked overnight at 4° C. in 4% skim milk in TEST. Subsequently, 0.8 mg/Ml of commercially available anti-human Fc-HRP (product No. 31413: Thermo Sci, USA) was diluted at 1:4000 in 4% skim milk in TEST, followed by reaction at room temperature for 1 hour. The mixture was washed five times in a cycle of once every 10 minutes with TEST, followed by development (12145: Intron, USA) to compare the expression levels of protein.

As a result, as shown in FIG. 1, VEGF was expressed until the 7th subculture, and the expression level of VEGF was not generally high while the expression levels of the 2nd and 3rd subcultures were high.

In addition, Protein A column (17-1279-03: GE Healthcare, USA) was used to purify the supernatant at the rate of 1.5 Ml/min. Protein was obtained at a concentration of 0.25 mg/Ml and dialysis of the protein was performed with PBS to confirm that a precipitate was produced.

Thus, the protein was resubcloned into pYK602-His and pYK603 vectors which produced relatively low amounts of precipitation.

<1-2-2> Identification of VEGF Expression Using pYK602-His and pYK603

Transduction was performed on the subcloned pYK602-His-VEGF and pYK603-VEGF vectors by the same manner as in Example 1-2-1, followed by several subcultures to obtain a supernatant.

The supernatants of the 1st and 2nd subcultures of pYK602-VEGF, pYK602-His-VEGF, and pYK603-VEGF vectors were electrophoresized on a 10% SDS-PAGE gel and identified by Western blot. Precipitate productions were also confirmed.

Figure 2:
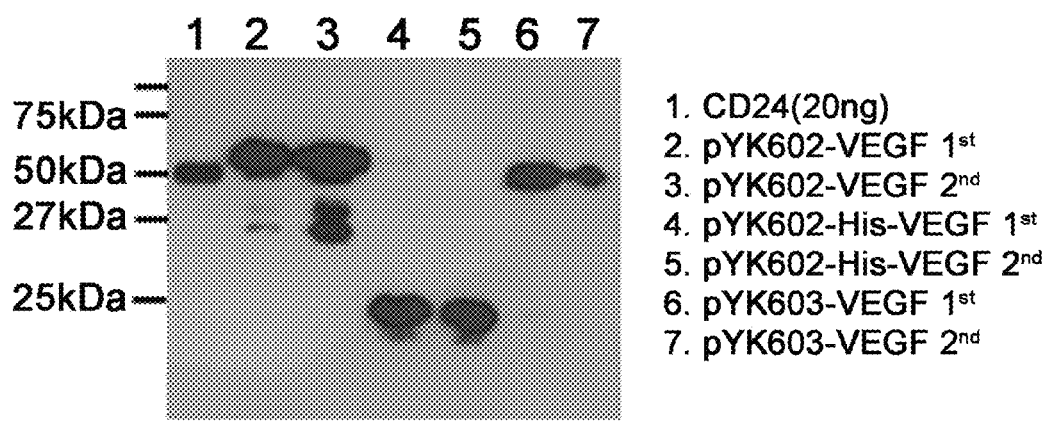
FIG. 2 is a photo illustrating results of VEGF protein expression in pYK602-VEGF, pYK602-His-VEGF, and pYK603-VEGF vectors, compared by Western blot.

As a result, as shown in FIG. 2, the pYK602-VEGF and pYK602-His-VEGF vectors have similar expression levels with relatively low precipitate productions, while the PYK603-VEGF vector has a relatively lower expression level than those of the two.

Thus, the pYK602-His-VEGF vector was ultimately used to express and purify VEGF.

<1-2-3> Identification of pYK602-His-VEGF Vector Expression $5 \times 10^6$ 293E cells were plated in ten 150 mm dishes and transduction of a pYK602-His-VEGF vector was performed, followed by subculture to obtain 300 Ml of supernatants of the 1st to 7th subcultures, respectively. The supernatant was electrophoresized on a 10% SDS-PAGE gel, and then identified by Western blot.

Figure 3:
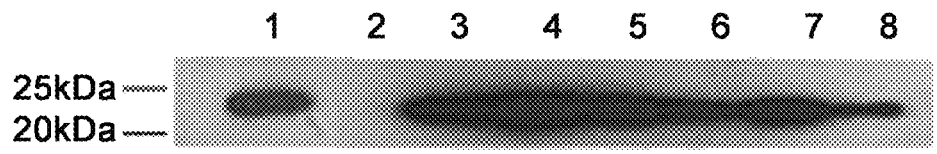
FIG. 3 is a photo illustrating results of VEGF expression in a pYK603-VEGF vector, confirmed by Western blot.

As a result, as shown in FIG. 3, expression levels were highest in supernatants of the 2nd and 3rd subcultures.

<1-2-4> Expression and Purification of VEGF Protein

Each of supernatants of the 2nd and 3rd subcultures was concentrated into 50 Ml, exchanged with 300 Ml of Ni-NTA binding buffer (Qiagen, USA), and then concentrated again into 50 Ml. Ni-NTA beads (1024473, Qiagen, USA) were added into the concentrate, followed by binding at 4° C. for 2 hours to separate and elute the mixture.

Figure 4:
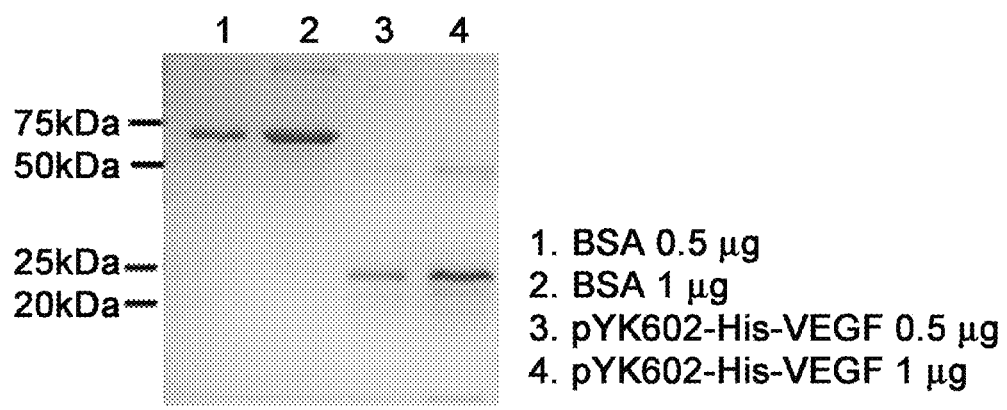
FIG. 4 is a photo illustrating results of a purified VEGF, confirmed by SDS-PAGE.

The elution was introduced into a membrane (10K, 132574: SPECTRAPOR, USA). Buffer exchange was performed at 4° C. in 4 L of PBS solution for 4 hours or more, followed by dialysis in 4 L of pre-cooled PBS solution overnight to change the buffer solution. After the overnight dialysis, the solution was transferred to an e-tube. The concentration of the protein was measured by the Bradford method and identification was performed on a 10% SDS-PAGE gel (FIG. 4).

Example 2

Construction of Library Phage $2.7 \times 10^{10}$ human naive scFv library cells having diversity were incubated in a medium (3 L) containing 2×YTCM [17 g of Tryptone (CONDA, 1612.00), 10 g of yeast extract (CONDA, 1702.00), 5 g of NaCl (Sigma, S7653-5 kg), 34 μg/Ml of chloramphenicol (Sigma, C0857)], 2% glucose (Sigma, G5400), and 5 mM $MgCl_2$ (Sigma, M2393) at 37° C. for 2-3 hours ($OD_{600}$=0.5~0.7). Then, the cells were infected with helper phage, followed by incubation in a medium containing 2×YTCMK [2×YT CM, 70 μg/Ml of Kanamycin (Sigma, K1876), 1 mM IPTG (ELPISBIO, IPTG025)] at 30° C. for 16 hours. The incubated cells was centrifuged (4500 rpm, 15 min, 4° C.) to obtain a supernatant. The supernatant was treated with PEG (Fluka, 81253) and NaCl (Sigma, S7653) until the two reagents became 4% and 3%, respectively. The reactant was centrifuged again (8000 rpm, 20 min, 4° C.). The pellet was dissolved in PBS, which proceeded to centrifugation again (12000 rpm, 10 min, 4° C.). As a result, the supernatant containing library phage was obtained, which was transferred to a new tube and stored at 4° C.

Example 3

Preparation of Monoclonal Antibody

<3-1> Panning Process

An immunosorb tube (Nunc 470319) was coated with 50 μg of VEGF-antigen obtained in Example 1 using 4 Ml of a coating buffer [1.59 g of $Na_2CO_3$ (Sigma, S7795), 2.93 g of $NaHCO_3$ (Sigma, S8875), 0.2 g of $NaN_3$ (Sigma, S2002)] at 4° C. for 16 hours with rotator. Then, the antigen was dissolved in PBS at room temperature for 2 hours, followed by blocking in the immunotube using skim milk [(BD,232100)-4% in 1×PBS]. 2 Ml of library phage constructed in Example 2 was added into the immunotube, followed by reaction at room temperature for 2 hours. The immunotube was washed five times with PEST (0.05%) and twice with PBS. After washing, antigen specific scFV-phage was eluted using 100 mM TEA (Sigma T-0886). E. coli (XL1-blue, stratagene, 200249) was transfected with the eluted phage, followed by amplification. The 2nd and 3rd pannings was performed on the phage amplified at the first panning by the same manner as described above except that washing times with PEST were increased (2nd: 13 times, 3rd: 23 times).

As a result, as shown in Table 1, it was confirmed that colony titer against the antigen was increased at least 1000 times from the 2nd panning.

TABLE 1

| Target antigen | Panning | Initial phage number | Binding phage number |
|---|---|---|---|
| VEGF | $1^{st}$ | $4.2 \times 10^{13}$ | $6.0 \times 10^5$ |
|  | $2^{nd}$ | $2.6 \times 10^{13}$ | $1.3 \times 10^8$ |
|  | $3^{rd}$ | $1.4 \times 10^{13}$ | $1.9 \times 10^8$ |

<3-2> Screening of Phage Antibody by Phage ELISA

<3-2-1> Identification of Panning Results

Cell stocks obtained from the $1^{st}$-$3^{rd}$ pannings and stored as frozen were dissolved in a medium containing 5 Ml of 2×YTCM, 2% glucose, and 5 mM $MgCl_2$ to make $OD_{600}$ as 0.1. Then, the cells were incubated at 37° C. for 2-3 hours ($OD_{600}$=0.5~0.7), which were infected with M1 helper phage. Then, the cells were incubated in a medium containing 2×YTCMK, 5 mM $MgCl_2$ and 1 mM IPTG at 30° C. for 16 hours. At this point, a single phage antibody (#39), which was specifically binding to WW45 antigen associated with a developmental process unrelated to VEGF and constructed by a method in Example of the present invention, was used as a control group. The incubated cells were centrifuged (4500 rpm, 15 min, 4° C.), and the supernatant was transferred to a new tube (1st~3rd panning poly scFv-phage). A 96-well immuno-plate (NUNC 439454) was coated with VEGF antigen (100 ng/well) using a coating buffer at 4° C. for 16 hours, followed by blocking with skim milk dissolved in PBS (4%). Each well of the 96-well immuno-plate was washed with 0.2 Ml of PBS-tween20 (0.05%). 100 μl of the 1st-3rd panning poly ScFV-phage was added into each well, followed by reaction at room temperature for 2 hours. Again, each well was washed four times with 0.2 Ml of PBS-tween20 (0.05%). The secondary antibody anti-M13-HRP (Amersham 27-9421-01) was diluted at 1:2000, followed by reaction at room temperature for 1 hour. The reactant was washed with 0.2 Ml of PBS-tween20 (0.05%). An OPD tablet (Sigma 8787-TAB) was added into a PC buffer [5.1 g of $C_6H_8O_7H_2O$ (Sigma, C0706), 7.3 g of $Na_2HPO_4$ (Sigma, S7907)] to make a substrate solution, which was added into each well by 100 μl/well, followed by color development for 10 minutes. The optical density was measured at 490 nm by using a spectrophotometer (MolecularDevice, USA).

As a result, as shown in FIG. 5, it was confirmed that binding capacities to VEGF antigen were increased from the 2nd polyclonal ScFV-phage pool to reach a saturated state, and values for the tagged His were relatively low.

<3-2-2> Selection of Monoclonal Antibodies

Colonies obtained from a polyclonal antibody group (the 3rd panning) having strong binding capacity were incubated in a 96-deep well plate (Bioneer, 90030) containing 1 Ml of a medium supplemented with 2×YTCM, 2% glucose and 5 mM $MgCl_2$ at 37° C. for 16 hours. 100-200 μl of the solution was incubated in 1 Ml of a medium supplemented with 2×YTCM, 5 mM $MgCl_2$, and 1 mM IPTG, which was loaded in a 96-deep well plate at 37° C. for 2-3 hours, followed by inoculation at an initial $OD_{600}$ value of 0.1. The cells were infected with M1 helper phage (MOI=1:20) and the infected cells were cultured in a medium supplemented with 2×YTCMK, 5 mM $MgCl_2$, and 1 mM IPTG at 30° C. for 16 hours. The cultured cells were centrifuged (4500 rpm, 15 min, 4° C.) and a supernatant was obtained, to which 4% PEG 6000 and 3% NaCl were added. Upon completion of dissolving, reaction was induced in ice for 1 hour. The reactant was centrifuged (8000 rpm, 20 min, 4° C.) and pellet was dissolved in PBS. Centrifugation (12000 rpm, 10 min, 4° C.) was performed again and a supernatant was obtained, from which the 3rd panning monoclonal ScFv phage was obtained. The phage was transferred to a new tube and stored at 4° C.

A 96-well immuno-plate was coated with VEGF antigen (100 ng/well) at 4° C. for 16 hours, followed by blocking with skim milk dissolved in PBS (4%). Each well of the 96-well immuno-plate was washed with 0.2 Ml of PBS-tween20 (0.05%). 100 μl of the 3rd panning monoclonal scFV-phage was added to each well, followed by reaction at room temperature for 2 hours. Each well was washed four times with 0.2 Ml of PBS-tween20 (0.05%). The secondary antibody anti-M13-HRP was diluted at 1:2000, followed by reaction at room temperature for 1 hour. The plate was washed with 0.2 Ml of PBS-tween20 (0.05%), followed by color development. The optical density was measured at 490 nm.

As a result, 50 monoclonal phages having antigen VEGF binding capacity values of 1.5 or more (highlighted in Table 2) were selected.

[Table 2]

| VEGF ≧ 1.5 | VEGF | anti-myc | His | | VEGF | anti-myc | His | | VEGF | anti-myc | His |
|---|---|---|---|---|---|---|---|---|---|---|---|
| A1 | 0.452 | 0.624 | 0.080 | A5 | 1.991 | 1.142 | 0.076 | A9 | 0.954 | 0.121 | 0.058 |
| B1 | 1.561 | 0.692 | 0.055 | B5 | 1.451 | 1.054 | 0.067 | B9 | 1.696 | 0.987 | 0.364 |
| C1 | 0.237 | 0.148 | 0.047 | C5 | 1.927 | 1.134 | 0.091 | C9 | 1.640 | 1.171 | 0.074 |
| D1 | 1.372 | 0.893 | 0.068 | D5 | 0.628 | 1.117 | 0.082 | D9 | 2.091 | 0.771 | 0.065 |
| E1 | 1.594 | 0.484 | 0.049 | E5 | 0.142 | 0.045 | 0.059 | E9 | 2.162 | 0.705 | 0.066 |
| F1 | 1.494 | 0.962 | 0.049 | F5 | 1.759 | 0.983 | 0.113 | F9 | 2.077 | 1.525 | 0.096 |
| G1 | 1.909 | 1.088 | 0.065 | G5 | 0.607 | 0.336 | 0.137 | G9 | 1.852 | 1.091 | 0.089 |
| H1 | 0.832 | 0.598 | 0.520 | H5 | 1.312 | 1.160 | 0.069 | H9 | 1.550 | 0.889 | 0.156 |
| A2 | 1.663 | 0.313 | 0.058 | A6 | 1.035 | 1.202 | 0.083 | A10 | 1.811 | 1.110 | 0.061 |
| B2 | 1.504 | 0.945 | 0.062 | B6 | 1.148 | 1.143 | 0.061 | B10 | 0.553 | 0.335 | 0.062 |
| C2 | 1.153 | 0.953 | 0.051 | C6 | 0.291 | 0.118 | 0.074 | C10 | 1.676 | 1.005 | 0.063 |
| D2 | 1.117 | 0.832 | 0.056 | D6 | 1.544 | 0.807 | 0.075 | D10 | 1.711 | 0.849 | 0.055 |
| E2 | 1.825 | 0.566 | 0.068 | E6 | 1.454 | 1.215 | 0.083 | E10 | 1.661 | 1.401 | 0.084 |
| F2 | 1.517 | 0.778 | 0.064 | F6 | 2.003 | 0.637 | 0.063 | F10 | 1.711 | 0.862 | 0.071 |
| G2 | 0.724 | 0.167 | 0.065 | G6 | 1.763 | 0.975 | 0.050 | G10 | 1.721 | 0.661 | 0.060 |
| H2 | 1.213 | 0.928 | 0.049 | H6 | 1.710 | 0.778 | 0.063 | H10 | 1.719 | 1.152 | 0.072 |
| A3 | 0.581 | 0.134 | 0.056 | A7 | 1.910 | 1.124 | 0.056 | A11 | 1.265 | 1.312 | 0.068 |
| B3 | 1.509 | 0.915 | 0.066 | B7 | 0.180 | 0.278 | 0.059 | B11 | 0.440 | 0.099 | 0.062 |
| C3 | 1.399 | 1.070 | 0.072 | C7 | 0.436 | 0.224 | 0.054 | C11 | 1.719 | 1.484 | 0.069 |
| D3 | 1.607 | 0.644 | 0.062 | D7 | 1.999 | 0.684 | 0.063 | D11 | 0.047 | 0.032 | 0.049 |
| E3 | 1.602 | 1.040 | 0.078 | E7 | 2.000 | 0.750 | 0.066 | E11 | 0.429 | 0.138 | 0.052 |
| F3 | 1.332 | 0.911 | 0.062 | F7 | 0.205 | 1.457 | 0.343 | F11 | 1.393 | 1.142 | 0.058 |
| G3 | 1.877 | 0.950 | 0.071 | G7 | 1.417 | 1.198 | 0.096 | G11 | 2.045 | 1.207 | 0.100 |
| H3 | 1.765 | 0.830 | 0.058 | H7 | 1.780 | 1.420 | 0.185 | H11 | 0.534 | 0.483 | 0.072 |
| A4 | 1.699 | 0.904 | 0.055 | A8 | 0.992 | 1.008 | 0.066 | A12 | 0.049 | 0.164 | 0.063 |
| B4 | 0.045 | 0.051 | 0.054 | B8 | 1.472 | 1.201 | 0.092 | B12 | 1.686 | 1.288 | 0.073 |
| C4 | 1.419 | 0.969 | 0.061 | C8 | 1.688 | 0.862 | 0.061 | C12 | 1.688 | 1.390 | 0.084 |
| D4 | 0.725 | 0.910 | 0.066 | D8 | 1.233 | 0.962 | 0.087 | D12 | 1.849 | 0.833 | 0.054 |
| E4 | 1.307 | 0.959 | 0.054 | E8 | 1.650 | 1.314 | 0.065 | E12 | 2.139 | 1.012 | 0.064 |
| F4 | 1.153 | 0.915 | 0.061 | F8 | 1.452 | 1.039 | 0.072 | F12 | 2.109 | 0.868 | 0.048 |
| G4 | 1.270 | 0.844 | 0.060 | G8 | 1.433 | 1.264 | 0.089 | G12 | 2.142 | 1.752 | 0.104 |
| H4 | 1.469 | 0.623 | 0.063 | H8 | 1.486 | 0.620 | 0.064 | H12 | 2.165 | 1.319 | 0.107 |

<3-3> Identification of Monoclonal Phages and Examination Thereof

<3-3-1> Verification by Fingerprinting

1 μl of the ten monoclonal cells firstly selected, 0.2 μl of Taq DNA polymerase (Gendocs, Korea) (5 U/ul), 50 p/μl of each forward primer (pelB5, SEQ. ID. No. 125: 5'-CTA-GATAACGAGGGCAAATCATG-3') and reverse primer (cla3, SEQ. ID. No. 126: 5'-CGTCACCAATGAAACCATC- 3'), 3 μl of 10× buffer, 0.6 μl of 10 mM dNTP mix, and 24.8 μl of distilled water were mixed to perform a colony PCR (iCycler iQ, BIO-RAD). PCR conditions are as shown in Table 3.

TABLE 3

| Temperature | Time | Cycle |
|---|---|---|
| 95° C. | 5 min | |
| 95° C. | 30 sec | 30 |
| 56° C. | 30 sec | |
| 72° C. | 1 min | |
| 72° C. | 10 min | |
| 4° C. | | |

The colony PCR product was identified on a 1% agarose gel (Seakem LE, CAMERES 50004). 0.2 μl of BstNI (Roche11288075001, 10 U/μl) was added to perform a reaction at 37° C. for 2-3 hours. Reaction conditions are as shown in Table 4. The fragmented product was identified on an 8% DNA polyacrylamide gel.

TABLE 4

| 10X Buffer | 3 μl |
|---|---|
| colony PCR product | 10 μl |
| BstNI (10 U/μl) | 0.2 μl |
| Distilled water | 16.8 μl |

The colony PCR product was identified on a 1% agarose gel (Seakem LE, CAMERES 50004). 0.2 μl of BstNI (Roche11288075001, 10 U/μl) was taken to perform a reaction at 37° C. for 2-3 hours. Reaction conditions are as shown in Table 5. The fragmented product was identified on an 8% DNA polyacrylamide gel.

As a result, as shown in Table 6, fragments of monoclonal phage antibodies digested by BstNI were proved to have diversity.

<3-3-2> Verification by Base Sequence Analysis 50 kinds of the monoclonal phages were incubated in a medium (5 ml) supplemented with 2×YTCM, 2% glucose, and 5 mM $MgCl_2$ at 37° C. for 16 hours. A DNA purification kit (Nuclogen 5112) was used for the incubated monoclones to obtain a DNA, and then sequencing was performed by using a pelB5 primer of SEQ ID No. 125 (Solgent, Korea).

As a result, as shown in Table 5 and FIGS. 7 & 8, CDR regions of $V_H$ and $V_L$ of the selected antibody were identified.

Similarity between the antibody and germ line antibody group was investigated by Ig BLAST program of NCBI (//www.ncbi.nlm.nih.gov/igblast/). As a result, 14 kinds of VEGF specific phage antibodies were obtained, and the result was summarized and presented in Table 6. Specifically, the heavy chain exhibited 89.9% to 96% homology with human germ cell family sequence, while the light chain exhibited 89.2% to 97% homology. In addition, polypeptides used in CDR3 of heavy and light chains of each human antibody were analyzed, and it was confirmed that their sequences were different.

TABLE 5

| Group | Clone name | Heavy Chain | | | Light Chain | | |
|---|---|---|---|---|---|---|---|
| | | CDR1 | CDR2 | CDR3 | CDR1 | CDR2 | CDR3 |
| 1 | A4 | DYAMH SEQ ID No. 5 | FINEDGGNIYYGDS VKG SEQ ID No. 18 | EPSGSLTFDY SEQ ID No. 31 | RASQTISSYLN SEQ ID No. 57 | AASRLQS SEQ ID No. 70 | QQSYSTPYT SEQ ID No. 83 |
| 2 | B12 | SYAIS SEQ ID No. 6 | GIIPIFGTANYAQK FQG SEQ ID No. 19 | DRSGYTAMDY SEQ ID No. 32 | RASQGISSYLA SEQ ID No. 58 | AASTLQS SEQ ID No. 71 | QQGHTTPYT SEQ ID No. 84 |
| 3 | C11 | SDAIS SEQ ID No. 7 | GVIPIFATTTYAQG FQG SEQ ID No. 20 | GQMDRGGGLDP SEQ ID No. 33 | RASQGIGNYLN SEQ ID No. 59 | AASSLQR SEQ ID No. 72 | QQSYTTPYS SEQ ID No. 85 |
| 4 | C12 | SYGMN SEQ ID No. 8 | SISSSSSSIHYADS VKG SEQ ID No. 21 | LGPYDAFDF SEQ ID No. 34 | PGGTSNIDSKY VH SEQ ID No. 60 | RNDQRPS SEQ ID No. 73 | QSYDTSLSA PYV SEQ ID No. 86 |
| 5 | C5 | SYSMH SEQ ID No. 9 | GISYDGSSKQFGDS VKG SEQ ID No. 22 | DGVPGHSYGIG MDV SEQ ID No. 35 | RASQGISSWLA SEQ ID No. 61 | AASILQT SEQ ID No. 74 | QQANSFPYT SEQ ID No. 87 |
| 6 | C9 | SYAMH SEQ ID No. 10 | VISYDGSNKYYADS VKG SEQ ID No. 23 | DVDSWSQGWFPH SEQ ID No. 36 | RASQTISTFVN SEQ ID No. 62 | SASSLQS SEQ ID No. 75 | QQNYSTPLT SEQ ID No. 88 |
| 7 | D12 | EYAMH SEQ ID No. 11 | LISGDDYNTFYADS VKG SEQ ID No. 24 | DAGPAGGGGLDH SEQ ID No. 37 | RTSQTITNFLN SEQ ID No. 63 | GASSLQS SEQ ID No. 76 | QQSHGTPYT SEQ ID No. 89 |
| 8 | E9 | TSGVA VG SEQ ID No. 12 | LIYWDNDKRYSPSL KN SEQ ID No. 25 | GDGWLFDF SEQ ID No. 38 | TGSNSNIGAGH DVH SEQ ID No. 64 | GNTNRAS SEQ ID No. 77 | QSYDNSLSG YV SEQ ID No. 90 |

TABLE 5-continued

| Group | Clone name | Heavy Chain CDR1 | CDR2 | CDR3 | Light Chain CDR1 | CDR2 | CDR3 |
|---|---|---|---|---|---|---|---|
| 9 | F2 | SYAMS SEQ ID No. 13 | YISSSGHDIYYADP VKG SEQ ID No. 26 | DKLATPGAFDI SEQ ID No. 39 | RASQSISNWLA SEQ ID No. 65 | EASSLES SEQ ID No. 78 | QQSHGTPYT SEQ ID No. 89 |
| 10 | F6 | TSGVAVG SEQ ID No. 12 | LIYWDNDKRYSPSL KN SEQ ID No. 25 | GDGWLFDF SEQ ID No. 38 | TGSNSNIGAGH DVH SEQ ID No. 64 | GNTNRAS SEQ ID No. 77 | QSYDNSLSGYV SEQ ID No. 90 |
| 11 | F9 | TTAIT SEQ ID No. 14 | WITPFNGNTFYAQK FQD SEQ ID No. 27 | SQAAELGTGAFDI SEQ ID No. 40 | SGSYSNIGTNYVY SEQ ID No. 66 | KNTQRPS SEQ ID No. 79 | SAWDDSLSAVL SEQ ID No. 91 |
| 12 | G12 | NYAIS SEQ ID No. 15 | RIIPIYGTPTYAQK FRD SEQ ID No. 28 | ERSFWNWFAP SEQ ID No. 41 | TGSSSNIGAGY DVH SEQ ID No. 67 | GNNNRPS SEQ ID No. 80 | QSYDSRLGVV SEQ ID No. 92 |
| 13 | G9 | TYALH SEQ ID No. 16 | VISHDGTTDYYRDS VKG SEQ ID No. 29 | DGSGYFFDY SEQ ID No. 42 | TGSSSDVGGYN YVS SEQ ID No. 68 | DVTKRPS SEQ ID No. 81 | SSYSSSTFYV SEQ ID No. 93 |
| 14 | H7 | KYGMH SEQ ID No. 17 | FIWFDGSNKFYADS VKG SEQ ID No. 30 | DRDYYGSGPLDY SEQ ID No. 43 | RASQRIATYLH SEQ ID No. 69 | AASSLQS SEQ ID No. 82 | QQSYSTPYT SEQ ID No. 83 |

[Table 6]

| Clone name | VH | Identities | VL | Identities | VH(CDR-a.a seq) | Vk(CDR-a.a seq) | VEGF | anti-myc | His | Ratio | Group |
|---|---|---|---|---|---|---|---|---|---|---|---|
| A4 | VH3-43 | 93.2(272/292) | O12 | 97.2(276/284) | EPSGSLTFDY | QQSYSTPYT | 1.699 | 0.904 | 0.055 | 1.880 | 1 |
| B12 | VH1-69 | 99.3(294/296) | O12 | 93.3(265/284) | DRSGYTAMDY | QQGHTTPYT | 1.686 | 1.288 | 0.073 | 1.309 | 2 |
| C11 | VH1-69 | 90.8(268/295) | O12 | 93.3(265/284) | GQMDRGGGLDP | QQSYTTPYS | 1.719 | 1.484 | 0.069 | 1.159 | 3 |
| C12 | VH3-21 | 95.6(280/293) | V1-17 | 87.4(250/286) | LGPYDAFDF | QSYDTSLSAPYV | 1.688 | 1.390 | 0.084 | 1.214 | 4 |
| C5 | VH3-30 | 94.3(279/296) | L5 | 97.5(277/284) | DGVPGHSYGIGMDV | QQANSFPYT | 1.927 | 1.134 | 0.091 | 1.700 | 5 |
| C9 | VH3-30 | 96.6(286/296) | O2 | 93.4(267/286) | DVDSWSQGWFPH | QQNYSTPLT | 1.640 | 1.171 | 0.074 | 1.400 | 6 |
| D12 | VH3-43 | 91.8(269/293) | O12 | 94.0(267/284) | DAGPAGGGGLDH | QQSHGTPYT | 1.849 | 0.833 | 0.054 | 2.221 | 7 |
| D9 | VH2-5 | 94.3(280/297) | V1-13 | 93.2(272/292) | GDGWLFDF | QSYDNSLSGYV | 2.091 | 0.771 | 0.065 | 2.712 | 8 |
| E2 | VH2-5 | 94.3(280/297) | V1-13 | 93.2(272/292) | GDGWLFDF | QSYDNSLSGYV | 1.825 | 0.566 | 0.068 | 3.226 | 8 |
| E7 | VH2-5 | 94.3(280/297) | V1-13 | 93.2(272/292) | GDGWLFDF | QSYDNSLSGYV | 2.000 | 0.750 | 0.066 | 2.668 | 8 |
| E9 | VH2-5 | 94.3(280/297) | V1-13 | 93.2(272/292) | GDGWLFDF | QSYDNSLSGYV | 2.162 | 0.705 | 0.066 | 3.069 | 8 |
| F2 | VH3-11 | 89.9(266/296) | L12a | 94.1(254/270) | DKLATPGAFDI | QQSHGTPYT | 1.517 | 0.778 | 0.064 | 1.949 | 9 |
| F6 | VH2-5 | 94.3(280/297) | V1-13 | 93.2(272/292) | GDGWLFDF | QSYDNSLSGYV | 2.003 | 0.637 | 0.063 | 3.143 | 10 |
| F9 | VH1-45 | 90.5(268/296) | V1-17 | 89.2(255/286) | SQAAELGTGAFDI | SAWDDSLSAVL | 2.077 | 1.525 | 0.096 | 1.362 | 11 |
| G12 | VH1-69 | 94.3(279/296) | V1-13 | 96.5(279/289) | ERSFWNWFAP | QSYDSRLGVV | 2.142 | 1.752 | 0.104 | 1.222 | 12 |
| G9 | VH3-30 | 91.6(271/296) | V1-4 | 94.3(264/280) | DGSGYFFDY | SSYSSSTFYV | 1.852 | 1.091 | 0.089 | 1.698 | 13 |
| H7 | VH3-33 | 94.5(276/292) | O12 | 97.5(278/285) | DRDYYGSGPLDY | QQSYSTPYT | 1.780 | 1.420 | 0.185 | 1.253 | 14 |

Example 4

Analysis of Characteristics of Human Antibody Against VEGF

<4-1> Measurement of Binding Capacity

In order to measure binding capacities to VEGF of 14 kinds of monoclonal phage antibodies selected in Example 3, each binding capacity was measured by the manner as in Example 3-2.

As a result, as shown in FIGS. 9a & 9b, binding capacities of 14 kinds of the monoclonal phage antibodies were in the order of G12>D12>E9>F6>H7>C5>B12>G9>F9>C11>F2>A4>C9>C12.

<4-2> Analysis of Whole IgG Conversion

In order to convert monoclonal phage antibodies against VEGF from phage to whole IgG vector, 1 µl of heavy chain monoclonal DNA, 10 pmole/µl of each heavy chain forward primer and heavy chain reverse primer in Table 7, 5 µl of 10× buffer, 1 µl of 10 mM dNTP mix, 0.5 µl of pfu DNA polymerase (Solgent, 2.5 U/µl), and distilled water (iCycler iQ, BIO-RAD) were mixed to perform a colony PCR (iCycler iQ, BIO-RAD). In addition, colony PCR was performed on light chain by the same manner by using light chain forward primer and reverse primer in Table 7.

TABLE 7

| Clone name | Heavy Chain Forward primer (Sfi I) | Reverse primer (NheI) | Light Chain Forward primer (Sfi I) | | Reverse primer (Bgl II) | |
|---|---|---|---|---|---|---|
| A4 | NATVH7-1 SEQ ID No. 107 | TTGGTGGCCACAGC GGCCGATGTCCACT CGCAGATGCAGCTG GTGGAGTC | NATJH-ALL SEQ ID No. 114 | GAGGAGG CTAGCTGA GGAGACG GTGA | NATVK 1-1 SEQ ID No. 115 | TTGGTGGCCACAGC GGCCGATGTCCACT CGGACATCCAGATG ACCCAGTC | NATJK-R7 SEQ ID No. 119 | GAGGAGAGA TCTTTTGATA TCCACCTTGGT |
| C5 | NATVH3-1 SEQ ID No. 108 | TTGGTGGCCACAGC GGCCGATGTCCACT CGCAGGTGCAGCTG GTGGAGTC | | | | | NATJK-R1 SEQ ID No. 120 | GAGGAGAGA TCTTTTTGAT CTCTACCTTG GT |
| C11 | NATVH1-2 SEQ ID No. 109 | TTGGTGGCCACAGC GGCCGATGTCCACT CGCAGATGCAGCTG GTGGAGTC | | | | | NATJK-R2 SEQ ID No. 121 | GAGGAGAGA TCTTTTTGAT CTCCACTTTG GT |
| C12 | NATVH7-1 SEQ ID No. 107 | TTGGTGGCCACAGC GGCCGATGTCCACT CGCAGATGCAGCTG GTGGAGTC | | | NATVL10 SEQ ID No. 116 | TTGGTGGCCACAGC GGCCGATGTCCACT CGCAGCTCGTGCTG ACTCAGCC | NATJL1-R SEQ ID No. 122 | GAGGAGAGA TCTTTAGGAC GGTGACCTT GGTCCC |
| E9 | NATVH2-1 SEQ ID No. 110 | TTGGTGGCCACAGC GGCCGATGTCCACT CGCAGGTCACCTTG AAGGAGTC | | | NATVL2 SEQ ID No. 117 | TTGGTGGCCACAGC GGCCGATGTCCACT CGCAGCCTGTGCTG ACTCAGCC | | |
| F2 | NATVH3-2 SEQ ID No. 111 | TTGGTGGCCACAGC GGCCGATGTCCACT CGCAGGTGCAGCTG GTGGAGTC | | | NATVK1-1 SEQ ID No. 115 | TTGGTGGCCACAGC GGCCGATGTCCACT CGGACATCCAGATG ACCCAGTC | NATJK-R5 SEQ ID No. 123 | GAGGAGAGA TCTTTTTGAT TTCCAGCTTG GT |
| F6 | NATVH2-1 SEQ ID No. 110 | TTGGTGGCCACAGC GGCCGATGTCCACT CGCAGGTCACCTTG AAGGAGTC | | | NATVL2 SEQ ID No. 117 | TTGGTGGCCACAGC GGCCGATGTCCACT CGCAGCCTGTGCTG ACTCAGCC | NATJL1-R SEQ ID No. 122 | GAGGAGAGA TCTTTAGGAC GGTGACCTT GGTCCC |
| G9 | NATVH3-2 SEQ ID No. 111 | TTGGTGGCCACAGC GGCCGATGTCCACT CGCAGGTGCAGCTG GTGGAGTC | | | NATVL9 SEQ ID No. 118 | TTGGTGGCCACAGC GGCCGATGTCCACT CGAATTTTATGCTGA CTCAGCC | | |
| G12 | NATVH1-1 SEQ ID No. 112 | TTGGTGGCCACAGC GGCCGATGTCCACT CGCAGGTGCAGCTG GTGCAGTC | | | NATVL2 SEQ ID No. 117 | TTGGTGGCCACAGC GGCCGATGTCCACT CGCAGCCTGTGCTG ACTCAGCC | NATJL2-R SEQ ID No. 124 | GAGGAGAGA TCTTTAGGAC GGTCAGCTT GGTCCC |
| H7 | NATVH7-2 SEQ ID No. 113 | TTGGTGGCCACAGC GGCCGATGTCCACT CGCAGATGCAGCTG GTAAAGTC | NATJH-ALL SEQ ID No. 114 | GAGGAGG CTAGCTGA GGAGACG GTGA | NATVK1-1 SEQ ID No. 115 | TTGGTGGCCACAGC GGCCGATGTCCACT CGGACATCCAGATG ACCCAGTC | NATJK-R1 SEQ ID No. 120 | GAGGAGAGA TCTTTTTGAT CTCTACCTTG GT |
| D12 | NATVH7-1 SEQ ID No. 107 | TTGGTGGCCACAGC GGCCGATGTCCACT CGCAGATGCAGCTG GTGGAGTC | | | | | NATJK-R5 SEQ ID No. 123 | GAGGAGAGA TCTTTTTGAT TTCCAGCTTG GT |
| C9 | NATVH7-3 SEQ ID No. 128 | TTGGTGGCCACAGC GGCCGATGTCCACT CGCAGGTGCAGCTG GTAAAGTC | | | NATVK1-1 SEQ ID No. 115 | TTGGTGGCCACAGC GGCCGATGTCCACT CGGACATCCAGATG ACCCAGTC | NATJK-R3 SEQ ID No. 129 | GAGGAGAGA TCTTTTGATC TCCAGTCGT GT |
| F9 | | | | | NATVL10 SEQ ID No. 116 | TTGGTGGCCACAGC GGCCGATGTCCACT CGCAGCTCGTGCTG ACTCAGCC | NATJL2-R SEQ ID No. 124 | GAGGAGAGA TCTTAGGAC GGTCAGCTT GGTCCC |
| B12 | NATVH1-1 SEQ ID No. 112 | TTGGTGGCCACAGC GGCCGATGTCCACT CGCAGGTGCAGCTG GTGCAGTC | | | NATVK1-1 SEQ ID No. 115 | TTGGTGGCCACAGC GGCCGATGTCCACT CGGACATCCAGATG ACCCAGTC | NATJK-R5 SEQ ID No. 123 | GAGGAGAGA TCTTTTGATT TCCAGCTTG GT |

The heavy chain gene obtained through PCR was purified with DNA-gel extraction kit (Qiagen). 1 µl of pNATAB H vector (FIG. 12a) (10 ng), 15 µl of heavy chain (100-200 ng), 2 µl of 10× buffer, 1 µl of Ligase (1 U/µl), and distilled water were mixed with the gene and the mixture was left still at room temperature for 1-2 hours for linkage to the vector. The vector was left still in ice for 30 minutes along with a cell for transformation (XL1-blue), followed by heat shock at 42° C. for 90 sec for transfection. It was again left still in ice for 5 minutes and 1 Ml of LB medium was injected, followed by incubation at 37° C. for 1 hour. The mixture was smeared in LB Amp liquid medium, followed by incubation at 37° C. for 16 hours. Single colony was inoculated into 5 Ml of LB Amp liquid medium, followed by incubation at 37° C. for 16 hours. A DNA-prep kit (Nuclogen) was used for the medium to extract a DNA.

In addition, pNATAB L vector (FIG. 12b) was used by the same manner to extract a DNA of the light chain.

Sequencing of the obtained DNA was performed by using a CMV-proF primer (SEQ ID No. 127: AAA TGG GCG GTA GGC GTG) (Solgent).

As a result, it was confirmed that the sequences of heavy and light chains of the 14 clone phages against VEGF converted into whole IgG were identical to those of the phage antibodies.

<4-3> Verification of Whole IgG

40 μg of PEI and 10 μg of each antibody heavy chain DNA and light chain DNA in the whole form were added into 293E cells (Invitrogen) for co-transfection to obtain a supernatant, which was identified by Western blot. Normal human IgG (Jacson Lab) was used as a control group.

As a result, it was confirmed that it was successfully converted into whole IgG form compared to a control group.

<4-4> Identification of Neutralizing Capacities of Anti-VEGF Antibodies Through Analysis of Inhibition of Tube Formation A monolayer of HUVEC cell (C2517A: Lonza), a human umbilical vein endothelial cell of about 80% confluence, was exchanged with EBM-2 (CC3156, Cambrex) supplemented with 1% FBS and a starvation state was made in a 37° C./5% $CO_2$ incubator for 4 hours. Subsequently, the medium was treated with trypsin to collect and suspend the cells in a starvation medium at $3 \times 10^5$/Ml. 100 μl of cell suspension, 150 μl of the purified human VEGF Ab solution of the present invention (VEGF Ab is diluted with a starvation medium and treated at a concentration of 4 μg/Ml), and a normal human IgG as a negative control group were treated at a concentration of 4 μg/Ml, or Avastin™ (Genetech) as a positive control group was treated at a concentration of 4 μg/Ml, followed by pre-incubation at 37° C. for 1 hour. During the pre-incubation, 200 μl of Matrigel (354230: BD Bio-Science, USA) cooled with ice was introduced into a 24-well plate, and then homogenization was performed in a 37° C./5% $CO_2$ incubator for 30 minutes. Recombinant human VEGF was added into a mixture of the cells for which reaction had been completed and Ab at a concentration of 20 ng/Ml and placed onto the Matrigel, followed by incubation in a 37° C./5% $CO_2$ incubator. In order to observe a tube formation after incubation for 16 hours, 500 μl of 3.7% paraformaldehyde was introduced into the incubator, followed by immobilization at room temperature for 30 minutes. Next, the mixture was stained with 500 μl of 0.01% crystal violet/100 mM NaBorate and dried to observe a tube formation under a magnification of about 100×.

As a result, as shown in FIG. 10, it was observed that the purified VEGF Ab exhibited an obvious inhibition of tube formation, compared to a positive control group.

It was observed that the three antibodies except for C5 among E9, F6, G12, and C5 all inhibited a capillary-like tube formation of HUVEC cells, induced by VEGF significantly, and thus neutralizing capacities of human antibodies against VEGF of the present invention were identified.

<4-5> Identification of Cross Reactivity of Anti-VEGF Antibodies in a Mouse

In addition, ELISA was performed to see if each antibody could have cross-reactivity not only with human VEGF, but also with mouse VEGF. Two 96-well immuno-plates were coated with (50 ng/well) of each recombinant human VEGF (293-VE, R&D systems, USA) and recombinant mouse VEGF (493-MV, R&D systems, USA) using a coating buffer at 4° C. for 16 hours, followed by blocking with skim milk dissolved in PBS (4%). Each well of the 96-well immuno-plate was washed with 0.2 Ml of PBS-tween20 (0.05%). E9, F6, and G12 monoclonal antibodies were diluted gradually from 333 nM by 1/3, and each of 100 μl of the diluted monoclonal antibodies was added into each well of the two antigen coated plates with Avastin™ as a control group at room temperature for 2 hours. Each well was washed four times with 0.2 Ml of PBS-tween20 (0.05%). The secondary antibody anti-human Fc-HRP was diluted at 1:3000, followed by reaction at room temperature for 30 minutes. The reactant was washed with 0.2 Ml of PBS-tween20 (0.05%). An OPD tablet was added into a PC buffer to make a substrate solution, which was added into each well by 100 μl/well, followed by color development for 5 minutes. The optical density was measured at 490 nm by using a spectrophotometer.

Graphpad prism ver.4 software (CA 92037: Graphpad Software Inc., USA) was used to analyze the ELISA results.

As a result, E9, F6, and G12 monoclonal antibodies, showing neutralizing capacities similar to that of Avastin™ in FIG. 10, all exhibited strong affinities for mouse VEGF similar to those for human VEGF, leading to a cross reaction (Table 8 and FIG. 11). The F6 antibody showing the strongest neutralizing capacity consistently exhibited an about 2-fold lower $K_D$ value than that of Avastin™. Thus, the probabilities are certainly high that the VEGF neutralizing human antibody of the present invention is different from the conventional anti-cancer agent Avastin™ in terms of epitope.

TABLE 8

| | Ab | | | |
|---|---|---|---|---|
| Ag | E9 ($R^2$) | F6 ($R^2$) | G12 ($R^2$) | Avastin ($R^2$) |
| mVEGF | $6.5 \times 10^{-11}$ (0.99) | $3.4 \times 10^{-11}$ (0.98) | $2.6 \times 10^{-10}$ (0.99) | N.D |
| hVEGF | $5.1 \times 10^{-11}$ (0.99) | $2.8 \times 10^{-11}$ (0.97) | $2.4 \times 10^{-11}$ (0.99) | $5.9 \times 10^{-11}$ (0.87) |

TABLE 9

| | | nM | | | | | | | | | | | |
|---|---|---|---|---|---|---|---|---|---|---|---|---|---|
| Ag | Ab | 50 | 25 | 12.5 | 6.25 | 3.13 | 1.56 | 0.78 | 0.39 | 0.20 | 0.10 | 0.049 | 0.024 |
| mVEGF | E9 | 2.4569 | 2.2777 | 2.3099 | 2.0685 | 2.3331 | 2.2543 | 2.2338 | 2.0163 | 1.7289 | 1.4132 | 0.9682 | 0.6036 |
| | F6 | 2.3555 | 2.3232 | 2.3049 | 2.3041 | 2.1922 | 2.1811 | 2.1885 | 2.1425 | 2.1341 | 1.7251 | 1.3023 | 0.8829 |
| | G12 | 2.4617 | 2.302 | 2.2623 | 2.166 | 2.1757 | 2.0375 | 1.7438 | 1.3811 | 0.9585 | 0.721 | 0.3959 | 2.159 |
| | Avastin | 0.6949 | 0.1074 | 0.1041 | 0.0424 | 0.0489 | 0.0455 | 0.0438 | 0.0569 | 0.0433 | 0.147 | 0.0687 | 0.0467 Not bolgG (50 nM) |
| VEGF | E9 | 2.5106 | 2.4445 | 2.4182 | 2.3279 | 2.4466 | 2.3016 | 2.1899 | 2.0938 | 1.9197 | 1.7033 | 1.1523 | 0.6822 |
| | F6 | 2.5407 | 2.3745 | 2.3649 | 2.3101 | 2.2942 | 2.2765 | 2.2617 | 2.1785 | 2.1829 | 1.8819 | 1.5032 | 0.9789 |
| | G12 | 2.5305 | 2.4915 | 2.2875 | 2.251 | 2.0766 | 1.9873 | 1.8751 | 1.4892 | 0.9924 | 0.7689 | 0.4748 | 0.226 |
| | Avastin | 2.5166 | 2.4828 | 2.4441 | 2.4332 | 2.4087 | 2.3666 | 2.1938 | 2.187 | 2.0882 | 1.7951 | 1.3556 | 0.052 Not bolgG (50 nM) |

Example 5

Performance of LC Shuffling of VEGF F6 and G12 Monoclonal Antibodies

<5-1> Construction of LC Shuffling Library

Heavy chain portions from scFv-phages of the monoclonal F6 and G12 obtained in Example 3 were treated with SfiI at about 50° C., to which SfiI was added every 2 hours, and this process was repeated three times for gel elution. pYG100, a library plasmid, was also treated with SfiI at about 50° C. for about 4 hours, treated with SfiI once again, and restricted overnight for gel elution. Concentrations of heavy chain fragments of the monoclonal F6 and G12 digested and the concentration of vector were measured, followed by ligating with 10 units of ligase at a molar ratio of vector: heavy chain fragments=1:5 prepared for a total solution at 1 μg/100 μl at room temperature for about 2 to about 4 hours. A ligated product was concentrated with ethanol, followed by electroporation of 20 μl of the ligated product in distilled water with XL1-BLUE cells at $1\times10^9$ cells/100 μl for transduction. Incubation of the product was performed at about 37° C. overnight, followed by storage in 500 μl of 15% glycerol 2XYT at about −70° C. A titer measurement resulted in a diversity of $2.1\times10^6$.

<5-2> Construction of LC Shuffling Library Phage

A library phage was constructed for human naïve VEGF F6 & G12 LC shuffling scFv library cells having a diversity of $2.1\times10^6$ prepared in Example 5-1 by the same manner as described above in Example 2.

<5-3> Construction of LC Shuffling Monoclonal Antibodies

A phage panning was conducted using 50 μg of the purified VEGF antigen obtained in Example 1 and 2 Ml of the library phage constructed in Example 5-2 by the same manner as in Example 3, a panning result was confirmed, a monoclonal antibody selected, and a monoclonal phage was classified and examined.

As a result of the panning, it was confirmed that a high titer was shown from the 1st panning as indicated in Table 10 and colony titer of a phage against the antigen at the 2nd panning was increased at least 5 times.

TABLE 10

| Target antigen | Panning | Initial phage number | Binding phage number |
|---|---|---|---|
| VEGF | $1^{st}$ | $2.0 \times 10^{13}$ | $2.2 \times 10^5$ |
|  | $2^{nd}$ | $1.2 \times 10^{14}$ | $4.6 \times 10^9$ |

Figure 14:
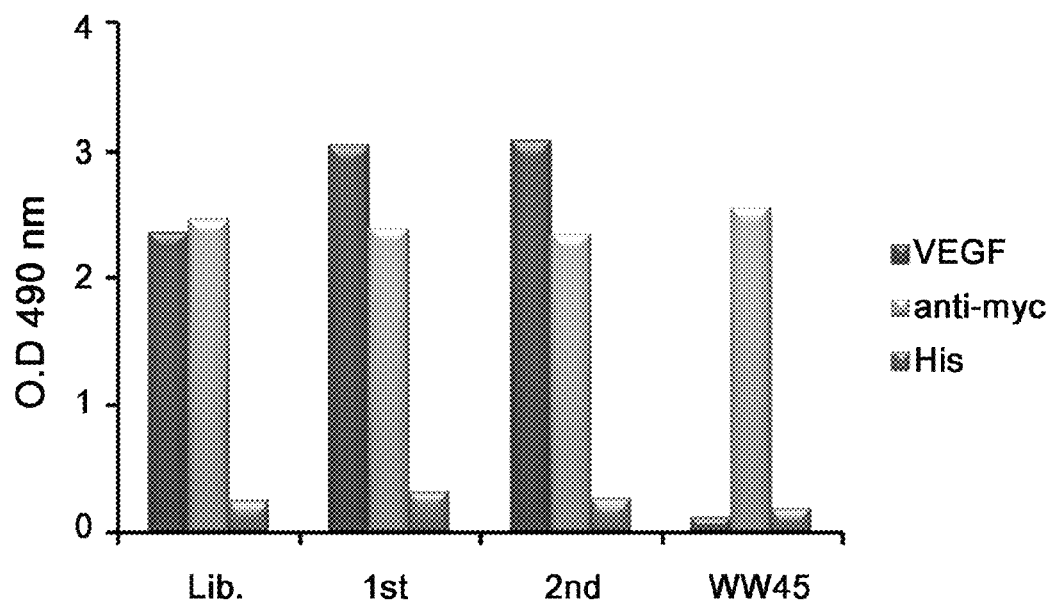
FIG. 14 is a group of drawings illustrating results of phage antibody search from a LC shuffling library in 1st to 3rd pannings.

As shown in FIG. 14, the panning result confirmed by ELISA also showed that a VEGF antigen binding capacity was increased from LC shuffled polyclonal scFv-phage pools, a binding capacity to the 1st panning reached a saturated state, and a value for the tagged H is was relatively low.

61 monoclonal phages with a VEGF antigen binding capacity of at least 2.0 (highlighted in Table 11) were also selected by a monoclonal antibody selection. Then, F6 and G12 in the LC shuffling were used as a positive control group.

[Table 11]

| VEGF ≧ 2 | VEGF | anti-myc | His |  | VEGF | anti-myc | His |  | VEGF | anti-myc | His |
|---|---|---|---|---|---|---|---|---|---|---|---|
| F6(P) | 2.143 | 0.468 | 0.068 | 2A5 | 0.089 | 0.350 | 0.049 | 2A9 | 2.333 | 0.544 | 0.040 |
| 2B1 | 2.058 | 0.485 | 0.049 | 2B5 | 2.099 | 0.364 | 0.042 | 2B9 | 0.133 | 1.131 | 0.059 |
| 2C1 | 0.103 | 0.273 | 0.069 | 2C5 | 2.035 | 0.515 | 0.050 | 2C9 | 2.408 | 0.800 | 0.064 |
| 2D1 | 2.100 | 0.530 | 0.046 | 2D5 | 2.325 | 1.387 | 0.044 | 2D9 | 2.336 | 0.536 | 0.075 |
| 2E1 | 2.195 | 1.599 | 0.062 | 2E5 | 2.124 | 0.270 | 0.044 | 2E9 | 2.424 | 1.845 | 0.077 |
| 2F1 | 2.104 | 0.518 | 0.046 | 2F5 | 1.711 | 0.292 | 0.044 | 2F9 | 2.478 | 1.946 | 0.075 |
| 2G1 | 2.282 | 1.525 | 0.052 | 2G5 | 1.900 | 0.290 | 0.047 | 2G9 | 2.172 | 0.463 | 0.076 |
| 2H1 | 2.137 | 1.504 | 0.061 | 2H5 | 1.997 | 0.509 | 0.055 | 2H9 | 2.497 | 0.857 | 0.076 |
| G12(P) | 2.205 | 1.569 | 0.072 | 2A6 | 0.089 | 0.088 | 0.058 | 2A10 | 2.390 | 0.524 | 0.071 |
| 2B2 | 0.181 | 0.996 | 0.081 | 2B6 | 0.080 | 0.285 | 0.089 | 2B10 | 2.220 | 0.605 | 0.062 |
| 2C2 | 0.130 | 0.992 | 0.044 | 2C6 | 1.250 | 0.508 | 0.053 | 2C10 | 2.158 | 0.593 | 0.088 |
| 2D2 | 2.020 | 0.402 | 0.046 | 2D6 | 2.154 | 0.366 | 0.048 | 2D10 | 2.047 | 3506.000 | 0.073 |
| 2E2 | 2.289 | 1.745 | 0.042 | 2E6 | 0.232 | 0.138 | 0.042 | 2E10 | 2.294 | 0.579 | 0.077 |
| 2F2 | 1.899 | 0.189 | 0.047 | 2F6 | 0.087 | 0.225 | 0.043 | 2F10 | 2.195 | 1.396 | 0.109 |
| 2G2 | 2.186 | 0.763 | 0.054 | 2G6 | 2.253 | 1.472 | 0.107 | 2G10 | 2.428 | 0.698 | 0.077 |
| 2H2 | 2.142 | 1.547 | 0.062 | 2H6 | 1.986 | 0.861 | 0.054 | 2H10 | 0.153 | 0.733 | 0.088 |
| 2A3 | 0.098 | 0.292 | 0.053 | 2A7 | 0.109 | 0.062 | 0.050 | 2A11 | 2.321 | 0.629 | 0.045 |
| 2B3 | 0.092 | 0.131 | 0.099 | 2B7 | 0.063 | 0.056 | 0.045 | 2B11 | 2.351 | 1.790 | 0.047 |
| 2C3 | 1.933 | 0.573 | 0.052 | 2C7 | 2.436 | 0.330 | 0.047 | 2C11 | 2.042 | 0.152 | 0.041 |
| 2D3 | 0.089 | 0.264 | 0.051 | 2D7 | 1.082 | 0.070 | 0.031 | 2D11 | 2.306 | 0.590 | 0.056 |
| 2E3 | 2.119 | 0.191 | 0.045 | 2E7 | 2.267 | 0.132 | 0.055 | 2E11 | 2.533 | 0.557 | 0.052 |
| 2F3 | 0.143 | 0.094 | 0.050 | 2F7 | 2.521 | 1.706 | 0.050 | 2F11 | 0.674 | 0.052 | 0.047 |
| 2G3 | 2.093 | 0.648 | 0.051 | 2G7 | 2.512 | 0.421 | 0.047 | 2G11 | 2.285 | 0.072 | 0.061 |
| 2H3 | 0.213 | 0.690 | 0.059 | 2H7 | 2.546 | 0.331 | 0.070 | 2H11 |  |  |  |
| 2A4 | 0.092 | 0.156 | 0.046 | 2A8 | 1.718 | 0.072 | 0.028 | 2A12 | 0.791 | 1.957 | 0.037 |
| 2B4 | 0.087 | 0.083 | 0.059 | 2B8 | 2.515 | 0.454 | 0.017 | 2B12 | 0.132 | 0.280 | 0.066 |
| 2C4 | 2.165 | 0.399 | 0.091 | 2C8 | 2.586 | 1.690 | 0.066 | 2C12 | 2.256 | 0.950 | 0.052 |
| 2D4 | 0.650 | 1.662 | 0.046 | 2D8 | 2.451 | 0.358 | 0.056 | 2D12 | 2.371 | 1.814 | 0.046 |
| 2E4 | 2.029 | 0.283 | 0.046 | 2E8 | 2.542 | 1.690 | 0.024 | 2E12 | 2.382 | 1.774 | 0.050 |
| 2F4 | 2.174 | 0.471 | 0.044 | 2F8 | 2.507 | 1.826 | 0.046 | 2F12 | 2.286 | 0.667 | 0.052 |
| 2G4 | 2.119 | 0.657 | 0.046 | 2G8 | 2.535 | 1.747 | 0.031 | 2G12 | 2.265 | 0.785 | 0.059 |
| 2H4 | 1.973 | 1.146 | 0.059 | 2H8 | 2.423 | 0.190 | 0.086 | 2H12 |  |  |  |

Figure 15:
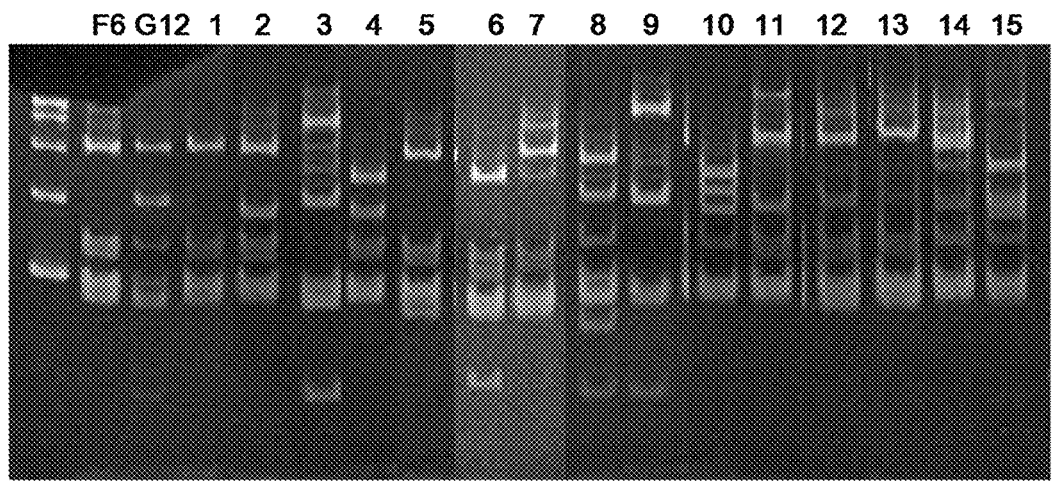
FIG. 15 is a group of drawings illustrating results of a diversity of an LC shuffling monoclonal phage antibody confirmed through a fingerprinting process.

A verification result by a fingerprinting process also confirmed that fragments of monoclonal phage antibodies digested by BstNI had diversity as shown in FIG. 15.

Furthermore, a verification result by nucleotide sequencing analysis confirmed CDR regions of $V_H$ and $V_L$ of the selected antibody as described in Table 12. Homology between the selected antibody and germ line antibody group was investigated. AS a result, 12 VEGF specific phage antibodies with the same HC except for LC different from F6 were obtained, and 3 VEGF specific phage antibodies with the same HC except for LC different from G12 were obtained (Table 13). In particular, about 94.4% homology was shown in 90.1% of light chain. A polypeptide in CDR1, 2, and 3 of light chain of each human antibody was analyzed and it was confirmed that polypeptides with each different sequence were different each other. In FIG. 16, because CDR regions of $V_H$ of the antibody selected by LC shuffling were identical to each other, CDR regions of $V_L$ were compared.

TABLE 12

| Clone | Heavy Chain | | | Light Chain | | |
|---|---|---|---|---|---|---|
| | CDR1 | CDR2 | CDR3 | CDR1 | CDR2 | CDR3 |
| F6(P) | TSGVAVG: SEQ ID No. 12 | LIYWDNDKRYSPSLKN: SEQ ID No. 25 | GDGWLFDF: SEQ ID No. 38 | TGSNSNIGAGHDVH: SEQ ID No. 64 | GNTNRAS: SEQ ID No. 77 | QSYDNSLSGYV: SEQ ID No. 90 |
| 2A09 | TSGVAVG: SEQ ID No. 12 | LIYWDNDKRYSPSLKN: SEQ ID No. 25 | GDGWLFDF: SEQ ID No. 38 | TGSSSNIGAG--YDVH: SEQ ID No. 67 | GNSNRPS: SEQ ID No. 143 | QSYDNSLS---AY: SEQ ID No. 153 |
| 2B05 | TSGVAVG: SEQ ID No. 12 | LIYWDNDKRYSPSLKN: SEQ ID No. 25 | GDGWLFDF: SEQ ID No. 38 | TGGDSNIGAG--YDVN: SEQ ID NO. 130 | GDTFPPS: SEQ ID No. 144 | QSYDSSLS---GY: SEQ ID No. 154 |
| 2C11 | TSGVAVG: SEQ ID No. 12 | LIYWDNDKRYSPSLKN: SEQ IDNo. 25 | GDGWLFDF: SEQ ID No. 38 | RSSQSLVRSDGTTYLS: SEQ ID No. 131 | KISNRFS: SEQ ID No. 145 | MQATFFPFT----: SEQ ID No. 155 |
| 2D10 | TSGVAVG: SEQ ID No. 12 | LIYWDNDKRYSPSLKN: SEQ IDNo. 25 | GDGWLFDF: SEQ ID No. 38 | TGSSSNLGAP--NDVH: SEQ ID No. 132 | GSTNRPS: SEQ ID No. 146 | QSYDNSLS---AY: SEQ ID No. 153 |
| 2E11 | TSGVAVG: SEQ ID No. 12 | LIYWDNDKRYSPSLKN: SEQ ID No. 25 | GDGWLFDF: SEQ ID No. 38 | TGSSSNIGAG--YDVH: SEQ ID No. 67 | GNNNRPS: SEQ ID No. 80 | QSNDPSLGGL--H: SEQ ID No. 156 |
| 2F01 | TSGVAVG: SEQ ID No. 12 | LIYWDNDKRYSPSLKN: SEQ ID No. 25 | GDGWLFDF: SEQ ID No. 38 | TGSSSNIGAP--NDVH: SEQ ID No. 133 | GNTNRP3: SEQ ID No. 147 | QSYDNGLSAS--Y: SEQ ID No. 157 |
| 2G03 | TSGVAVG: SEQ ID No. 12 | LIYWDNDKRYSPSLKN: SEQ ID No. 25 | GDGWLFDF: SEQ ID No. 38 | RSSQSLVRSDGTTYLS: SEQ ID No. 134 | KISNRFS: SEQ ID No. 144 | MQATFFPFT----: SEQ ID No. 155 |
| 2G04 | TSGVAVG: SEQ ID No. 12 | LIYWDNDKRYSPSLKN: SEQ ID No. 25 | GDGWLFDF: SEQ ID No. 38 | TGSRSNFGAG--HDVH: SEQ ID No. 135 | GNNNRPS: SEQ ID No. 80 | QSFDNTLNG---W: SEQ ID No. 158 |
| 2G12 | TSGVAVG: SEQ ID No. 12 | LIYWDNDKRYSPSLKN: SEQ ID No. 25 | GDGWLFDF: SEQ ID No. 38 | TGSSSNIGAG--SDVH: SEQ ID No. 136 | GNNNRPS: SEQ ID No. 80 | QSYDSSLSG---Y: SEQ ID No. 154 |
| 2H07 | TSGVAVG: SEQ ID No. 12 | LIYWDNDKRYSPSLKN: SEQ ID No. 25 | GDGWLFDF: SEQ ID No. 38 | TGSSTNIGAG--YDVH: SEQ ID No. 137 | GNSNRPS: SEQ ID No. 143 | QSYDSSLSG-SLY: SEQ ID No. 159 |
| 2H08 | TSGVAVG: SEQ ID No. 12 | LIYWDNDKRYSPSLKN: SEQ ID No. 25 | GDGWLFDF: SEQ ID No. 38 | SESSSNIGAG--FDYH: SEQ ID No. 138 | GNTDRPS: SEQ ID No. 148 | QSYDSSLR---AY: SEQ ID No. 160 |
| 2H09 | TSGVAVG: SEQ ID No. 12 | LIYWDNDKRYSPSLKN: SEQ ID No. 25 | GDGWLFDF: SEQ ID No. 38 | RASQGIVS-----WLA: SEQ ID No. 139 | AASELQS: SEQ ID No. 149 | QQLNNFLFA----: SEQ ID No. 161 |
| G12(P) | NYAIS: SEQ ID No. 15 | RIIPIYGTPTYAQKFRD: SEQ ID No. 28 | ERSFWNWFAP: SEQ ID No. 41 | TGSSSNIGAGYDVH: SEQ ID No. 67 | GNNNRPS: SEQ ID No. 80 | QSYDSRLGVV: SEQ ID No. 92 |
| 2C05 | NYAIS: SEQ ID No. 15 | RIIPIYGTPTYAQKFRD: SEQ ID No. 28 | ERSFWNWFAP: SEQ ID No. 41 | GSSAGAVISGHYPF: SEQ ID No. 140 | DISNRHF: SEQ ID No. 150 | FVAYG--AIW: SEQ ID No. 162 |
| 2F09 | NYAIS: SEQ ID No. 15 | RIIPIYGTPTYAQKFRD: SEQ ID No. 28 | ERSFWNWFAP: SEQ ID No. 41 | TGSSSNLGAGYDVH: SEQ ID No. 141 | GDVNRPS: SEQ ID No. 151 | QSYDTSLVGS: SEQ ID No. 163 |
| 1F10 | NYAIS: SEQ ID No. 15 | RIIPIYGTPTYAQKFRD: SEQ ID No. 28 | ERSFWNWFAP: SEQ ID No. 41 | RASQP---ISNWLA: SEQ ID No. 152 | ATSILQS: SEQ ID No. 142 | QQHRD--YPL: SEQ ID No. 164 |

TABLE 13

| Clone Name | Vl. | identities | CDR1-aaseq | CDR2-aaseq | CDR3-aaseq | VEGF | a-myc | Ratio | Group |
|---|---|---|---|---|---|---|---|---|---|
| F06(P) | V1-13 | 272/292(93.2%) | TGSNSNIGAG--HDVH | GNTNRAS | QSYDNSLS---GY | 2.1429 | 0.4678 | 4.5808 | P |
| A09 | V1-13 | 282/298(64.6%) | TGSSSNIGAG--YDVH | GNSNRPS | QSYDNSLS---AY | 2.3329 | 0.5437 | 4.2908 | 1 |
| B05 | V1-13 | 266/292(91.1%) | TGGDSNIGAG--YDVN | GDTFRPS | QSYDSSLS---GY | 2.0985 | 0.3641 | 5.7635 | 2 |
| C11 | A29 | 280/299(93.6%) | RSSQSLVRSDGTTYLS | KISNRFS | MQATFFPFT---- | 2.0415 | 0.1523 | 13.4045 | 3 |
| D10 | V1-13 | 268/292(91.8%) | TGSSSNIGAP--NDVH | GSTNRPS | QSYDNSLS---AY | 2.0469 | 0.3506 | 5.8383 | 4 |
| E11 | V1-13 | 269/291(92.4%) | TGSSSNIGAG--YDVH | GNNNRPS | QSNDPSIGGL--H | 2.5328 | 0.5573 | 4.5448 | 5 |
| F01 | V1-13 | 273/289(94.5%) | TGSSSNIGAP--NDVH | GNTNRPS | QSYDNGLSAS--Y | 2.1038 | 0.5177 | 4.0637 | 6 |
| G03 | A23 | 282/299(94.3%) | RSSQSLVRSDGTTYLS | KISNRFS | MQATFFPFT---- | 2.0927 | 0.6483 | 3.2880 | 7 |
| G04 | V1-13 | 267/290(92.1%) | TGSRSNPGAG--HDVH | GNNNRPS | QSFDNTLNG---W | 2.1193 | 0.6572 | 3.2247 | 8 |
| G12 | V1-13 | 283/292(96.9%) | TGSSSNIGAG--SDVH | GNNNRPS | QSYDSSLSG---Y | 2.2646 | 0.7852 | 2.8841 | 9 |
| H07 | V1-13 | 277/293(94.5%) | TGSSTNIGAG--YDVH | GNSNRPS | QSYDSSLSG-SLY | 2.546 | 0.3305 | 7.7035 | 10 |
| H08 | V1-13 | 275/293(92.3%) | SESSSNIGAG-FDVH | GNTDRPS | QSYDSSLR---AY | 2.4231 | 0.1815 | 12.7868 | 11 |
| H09 | L8 | 258/283(91.2%) | RASQGIVS-----WLA | AASELQS | QQLNNFLFA---- | 2.4965 | 0.8568 | 2.9137 | 12 |
| G12(P) | V1-13 | 279/289(96.5%) | TGSSSNIGAGYDVH | GNNNRPS | QSYDS-RLGV | 2.2051 | 1.5689 | 1.4055 | P |
| C05 | V3-3 | 270/287(94.4%) | GSSAGAVTSGHYPF | DTSNRHF | FVAYG--AIN | 2.0353 | 0.5153 | 3.9497 | 13 |
| F09 | V1-13 | 281/299(94.0%) | TGSSSNLGAGYDVH | GDVNRPS | QSYDTSLVGS | 2.4779 | 1.9456 | 1.2736 | 14 |
| F10 | L15 | 256/284(90.1%) | RSQP---ISNWLA | ATSILQS | QQBRD--YPL | 2.1954 | 1.3957 | 1.5730 | 15 |

Example 6

Characterization of LC Shuffling Human Antibodies

<6-1> Measurement of Binding Capacity

A binding capacity was measured for an LC shuffling monoclonal antibody selected in Example 5-3 by the same manner as described in Example 4-1. As a result, binding capacities of the 15 LC shuffling monoclonal phage antibodies against the antigen were confirmed as indicated in Table 14.

TABLE 14

| (Dilution) | VEGF-His | | | | | |
|---|---|---|---|---|---|---|
| | 3125 | 625 | 125 | 25 | 5 | 1 |
| F6(P) | 0.4502 | 1.0161 | 1.7492 | 2.3787 | 2.6334 | 2.6027 |
| G12(P) | 1.2041 | 1.8817 | 2.3696 | 2.5961 | 2.7582 | 2.5957 |
| 2A9 | 0.5874 | 1.1848 | 1.8134 | 2.352 | 2.6411 | 2.5364 |
| 2B5 | 0.1951 | 0.4776 | 1.1497 | 1.9639 | 2.428 | 2.6934 |
| 2C5 | 0.071 | 0.1258 | 0.3388 | 0.9994 | 2.1226 | 2.6528 |
| 2C11 | 0.0592 | 0.0863 | 0.2195 | 0.7511 | 1.7178 | 2.4353 |
| 2D10 | 0.0955 | 0.1876 | 0.5045 | 1.1569 | 2.0359 | 2.4843 |
| 2E11 | 0.36 | 0.7239 | 1.4011 | 2.0133 | 2.4173 | 2.3286 |
| 2F1 | 0.2977 | 0.5735 | 1.173 | 1.9021 | 2.3977 | 2.3666 |
| 2F9 | 0.941 | 1.4798 | 2.194 | 2.4754 | 2.5794 | 2.4680 |
| 2F10 | 0.0798 | 0.1158 | 0.324 | 0.8996 | 1.9159 | 2.4501 |
| 2G3 | 0.0888 | 0.1682 | 0.4737 | 1.1641 | 2.1681 | 2.5639 |
| 2G4 | 0.5673 | 1.1624 | 1.8694 | 2.4342 | 2.6262 | 2.6711 |
| 2G12 | 0.5464 | 0.9802 | 1.9239 | 2.4643 | 2.7957 | 2.7999 |
| 2H7 | 0.4001 | 0.6833 | 1.6313 | 2.228 | 2.7175 | 2.7383 |
| 2H8 | 0.1404 | 0.2725 | 0.9064 | 1.617 | 2.4888 | 2.8512 |
| 2H9 | 0.1476 | 0.3282 | 0.9177 | 1.9178 | 2.6841 | 3.0981 |

<6-2> Conversion Analysis of Whole IgG

Figure 12A:
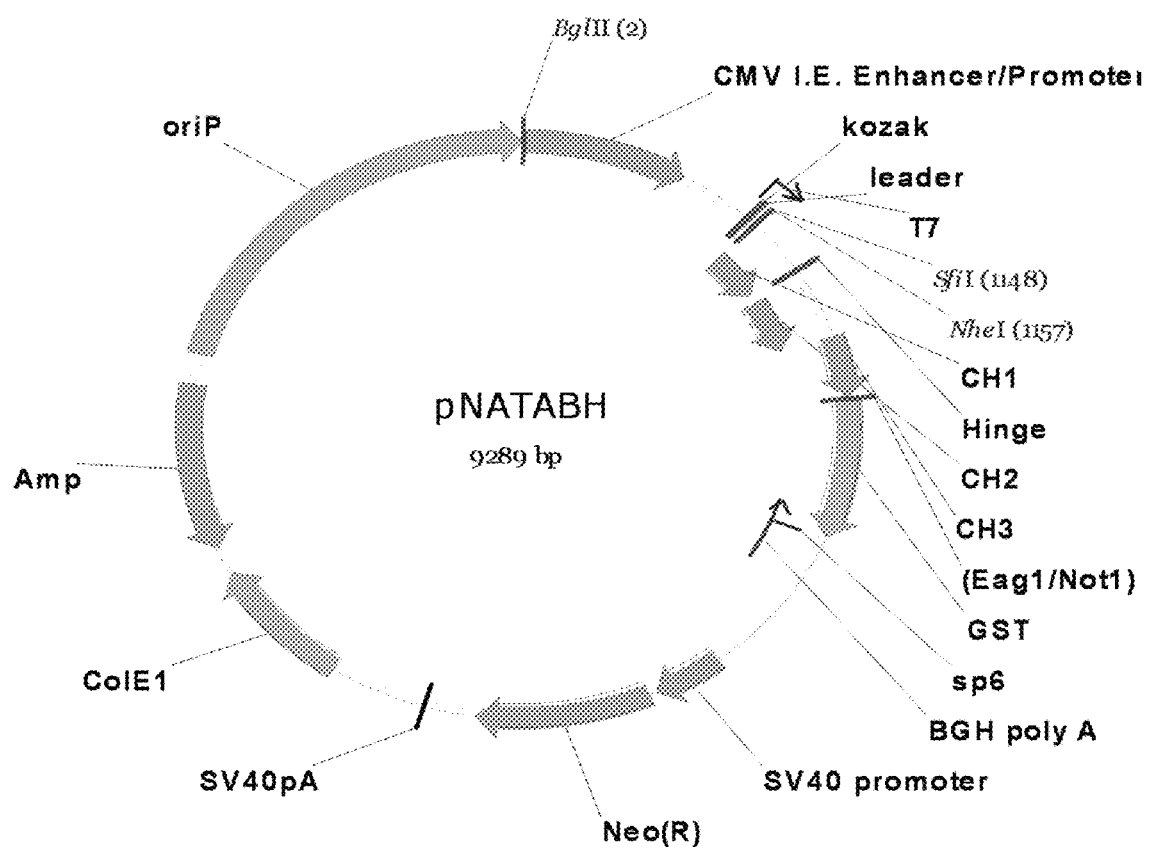
FIG. 12 is a group of drawings illustrating cleavage maps of pNATAB H and pNATAB L vectors:
  a: pNATAB H vector, b: pNATAB L vector

In order to convert LC shuffling monoclonal antibodies selected in Example 5-3 into a whole IgG vector in the phage, a colony PCR was performed by the same manner as described in Example 4-2 by using a primer pair in Table 15. As a result, the heavy chain was ligated to a pNATAB H vector (FIG. 12a) and the light chain was ligated to a pNATAB L vector (FIG. 12b). A nucleotide sequencing analysis was performed by extracting DNA from the vector. As a result, it was confirmed that sequences of the heavy and light chains of 15 clone phages for an LC shuffling monoclonal phage antibody converted into a whole IgG were identical to those of phage antibodies.

TABLE 15

| Clones | Heavy chain | | Light chain | | |
|---|---|---|---|---|---|
| | Forwardprimer (Sfi I) | Reverseprimer (Nhe I) | Forwardprimer (Sfi I) | | Reverseprimer (Bgl II) |
| F06(P) | NATVH2-3: SEQ ID No. 179 | TTGGTGG CCACAGC GGCCGAT GTCCACT CGCAGGT CACCTTG AGGGAG TC | NATJH-ALL: SEQ ID No. 114 | NATVL10: SEQ ID No. 116 | TTGGTGGCCACA GCGGCCGATGTC CACTCGCAGCTC GTGCTGACTCAG CC | NATJL1-R: SEQ ID No. 186 | GAGGAGAG ATCTTAGGA CGGTGACCT TGGTCCC |
| 2A09 | | | GAG GAG GCT AGC TGA GGA GAC GGT GA | NATVL13: SEQ ID No. 180 | TTGGTGGCCACA GCGGCCGATGTC CACTCGCAGTTCG TGCTGACTCAGCC | | |
| 2B05 | | | | NATVL10: SEQ ID No. 116 | TTGGTGGCCACA GCGGCCGATGTC CACTCGCAGCTC GTGCTGACTCAG CC | | |
| 2C11 | | | | NATVK3: SEQ ID No. 181 | TTGGTGGCCACA GCGGCCGATGTC CACTCGGATATTG TGATGACCCAGA CTCC | NATJK-R2: SEQ ID No. 187 | GAGGAGAG ATCTTTTGAT CTCCACTTT GGT |
| 2D10 | | | | NATVL10: SEQ ID No. 116 | TTGGTGGCCACA GCGGCCGATGTC CACTCGCAGCTC GTGCTGACTCAG CC | NATJL1-R: SEQ ID No. 188 | GAGGAGAG ATCTTAGGA CGGTGACCT TGGTCCC |
| 2E11 | | | | | | | |
| 2F01 | | | | | | | |
| 2G03 | | | | NATVK3 | TTGGTGGCCACA GCGGCCGATGTC CACTCGGATATTG TGATGACCCAGA CTCC | NATJK-R7: SEQ ID No. 119 | GAGGAGAG ATCTTTTGAT ATCCACTTT GGT |
| 2G04 | | | | NATVL10: SEQ ID No. 116 | TTGGTGGCCACA GCGGCCGATGTC CACTCGCAGCTC GTGCTGACTCAG CC | NATJL2-R: SEQ ID No. 124 | GAGGAGAG ATCTTAGGA CGGTCAGCT TGGTCCC |
| 2G12 | | | | | CC | NATJL1-R SEQ ID No. | GAGGAGAG ATCTTAGGA |
| 2H07 | | | | | | | |
| 2H08 | | | | NATVL13: SEQ ID No. 182 | TTGGTGGCCACA GCGGCCGATGTC CACTCGCAGTTCG TGCTGACTCAGCC | 189 | CGGTGACCT TGGTCCC |
| 2H09 | | | | NATVK1-1: | TTGGTGGCCACA GCGGCCGATGTC | NATJK-R2: SEQ ID No. | GAGGAGAG ATCTTTTGAT |

TABLE 15-continued

| Clones | Heavy chain | | Light chain | | | |
|---|---|---|---|---|---|---|
| | Forwardprimer (Sfi I) | Reverseprimer (Nhe I) | Forwardprimer (Sfi I) | | Reverseprimer (Bgl II) | |
| | | | SEQ ID No. 183 | CACTCGGACATC CAGATGACCCAG TC | 190 | CTCCACTTT GGT |
| G12(P) | NATVH1-1: SEQ ID No. 112 | TTGGTGG CCACAGC GGCCGAT GTCCACT CGCAGGT GCAGCTG GTGCAGTC | NATJH-ALL: SEQ ID No. 114 | NATVL10: SEQ ID No. 116 | TTGGTGGCCACA GCGGCCGATGTC CACTCGCAGCTC GTGCTGACTCAG CC | NATJL2-R: SEQ ID No. 124 | GAGGAGAG ATCTTAGGA CGGTCAGCT TGGTCCC |
| 2C05 | | | | NATVL12: SEQ ID No. 184 | TTGGTGGCCACA GCGGCCGATGTC CACTCGCAGGCT GTGGTGACTCAG GA | NATJL5-R: SEQ ID No. 191 | GAGGAGAG ATCTTAGGA CGGTCAGCT CGGT |
| 2F09 | | | | NATVL13: SEQ ID No. 185 | TTGGTGGCCACA GCGGCCGATGTC CACTCGCAGTTCG TGCTGACTCAGCC | NATJL2-R: SEQ ID No. 124 | GAGGAGAG ATCTTAGGA CGGTCAGCT TGGTCCC |
| 1F10 | | | | NATVK1-1: SEQ ID No. 115 | TTGGTGGCCACA GCGGCCGATGTC CACTCGGACATC CAGATGACCCAG TC | NATJK-R7: SEQ ID No. 119 | GAGGAGAG ATCTTTTGAT ATCCACCTT GGT |

<6-3> Confirmation of Binding Capacities of Anti-VEGF Antibodies

In order to confirm a VEGF binding capacity by comparing LC shuffling monoclonal phage antibodies with F6 and G12, respectively, ELISA was performed by the same manner as described in Example 4-5.

As a result, degrees of binding of only 2C11, 2G03, 2C05, and 2F10 were too low while others exhibited high affinities similar to that of a positive control group, as indicated in Table 16.

TABLE 16

| (nM) | 50 | 25 | 12.5 | 6.25 | 3.125 | 1.5625 | 0.78125 | 0.39063 | 0.19531 | 0.09766 | 0.04883 | 0.02441 | Kd value(M)(R2) |
|---|---|---|---|---|---|---|---|---|---|---|---|---|---|
| IgG | 0.0952 | 0.1015 | 0.1032 | 0.1227 | 0.0951 | 0.0993 | 0.0941 | 0.1011 | 0.0911 | 0.092 | 0.091 | 0.0874 | — |
| F06(P) | 2.5809 | 2.4608 | 2.6248 | 2.5662 | 2.5017 | 2.5287 | 2.4768 | 2.2867 | 1.8512 | 1.3136 | 0.864 | 0.4938 | 8.8 * 10−11 M (0.99) |
| 2A09 | 2.529 | 2.5265 | 2.6023 | 2.6243 | 2.4743 | 2.5441 | 2.4944 | 2.234 | 1.8063 | 1.1968 | 0.8211 | 0.4838 | 9.8 * 10−11 M (0.99) |
| 2B05 | 2.479 | 2.5411 | 2.499 | 2.4371 | 2.4739 | 2.4681 | 2.5128 | 2.1458 | 1.6658 | 1.1279 | 0.6944 | 0.4271 | 1.1 * 10−10 M (0.98) |
| 2C11 | 0.0881 | 0.0942 | 0.0919 | 0.0912 | 0.0982 | 0.1021 | 0.0989 | 0.101 | 0.0928 | 0.0895 | 0.0879 | 0.0865 | — |
| 2D10 | 2.1757 | 2.0057 | 1.4823 | 1.0899 | 0.7038 | 0.3882 | 0.2463 | 0.1615 | 0.1252 | 0.1033 | 0.0956 | 0.0892 | 8.4 * 10−9 M (0.98) |
| 2E11 | 2.1736 | 1.7494 | 1.3507 | 0.8021 | 0.5537 | 0.3098 | 0.1866 | 0.1332 | 0.1077 | 0.0986 | 0.0929 | 0.0907 | 1.3 * 10−8M (0.94) |
| 2F01 | 2.6062 | 2.5367 | 2.2299 | 2.2665 | 1.9197 | 1.6427 | 1.2476 | 0.7042 | 0.4147 | 0.2151 | 0.1299 | 0.1146 | 9.4 * 10−10M (0.99) |
| 2G03 | 0.0886 | 0.0926 | 0.092 | 0.939 | 0.0927 | 0.096 | 0.0985 | 0.0929 | 0.0986 | 0.1 | 0.086 | 0.0927 | — |
| 2G04 | 2.5279 | 2.5187 | 2.4115 | 2.4195 | 2.5001 | 2.4575 | 2.424 | 2.4811 | 2.3615 | 1.6605 | 1.2495 | 0.7616 | 3.3 * 10−11 M (1) |
| 2G12 | 2.5233 | 2.546 | 2.3541 | 2.6124 | 2.4604 | 2.4384 | 2.4091 | 2.0182 | 1.6568 | 1.1688 | 0.6642 | 0.4813 | 1.1 * 10−10M (0.99) |
| 2H07 | 2.3654 | 2.4546 | 2.548 | 2.4666 | 2.3474 | 1.8805 | 1.5607 | 1.152 | 0.5821 | 0.3146 | 0.1824 | 0.1408 | 5.3 * 10−10M (0.99) |
| 2H08 | 2.5012 | 2.5022 | 2.6496 | 2.5016 | 2.5143 | 2.1478 | 2.1006 | 1.7333 | 1.0913 | 0.6665 | 0.3348 | 0.2256 | 2.5 * 10−10M (0.99) |
| 2H09 | 1.1042 | 2.0759 | 2.0025 | 1.7631 | 1.3284 | 0.8864 | 0.5223 | 0.3525 | 0.2049 | 0.1341 | 0.1055 | 0.0873 | 2.4 * 10−9M (1) |
| G12(P) | 2.7337 | 2.4535 | 2.5613 | 2.4466 | 2.3736 | 2.0751 | 1.8909 | 1.2653 | 0.7613 | 0.4329 | 0.2541 | 0.1633 | 4.2 * 10−10M (0.99) |
| 2C05 | 0.1073 | 0.1434 | 0.1019 | 0.1036 | 0.0974 | 0.1023 | 0.1175 | 0.1004 | 0.0951 | 0.0985 | 0.0935 | 0.0937 | — |
| 2F09 | 2.6076 | 2.3879 | 2.4921 | 2.4349 | 2.2943 | 2.0733 | 2.1207 | 1.6154 | 1.0599 | 0.6351 | 0.3728 | 0.231 | 2.5 * 10−10M (0.99) |
| 2F10 | 0.807 | 0.4553 | 0.2579 | 0.1709 | 0.149 | 0.1266 | 0.1185 | 0.1107 | 0.1049 | 0.1058 | 0.1009 | 0.093 | 7.8 * 10−8M (0.96) |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A VEGF-specific human antibody comprising:
a heavy chain variable region ($V_H$) comprising a heavy chain complementarity determining region (HCDR) 1 having the amino acid sequence of SEQ ID NO: 12, a HCDR 2 having the amino acid sequence of SEQ ID NO: 25, and a HCDR 3 having the amino acid sequence of SEQ ID NO: 38; and
a light chain variable region ($V_L$) comprising a light chain complementarity determining region (LCDR) 1 having the amino acid sequence of SEQ ID NO: 64, a LCDR 2 having the amino acid sequence of SEQ ID NO: 77, and a LCDR 3 having the amino acid sequence of SEQ ID NO: 90.

2. The human antibody as set forth in claim 1, wherein the heavy chain variable region comprises the amino acid sequence of SEQ ID NO: 51.

3. The human antibody as set forth in claim 1, wherein the light chain variable region comprises the amino acid sequence of SEQ ID NO: 101.

4. A composition comprising the human antibody of claim 1.

5. A pharmaceutical composition comprising the human antibody of claim 1.

6. A method for preparing a VEGF-specific human antibody, the method comprising:
1) constructing a first polynucleotide encoding a heavy chain of the human antibody of claim 1;
2) constructing a second polynucleotide encoding a light chain of the human antibody of claim 1;
3) constructing a first expression vector comprising the polynucleotide of the first polynucleotide;
4) constructing a second expression vector comprising the polynucleotide of the second polynucleotide;
5) preparing a transformant by introducing the first expression vector and the second expression vector simultaneously into a host cell;
6) incubating the transformant of step 5); and
7) purifying the human antibody of claim 1 from the medium.

7. A pharmaceutical composition for preventing or treating a disease caused by VEGF-overexpression, comprising a pharmaceutically acceptable carrier and a VEGF-specific human antibody, wherein the VEGF-specific human antibody comprises:
a heavy chain variable region ($V_H$) comprising a HCDR1 having the amino acid sequence of SEQ ID NO: 12, a HCDR2 having the amino acid sequence of SEQ ID NO: 25, and a HCDR3 having the amino acid sequence of SEQ ID NO: 38; and
a light chain variable region ($V_L$) comprising a LCDR1 having the amino acid sequence of SEQ ID NO: 64, a LCDR2 having the amino acid sequence of SEQ ID NO: 77, and a LCDR3 having the amino acid sequence of SEQ ID NO: 90.

8. The pharmaceutical composition as set forth in claim 7, wherein the disease caused by VEGF-overexpression is a disease associated with cancer or angiogenesis.

9. The pharmaceutical composition as set forth in claim 8, wherein the cancer is selected from the group consisting of colorectal cancer, renal cell cancer, lung cancer, breast cancer, and ovarian cancer.

10. The pharmaceutical composition as set forth in claim 8, wherein the disease associated with angiogenesis is selected from the group consisting of rheumatoid arthritis, diabetic retinopathy, ischemic retinopathy, psoriasis, proliferative diabetic retinopathy, and diabetic macular edema.

11. A method for treating a disease caused by VEGF-overexpression, the method comprising administering to a subject with the disease a pharmaceutically effective amount of a VEGF-specific human antibody comprising:
a heavy chain variable region ($V_H$) comprising a HCDR1 having the amino acid sequence of SEQ ID NO: 12, a HCDR2 having the amino acid sequence of SEQ ID NO: 25, and a HCDR3 having the amino acid sequence of SEQ ID NO: 38; and
a light chain variable region ($V_L$) comprising a LCDR1 having the amino acid sequence of SEQ ID NO: 64, a LCDR2 having the amino acid sequence of SEQ ID NO: 77, and a LCDR3 having the amino acid sequence of SEQ ID NO: 90.

12. The method as set forth in claim 11, wherein the VEGF-specific human antibody is administered in combination with chemotherapy.

13. The method as set forth in claim 11, wherein the disease caused by VEGF-overexpression is a disease associated with cancer or angiogenesis.

14. The method as set forth in claim 13, wherein the cancer is selected from the group consisting of colorectal cancer, pancreatic cancer, renal cell cancer, lung cancer, breast cancer, and ovarian cancer.

15. The method as set forth in claim 13, wherein the disease associated with angiogenesis is selected from the group consisting of rheumatoid arthritis, diabetic retinopathy, ischemic retinopathy, psoriasis, proliferative diabetic retinopathy, and diabetic macular edema.

* * * * *

SEQUENCE LISTING

```
<160> NUMBER OF SEQ ID NOS: 191

<210> SEQ ID NO 1
<211> LENGTH: 30
<212> TYPE: DNA
<213> ORGANISM: Artificial Sequence
<220> FEATURE:
<223> OTHER INFORMATION: VEGF Forward primer

<400> SEQUENCE: 1
gctctagagt gatgaactttt ctgctgtctt                                    30

<210> SEQ ID NO 2
<211> LENGTH: 26
<212> TYPE: DNA
<213> ORGANISM: Artificial Sequence
<220> FEATURE:
<223> OTHER INFORMATION: VEGF Reverse primer

<400> SEQUENCE: 2
cggaattccc gcctcggctt gtcaca                                         26

<210> SEQ ID NO 3
<211> LENGTH: 36
<212> TYPE: DNA
<213> ORGANISM: Artificial Sequence
<220> FEATURE:
<223> OTHER INFORMATION: pcDNA3.1-VEGF forward primer

<400> SEQUENCE: 3 caggggggccg tgggggccgc agaaggagga gggcag                             36

<210> SEQ ID NO 4
<211> LENGTH: 37
<212> TYPE: DNA
<213> ORGANISM: Artificial Sequence
<220> FEATURE:
<223> OTHER INFORMATION: pcDNA3.1-VEGF Reverse primer

<400> SEQUENCE: 4
tagcggccga cgcggccaac cgcctcggct tgtcaca                             37

<210> SEQ ID NO 5
<211> LENGTH: 5
<212> TYPE: PRT
<213> ORGANISM: Artificial Sequence
<220> FEATURE:
<223> OTHER INFORMATION: A4 HC-CDR1

<400> SEQUENCE: 5

Asp Tyr Ala Met His
1               5

<210> SEQ ID NO 6
<211> LENGTH: 5
<212> TYPE: PRT
<213> ORGANISM: Artificial Sequence
<220> FEATURE:
<223> OTHER INFORMATION: B12 HC-CDR1

<400> SEQUENCE: 6
```

```
Ser Tyr Ala Ile Ser
1               5

<210> SEQ ID NO 7
<211> LENGTH: 5
<212> TYPE: PRT
<213> ORGANISM: Artificial Sequence
<220> FEATURE:
<223> OTHER INFORMATION: C11 HC-CDR1

<400> SEQUENCE: 7

Ser Asp Ala Ile Ser
1               5

<210> SEQ ID NO 8
<211> LENGTH: 5
<212> TYPE: PRT
<213> ORGANISM: Artificial Sequence
<220> FEATURE:
<223> OTHER INFORMATION: C12 HC-CDR1

<400> SEQUENCE: 8

Ser Tyr Gly Met Asn
1               5

<210> SEQ ID NO 9
<211> LENGTH: 5
<212> TYPE: PRT
<213> ORGANISM: Artificial Sequence
<220> FEATURE:
<223> OTHER INFORMATION: C5 HC-CDR1

<400> SEQUENCE: 9

Ser Tyr Ser Met His
1               5

<210> SEQ ID NO 10
<211> LENGTH: 5
<212> TYPE: PRT
<213> ORGANISM: Artificial Sequence
<220> FEATURE:
<223> OTHER INFORMATION: C9 HC-CDR1

<400> SEQUENCE: 10

Ser Tyr Ala Met His
1               5

<210> SEQ ID NO 11
<211> LENGTH: 5
<212> TYPE: PRT
<213> ORGANISM: Artificial Sequence
<220> FEATURE:
<223> OTHER INFORMATION: D12 HC-CDR1

<400> SEQUENCE: 11

Glu Tyr Ala Met His
1               5

<210> SEQ ID NO 12
<211> LENGTH: 7
<212> TYPE: PRT
<213> ORGANISM: Artificial Sequence
<220> FEATURE:
<223> OTHER INFORMATION: E9 & F6 HC-CDR1

<400> SEQUENCE: 12

Thr Ser Gly Val Ala Val Gly
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: F2 HC-CDR1

<400> SEQUENCE: 13

Ser Tyr Ala Met Ser
1               5

<210> SEQ ID NO 14
<211> LENGTH: 5
<212> TYPE: PRT
<213> ORGANISM: Artificial Sequence
<220> FEATURE:
<223> OTHER INFORMATION: F9 HC-CDR1

<400> SEQUENCE: 14

Thr Thr Ala Ile Thr
1               5

<210> SEQ ID NO 15
<211> LENGTH: 5
<212> TYPE: PRT
<213> ORGANISM: Artificial Sequence
<220> FEATURE:
<223> OTHER INFORMATION: G12 HC-CDR1

<400> SEQUENCE: 15

Asn Tyr Ala Ile Ser
1               5

<210> SEQ ID NO 16
<211> LENGTH: 5
<212> TYPE: PRT
<213> ORGANISM: Artificial Sequence
<220> FEATURE:
<223> OTHER INFORMATION: G9 HC-CDR1

<400> SEQUENCE: 16

Thr Tyr Ala Leu His
1               5

<210> SEQ ID NO 17
<211> LENGTH: 5
<212> TYPE: PRT
<213> ORGANISM: Artificial Sequence
<220> FEATURE:
<223> OTHER INFORMATION: H7 HC-CDR1

<400> SEQUENCE: 17

Lys Tyr Gly Met His
1               5

<210> SEQ ID NO 18
<211> LENGTH: 17
<212> TYPE: PRT
<213> ORGANISM: Artificial Sequence
<220> FEATURE:
<223> OTHER INFORMATION: A4 HC-CDR2

<400> SEQUENCE: 18

Phe Ile Asn Glu Asp Gly Gly Asn Ile Tyr Tyr Gly Asp Ser Val Lys
1               5                   10                  15

Gly
```

```
<210> SEQ ID NO 19
<211> LENGTH: 17
<212> TYPE: PRT
<213> ORGANISM: Artificial Sequence
<220> FEATURE:
<223> OTHER INFORMATION: B12 HC-CDR2

<400> SEQUENCE: 19

Gly Ile Ile Pro Ile Phe Gly Thr Ala Asn Tyr Ala Gln Lys Phe Gln
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: C11 HC-CDR2

<400> SEQUENCE: 20

Gly Val Ile Pro Ile Phe Ala Thr Thr Thr Tyr Ala Gln Gly Phe Gln
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: C12 HC-CDR2

<400> SEQUENCE: 21

Ser Ile Ser Ser Ser Ser Ser Ser Ile His Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: C5 HC-CDR2

<400> SEQUENCE: 22

Gly Ile Ser Tyr Asp Gly Ser Ser Lys Gln Phe Gly Asp Ser Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: C9 HC-CDR2

<400> SEQUENCE: 23

Val Ile Ser Tyr Asp Gly Ser Asn Lys Tyr Tyr Ala Asp Ser Val Lys
1               5                   10                  15

Gly

<210> SEQ ID NO 24
<211> LENGTH: 17
<212> TYPE: PRT
```

```
<213> ORGANISM: Artificial Sequence
<220> FEATURE:
<223> OTHER INFORMATION: D12 HC-CDR2

<400> SEQUENCE: 24

Leu Ile Ser Gly Asp Asp Tyr Asn Thr Phe Tyr Ala Asp Ser Val Lys
1               5                   10                  15

Gly

<210> SEQ ID NO 25
<211> LENGTH: 16
<212> TYPE: PRT
<213> ORGANISM: Artificial Sequence
<220> FEATURE:
<223> OTHER INFORMATION: E9 & F6 HC-CDR2

<400> SEQUENCE: 25

Leu Ile Tyr Trp Asp Asn Asp Lys Arg Tyr Ser Pro Ser Leu Lys Asn
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: F2 HC-CDR2

<400> SEQUENCE: 26

Tyr Ile Ser Ser Ser Gly His Asp Ile Tyr Tyr Ala Asp Pro Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: F9 HC-CDR2

<400> SEQUENCE: 27

Trp Ile Thr Pro Phe Asn Gly Asn Thr Phe Tyr Ala Gln Lys Phe Gln
1               5                   10                  15

Asp

<210> SEQ ID NO 28
<211> LENGTH: 17
<212> TYPE: PRT
<213> ORGANISM: Artificial Sequence
<220> FEATURE:
<223> OTHER INFORMATION: G12 HC-CDR2

<400> SEQUENCE: 28

Arg Ile Ile Pro Ile Tyr Gly Thr Pro Thr Tyr Ala Gln Lys Phe Arg
1               5                   10                  15

Asp

<210> SEQ ID NO 29
<211> LENGTH: 17
<212> TYPE: PRT
<213> ORGANISM: Artificial Sequence
<220> FEATURE:
<223> OTHER INFORMATION: G9 HC-CDR2

<400> SEQUENCE: 29

Val Ile Ser His Asp Gly Thr Thr Asp Tyr Tyr Arg Asp Ser Val Lys
```

```
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: H7 HC-CDR2

<400> SEQUENCE: 30

Phe Ile Trp Phe Asp Gly Ser Asn Lys Phe Tyr Ala Asp Ser Val Lys
1               5                   10                  15

Gly

<210> SEQ ID NO 31
<211> LENGTH: 10
<212> TYPE: PRT
<213> ORGANISM: Artificial Sequence
<220> FEATURE:
<223> OTHER INFORMATION: A4 HC-CDR3

<400> SEQUENCE: 31

Glu Pro Ser Gly Ser Leu Thr Phe Asp Tyr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: B12 HC-CDR3

<400> SEQUENCE: 32

Asp Arg Ser Gly Tyr Thr Ala Met Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: C11 HC-CDR3

<400> SEQUENCE: 33

Gly Gln Met Asp Arg Gly Gly Gly Leu Asp Pro
1               5                   10

<210> SEQ ID NO 34
<211> LENGTH: 9
<212> TYPE: PRT
<213> ORGANISM: Artificial Sequence
<220> FEATURE:
<223> OTHER INFORMATION: C12 HC-CDR3

<400> SEQUENCE: 34

Leu Gly Pro Tyr Asp Ala Phe Asp Phe
1               5

<210> SEQ ID NO 35
<211> LENGTH: 14
<212> TYPE: PRT
<213> ORGANISM: Artificial Sequence
<220> FEATURE:
<223> OTHER INFORMATION: C5 HC-CDR3

<400> SEQUENCE: 35
```

```
Asp Gly Val Pro Gly His Ser Tyr Gly Ile Gly Met Asp Val
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: C9 HC-CDR3

<400> SEQUENCE: 36

```
Asp Val Asp Ser Trp Ser Gln Gly Trp Phe Pro His
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: D12 HC-CDR3

<400> SEQUENCE: 37

```
Asp Ala Gly Pro Ala Gly Gly Gly Gly Leu Asp His
1               5                   10
```

<210> SEQ ID NO 38
<211> LENGTH: 8
<212> TYPE: PRT
<213> ORGANISM: Artificial Sequence
<220> FEATURE:
<223> OTHER INFORMATION: E9 & F6 HC-CDR3

<400> SEQUENCE: 38

```
Gly Asp Gly Trp Leu Phe Asp Phe
1               5
```

<210> SEQ ID NO 39
<211> LENGTH: 11
<212> TYPE: PRT
<213> ORGANISM: Artificial Sequence
<220> FEATURE:
<223> OTHER INFORMATION: F2 HC-CDR3

<400> SEQUENCE: 39

```
Asp Lys Leu Ala Thr Pro Gly Ala Phe Asp Ile
1               5                   10
```

<210> SEQ ID NO 40
<211> LENGTH: 13
<212> TYPE: PRT
<213> ORGANISM: Artificial Sequence
<220> FEATURE:
<223> OTHER INFORMATION: F9 HC-CDR3

<400> SEQUENCE: 40

```
Ser Gln Ala Ala Glu Leu Gly Thr Gly Ala Phe Asp Ile
1               5                   10
```

<210> SEQ ID NO 41
<211> LENGTH: 10
<212> TYPE: PRT
<213> ORGANISM: Artificial Sequence
<220> FEATURE:
<223> OTHER INFORMATION: G12 HC-CDR3

<400> SEQUENCE: 41

```
Glu Arg Ser Phe Trp Asn Trp Phe Ala Pro
```

<210> SEQ ID NO 42
<211> LENGTH: 9
<212> TYPE: PRT
<213> ORGANISM: Artificial Sequence
<220> FEATURE:
<223> OTHER INFORMATION: G9 HC-CDR3

<400> SEQUENCE: 42

Asp Gly Ser Gly Tyr Phe Phe Asp Tyr
1               5

<210> SEQ ID NO 43
<211> LENGTH: 12
<212> TYPE: PRT
<213> ORGANISM: Artificial Sequence
<220> FEATURE:
<223> OTHER INFORMATION: H7 HC-CDR3

<400> SEQUENCE: 43

Asp Arg Asp Tyr Tyr Gly Ser Gly Pro Leu Asp Tyr
1               5                   10

<210> SEQ ID NO 44
<211> LENGTH: 139
<212> TYPE: PRT
<213> ORGANISM: Artificial Sequence
<220> FEATURE:
<223> OTHER INFORMATION: VEGF A4 heavy chain

<400> SEQUENCE: 44

Met Ala Gln Met Gln Leu Val Glu Ser Gly Gly Gly Val Val Gln Pro
1               5                   10                  15

Gly Gly Ser Leu Arg Leu Ser Cys Ala Ala Ser Gly Phe Ile Phe Asn
            20                  25                  30

Asp Tyr Ala Met His Trp Val Arg Gln Ala Pro Gly Lys Gly Leu Glu
        35                  40                  45

Trp Val Ser Phe Ile Asn Glu Asp Gly Gly Asn Ile Tyr Tyr Gly Asp
50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Ser Gly Ser Leu Thr Phe Asp Tyr Trp Gly
            100                 105                 110

Gln Gly Thr Leu Val Thr Val Ser Ser Gly Leu Gly Leu Gly Gly
        115                 120                 125

Gly Gly Ser Gly Gly Gly Gly Ser Gly Gly Ser
    130                 135

<210> SEQ ID NO 45
<211> LENGTH: 139
<212> TYPE: PRT
<213> ORGANISM: Artificial Sequence
<220> FEATURE:
<223> OTHER INFORMATION: VEGF B12 heavy chain

<400> SEQUENCE: 45

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
            20                  25                  30

Ser Tyr Ala Ile Ser Trp Val Arg Gln Ala Pro Gly Gln Gly Leu Glu
        35                  40                  45

Trp Met Gly Gly Ile Ile Pro Ile Phe Gly Thr Ala Asn Tyr Ala Gln
 50                  55                  60

Lys Phe Gln Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                85                  90                  95

Tyr Cys Ala Arg Asp Arg Ser Gly Tyr Thr Ala Met Asp Tyr Trp Gly
            100                 105                 110

Gln Gly Thr Leu Val Thr Val Ser Ser Gly Leu Gly Gly Leu Gly Gly
            115                 120                 125

Gly Gly Ser Gly Gly Gly Gly Ser Gly Gly Ser
            130                 135

<210> SEQ ID NO 46
<211> LENGTH: 140
<212> TYPE: PRT
<213> ORGANISM: Artificial Sequence
<220> FEATURE:
<223> OTHER INFORMATION: VEGF C11 heavy chain

<400> SEQUENCE: 46

Met Ala Gln Met Gln Leu Val Gln Ser Gly Ala Glu Val Lys Lys Pro
 1               5                  10                  15

Gly Ser Ser Val Lys Val Ser Cys Lys Ala Ser Gly Gly Thr Phe Ser
                20                  25                  30

Ser Asp Ala Ile Ser Trp Val Arg Gln Ala Pro Gly Gln Gly Leu Glu
        35                  40                  45

Trp Met Gly Gly Val Ile Pro Ile Phe Ala Thr Thr Thr Tyr Ala Gln
 50                  55                  60

Gly Phe Gln Gly Arg Leu Thr Ile Thr Ala Asp Thr Ser Thr Arg Thr
 65                  70                  75                  80

Ala Tyr Met Glu Leu Thr Asn Leu Arg Ser Glu Asp Thr Ala Val Tyr
                85                  90                  95

Tyr Cys Ala Arg Gly Gln Met Asp Arg Gly Gly Leu Asp Pro Trp
            100                 105                 110

Gly Gln Gly Thr Leu Val Thr Val Ser Ser Gly Leu Gly Gly Leu Gly
            115                 120                 125

Gly Gly Gly Ser Gly Gly Gly Gly Ser Gly Gly Ser
            130                 135                 140

<210> SEQ ID NO 47
<211> LENGTH: 138
<212> TYPE: PRT
<213> ORGANISM: Artificial Sequence
<220> FEATURE:
<223> OTHER INFORMATION: VEGF C12 heavy chain

<400> SEQUENCE: 47

Met Ala Gln Met Gln Leu Val Glu Ser Gly Gly Gly Leu Val Lys Pro
 1               5                  10                  15

Gly Gly Ser Leu Arg Leu Ser Cys Ala Ala Ser Gly Phe Ser Phe Ser
                20                  25                  30

Ser Tyr Gly Met Asn Trp Val Arg Gln Ala Pro Gly Lys Gly Leu Glu
        35                  40                  45

Trp Val Ser Ser Ile Ser Ser Ser Ser Ser Ile His Tyr Ala Asp
 50                  55                  60

```
Ser Val Lys Gly Arg Phe Ser Ile Ser Arg Asp Asn Ala Lys Asn Ser
 65                  70                  75                  80

Val Tyr Leu Gln Met Asn Ser Leu Arg Ala Glu Asp Thr Ala Val Tyr
                 85                  90                  95

Tyr Cys Ala Arg Leu Gly Pro Tyr Asp Ala Phe Asp Phe Trp Gly Gln
            100                 105                 110

Gly Thr Val Val Thr Val Ser Ser Gly Leu Gly Gly Leu Gly Gly Gly
            115                 120                 125

Gly Ser Gly Gly Gly Gly Ser Gly Gly Ser
    130                 135
```

<210> SEQ ID NO 48
<211> LENGTH: 143
<212> TYPE: PRT
<213> ORGANISM: Artificial Sequence
<220> FEATURE:
<223> OTHER INFORMATION: VEGF C5 heavy chain

<400> SEQUENCE: 48

```
Met Ala Gln Val Gln Leu Val Glu Ser Gly Gly Gly Val Val Gln Pro
  1               5                  10                  15

Gly Arg Ser Leu Arg Leu Ser Cys Ala Ala Ser Gly Phe Thr Phe Thr
                 20                  25                  30

Ser Tyr Ser Met His Trp Val Arg Gln Ala Pro Gly Lys Gly Leu Glu
             35                  40                  45

Trp Val Ala Gly Ile Ser Tyr Asp Gly Ser Ser Lys Gln Phe Gly Asp
 50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Gly Val Pro Gly His Ser Tyr Gly Ile Gly Met
            100                 105                 110

Asp Val Trp Gly Gln Gly Thr Thr Val Thr Val Ser Ser Gly Leu Gly
            115                 120                 125

Gly Leu Gly Gly Gly Gly Ser Gly Gly Gly Gly Ser Gly Gly Ser
    130                 135                 140
```

<210> SEQ ID NO 49
<211> LENGTH: 141
<212> TYPE: PRT
<213> ORGANISM: Artificial Sequence
<220> FEATURE:
<223> OTHER INFORMATION: VEGF C9 heavy chain

<400> SEQUENCE: 49

```
Met Ala Gln Val Gln Leu Val Lys Ser Glu Gly Gly Val Val Gln Pro
  1               5                  10                  15

Gly Arg Ser Leu Arg Leu Ser Cys Ala Ala Ser Gly Phe Thr Phe Ser
                 20                  25                  30

Ser Tyr Ala Met His Trp Val Arg Gln Ala Pro Gly Lys Gly Leu Glu
             35                  40                  45

Trp Val Ala Val Ile Ser Tyr Asp Gly Ser Asn Lys Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95
```

Tyr Cys Ala Lys Asp Val Asp Ser Trp Ser Gln Gly Trp Phe Pro His
            100                 105                 110

Trp Gly Gln Gly Thr Leu Val Thr Val Ser Ser Gly Leu Gly Gly Leu
            115                 120                 125

Gly Gly Gly Gly Ser Gly Gly Gly Ser Gly Gly Ser
        130                 135                 140

<210> SEQ ID NO 50
<211> LENGTH: 141
<212> TYPE: PRT
<213> ORGANISM: Artificial Sequence
<220> FEATURE:
<223> OTHER INFORMATION: VEGF D12 heavy chain

<400> SEQUENCE: 50

Met Ala Gln Met Gln Leu Val Glu Ser Gly Gly Val Val Gln Pro
1               5                   10                  15

Gly Gly Ser Leu Arg Leu Ser Cys Ala Ala Ser Gly Phe Ser Phe Asp
            20                  25                  30

Glu Tyr Ala Met His Trp Val Arg Gln Ala Pro Gly Lys Gly Leu Glu
        35                  40                  45

Trp Val Ser Leu Ile Ser Gly Asp Asp Tyr Asn Thr Phe Tyr Ala Asp
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Lys Asp Ala Gly Pro Ala Gly Gly Gly Leu Asp His
            100                 105                 110

Trp Gly Gln Gly Thr Leu Val Thr Val Ser Ser Gly Leu Gly Gly Leu
            115                 120                 125

Gly Gly Gly Gly Ser Gly Gly Gly Ser Gly Gly Ser
        130                 135                 140

<210> SEQ ID NO 51
<211> LENGTH: 138
<212> TYPE: PRT
<213> ORGANISM: Artificial Sequence
<220> FEATURE:
<223> OTHER INFORMATION: VEGF E9 & VEGF F6 heavy chain

<400> SEQUENCE: 51

Met Ala Gln Val Thr Leu Arg Glu Ser Gly Pro Thr Met Val Lys Pro
1               5                   10                  15

Thr Gln Thr Leu Thr Leu Thr Cys Thr Phe Ser Gly Phe Ser Leu Ser
            20                  25                  30

Thr Ser Gly Val Ala Val Gly Trp Ile Arg Gln Pro Pro Gly Gln Ala
        35                  40                  45

Leu Glu Trp Leu Ala Leu Ile Tyr Trp Asp Asn Asp Lys Arg Tyr Ser
    50                  55                  60

Pro Ser Leu Lys Asn Arg Leu Thr Val Ala Lys Asp Thr Ser Lys Ser
65                  70                  75                  80

Gln Val Val Leu Thr Met Thr Asn Met Asp Pro Met Asp Thr Ala Thr
                85                  90                  95

Tyr Tyr Cys Ala His Gly Asp Gly Trp Leu Phe Asp Phe Trp Gly Gln
            100                 105                 110

Gly Thr Leu Val Thr Val Ser Ser Gly Leu Gly Gly Leu Gly Gly Gly
            115                 120                 125

Gly Ser Gly Gly Gly Ser Gly Gly Ser
    130                 135

<210> SEQ ID NO 52
<211> LENGTH: 140
<212> TYPE: PRT
<213> ORGANISM: Artificial Sequence
<220> FEATURE:
<223> OTHER INFORMATION: VEGF F2 heavy chain

<400> SEQUENCE: 52

Met Ala Gln Val Gln Leu Val Glu Ser Gly Gly Leu Val Gln Pro
1               5                   10                  15

Gly Gly Ser Leu Arg Leu Ser Cys Ala Ala Ser Gly Phe Ser Phe Asn
            20                  25                  30

Ser Tyr Ala Met Ser Trp Ile Arg Gln Ala Pro Gly Lys Gly Leu Glu
        35                  40                  45

Trp Val Ser Tyr Ile Ser Ser Ser Gly His Asp Ile Tyr Tyr Ala Asp
    50                  55                  60

Pro Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Asp Lys Leu Ala Thr Pro Gly Ala Phe Asp Ile Trp
            100                 105                 110

Gly Gln Gly Thr Met Val Thr Val Ser Ser Gly Leu Gly Gly Leu Gly
        115                 120                 125

Gly Gly Gly Ser Gly Gly Gly Gly Ser Gly Gly Ser
    130                 135                 140

<210> SEQ ID NO 53
<211> LENGTH: 142
<212> TYPE: PRT
<213> ORGANISM: Artificial Sequence
<220> FEATURE:
<223> OTHER INFORMATION: VEGF F9 heavy chain

<400> SEQUENCE: 53

Met Ala Gln Val Gln Leu Val Lys Ser Gly Ala Glu Val Lys Lys Pro
1               5                   10                  15

Gly Ser Ser Val Lys Val Ser Cys Lys Ala Ser Gly Gly Thr Phe Arg
            20                  25                  30

Thr Thr Ala Ile Thr Trp Val Arg Gln Ala Pro Gly Gln Ala Leu Glu
        35                  40                  45

Trp Val Gly Trp Ile Thr Pro Phe Asn Gly Asn Thr Phe Tyr Ala Gln
    50                  55                  60

Lys Phe Gln Asp Arg Val Thr Ile Thr Arg Asp Arg Ser Met Ser Thr
65                  70                  75                  80

Ala Tyr Met Glu Leu Ser Ser Leu Arg Ser Glu Asp Thr Ala Val Tyr
                85                  90                  95

Tyr Cys Ala Lys Ser Gln Ala Ala Glu Leu Gly Thr Gly Ala Phe Asp
            100                 105                 110

Ile Trp Gly Gln Gly Thr Leu Val Thr Val Ser Ser Gly Leu Gly Gly
        115                 120                 125

Leu Gly Gly Gly Gly Ser Gly Gly Gly Gly Ser Gly Gly Ser
    130                 135                 140

<210> SEQ ID NO 54

```
<211> LENGTH: 139
<212> TYPE: PRT
<213> ORGANISM: Artificial Sequence
<220> FEATURE:
<223> OTHER INFORMATION: VEGF G12 heavy chain

<400> SEQUENCE: 54

Met Ala Gln Val Gln Leu Val Gln Ser Gly Ala Glu Val Lys Lys Pro
1               5                   10                  15

Gly Ser Ser Val Lys Val Ser Cys Thr Ala Ala Gly Gly Thr Phe Asn
            20                  25                  30

Asn Tyr Ala Ile Ser Trp Leu Arg Gln Ala Pro Gly Gln Gly Leu Glu
        35                  40                  45

Trp Met Gly Arg Ile Ile Pro Ile Tyr Gly Thr Pro Thr Tyr Ala Gln
    50                  55                  60

Lys Phe Arg Asp Arg Val Thr Ile Thr Ala Asp Glu Ser Thr Ser Thr
65                  70                  75                  80

Ala Tyr Met Glu Leu Ser Asn Leu Arg Ser Glu Asp Thr Ala Val Tyr
                85                  90                  95

Tyr Cys Ala Arg Glu Arg Ser Phe Trp Asn Trp Phe Ala Pro Trp Gly
            100                 105                 110

Gln Gly Thr Leu Ile Thr Val Ser Ser Gly Leu Gly Gly Leu Gly Gly
        115                 120                 125

Gly Gly Ser Gly Gly Gly Gly Ser Gly Gly Ser
    130                 135

<210> SEQ ID NO 55
<211> LENGTH: 138
<212> TYPE: PRT
<213> ORGANISM: Artificial Sequence
<220> FEATURE:
<223> OTHER INFORMATION: VEGF G9 heavy chain

<400> SEQUENCE: 55

Met Ala Gln Val Gln Leu Val Glu Ser Gly Gly Gly Val Val Gln Pro
1               5                   10                  15

Gly Arg Ser Leu Thr Leu Ser Cys Ala Ala Ser Gly Phe Thr Phe Ser
            20                  25                  30

Thr Tyr Ala Leu His Trp Val Arg Gln Ala Pro Gly Lys Gly Leu Glu
        35                  40                  45

Trp Val Ala Val Ile Ser His Asp Gly Thr Thr Asp Tyr Tyr Arg Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ser Arg Asp Gly Ser Gly Tyr Phe Phe Asp Tyr Trp Gly Pro
            100                 105                 110

Gly Thr Gln Val Thr Val Ser Ser Gly Leu Gly Gly Leu Gly Gly Gly
        115                 120                 125

Gly Ser Gly Gly Gly Gly Ser Gly Gly Ser
    130                 135

<210> SEQ ID NO 56
<211> LENGTH: 141
<212> TYPE: PRT
<213> ORGANISM: Artificial Sequence
<220> FEATURE:
<223> OTHER INFORMATION: VEGF H7 heavy chain
```

<400> SEQUENCE: 56

Met Ala Gln Met Gln Leu Val Lys Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Lys Tyr Gly Met His Trp Val Arg Gln Ala Pro Gly Lys Gly Leu Glu
        35                  40                  45

Trp Leu Ala Phe Ile Trp Phe Asp Gly Ser Asn Lys Phe Tyr Ala Asp
    50                  55                  60

Ser Val Lys Gly Arg Phe Thr Val Ser Arg Asp Asn Ser Lys Asn Thr
65              70                  75                  80

Leu Phe Leu Gln Met Asn Ser Leu Arg Ala Glu Asp Thr Ala Val Tyr
                85                  90                  95

Tyr Cys Ala Lys Asp Arg Asp Tyr Tyr Gly Ser Gly Pro Leu Asp Tyr
            100                 105                 110

Trp Gly Gln Gly Thr Gln Ile Thr Val Ser Ser Gly Leu Gly Leu
        115                 120                 125

Gly Gly Gly Gly Ser Gly Gly Gly Ser Gly Gly Ser
    130                 135                 140

<210> SEQ ID NO 57
<211> LENGTH: 11
<212> TYPE: PRT
<213> ORGANISM: Artificial Sequence
<220> FEATURE:
<223> OTHER INFORMATION: A4 LC-CDR1

<400> SEQUENCE: 57

Arg Ala Ser Gln Thr Ile Ser Ser Tyr Leu Asn
1               5                   10

<210> SEQ ID NO 58
<211> LENGTH: 11
<212> TYPE: PRT
<213> ORGANISM: Artificial Sequence
<220> FEATURE:
<223> OTHER INFORMATION: B12 LC-CDR1

<400> SEQUENCE: 58

Arg Ala Ser Gln Gly Ile Ser Ser Tyr Leu Ala
1               5                   10

<210> SEQ ID NO 59
<211> LENGTH: 11
<212> TYPE: PRT
<213> ORGANISM: Artificial Sequence
<220> FEATURE:
<223> OTHER INFORMATION: C11 LC-CDR1

<400> SEQUENCE: 59

Arg Ala Ser Gln Gly Ile Gly Asn Tyr Leu Asn
1               5                   10

<210> SEQ ID NO 60
<211> LENGTH: 13
<212> TYPE: PRT
<213> ORGANISM: Artificial Sequence
<220> FEATURE:
<223> OTHER INFORMATION: C12 LC-CDR1

<400> SEQUENCE: 60

Pro Gly Gly Thr Ser Asn Ile Asp Ser Lys Tyr Val His
1               5                   10

```
<210> SEQ ID NO 61
<211> LENGTH: 11
<212> TYPE: PRT
<213> ORGANISM: Artificial Sequence
<220> FEATURE:
<223> OTHER INFORMATION: C5 LC-CDR1

<400> SEQUENCE: 61

Arg Ala Ser Gln Gly Ile Ser Ser Trp Leu Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: C9 LC-CDR1

<400> SEQUENCE: 62

Arg Ala Ser Gln Thr Ile Ser Thr Phe Val Asn
1               5                   10

<210> SEQ ID NO 63
<211> LENGTH: 11
<212> TYPE: PRT
<213> ORGANISM: Artificial Sequence
<220> FEATURE:
<223> OTHER INFORMATION: D12 LC-CDR1

<400> SEQUENCE: 63

Arg Thr Ser Gln Thr Ile Thr Asn Phe Leu Asn
1               5                   10

<210> SEQ ID NO 64
<211> LENGTH: 14
<212> TYPE: PRT
<213> ORGANISM: Artificial Sequence
<220> FEATURE:
<223> OTHER INFORMATION: E9 & F6 LC-CDR1

<400> SEQUENCE: 64

Thr Gly Ser Asn Ser Asn Ile Gly Ala Gly His Asp Val His
1               5                   10

<210> SEQ ID NO 65
<211> LENGTH: 11
<212> TYPE: PRT
<213> ORGANISM: Artificial Sequence
<220> FEATURE:
<223> OTHER INFORMATION: F2 LC-CDR1

<400> SEQUENCE: 65

Arg Ala Ser Gln Ser Ile Ser Asn Trp Leu Ala
1               5                   10

<210> SEQ ID NO 66
<211> LENGTH: 13
<212> TYPE: PRT
<213> ORGANISM: Artificial Sequence
<220> FEATURE:
<223> OTHER INFORMATION: F9 LC-CDR1

<400> SEQUENCE: 66

Ser Gly Ser Tyr Ser Asn Ile Gly Thr Asn Tyr Val Tyr
1               5                   10
```

```
<210> SEQ ID NO 67
<211> LENGTH: 14
<212> TYPE: PRT
<213> ORGANISM: Artificial Sequence
<220> FEATURE:
<223> OTHER INFORMATION: G12, 2A09 & 2E11 LC-CDR1

<400> SEQUENCE: 67

Thr Gly Ser Ser Ser Asn Ile Gly Ala Gly Tyr Asp Val His
1               5                   10

<210> SEQ ID NO 68
<211> LENGTH: 14
<212> TYPE: PRT
<213> ORGANISM: Artificial Sequence
<220> FEATURE:
<223> OTHER INFORMATION: G9 LC-CDR1

<400> SEQUENCE: 68

Thr Gly Ser Ser Ser Asp Val Gly Gly Tyr Asn Tyr Val Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: H7 LC-CDR1

<400> SEQUENCE: 69

Arg Ala Ser Gln Arg Ile Ala Thr Tyr Leu His
1               5                   10

<210> SEQ ID NO 70
<211> LENGTH: 7
<212> TYPE: PRT
<213> ORGANISM: Artificial Sequence
<220> FEATURE:
<223> OTHER INFORMATION: A4 LC-CDR2

<400> SEQUENCE: 70

Ala Ala Ser Arg Leu Gln Ser
1               5

<210> SEQ ID NO 71
<211> LENGTH: 7
<212> TYPE: PRT
<213> ORGANISM: Artificial Sequence
<220> FEATURE:
<223> OTHER INFORMATION: B12 LC-CDR2

<400> SEQUENCE: 71

Ala Ala Ser Thr Leu Gln Ser
1               5

<210> SEQ ID NO 72
<211> LENGTH: 7
<212> TYPE: PRT
<213> ORGANISM: Artificial Sequence
<220> FEATURE:
<223> OTHER INFORMATION: C11 LC-CDR2

<400> SEQUENCE: 72

Ala Ala Ser Ser Leu Gln Arg
1               5

<210> SEQ ID NO 73
<211> LENGTH: 7
```

```
<212> TYPE: PRT
<213> ORGANISM: Artificial Sequence
<220> FEATURE:
<223> OTHER INFORMATION: C12 LC-CDR2

<400> SEQUENCE: 73

Arg Asn Asp Gln Arg Pro Ser
1               5

<210> SEQ ID NO 74
<211> LENGTH: 7
<212> TYPE: PRT
<213> ORGANISM: Artificial Sequence
<220> FEATURE:
<223> OTHER INFORMATION: C5 LC-CDR2

<400> SEQUENCE: 74

Ala Ala Ser Ile Leu Gln Thr
1               5

<210> SEQ ID NO 75
<211> LENGTH: 7
<212> TYPE: PRT
<213> ORGANISM: Artificial Sequence
<220> FEATURE:
<223> OTHER INFORMATION: C9 LC-CDR2

<400> SEQUENCE: 75

Ser Ala Ser Ser Leu Gln Ser
1               5

<210> SEQ ID NO 76
<211> LENGTH: 7
<212> TYPE: PRT
<213> ORGANISM: Artificial Sequence
<220> FEATURE:
<223> OTHER INFORMATION: D12 LC-CDR2

<400> SEQUENCE: 76

Gly Ala Ser Ser Leu Gln Ser
1               5

<210> SEQ ID NO 77
<211> LENGTH: 7
<212> TYPE: PRT
<213> ORGANISM: Artificial Sequence
<220> FEATURE:
<223> OTHER INFORMATION: E9 & F6 LC-CDR2

<400> SEQUENCE: 77

Gly Asn Thr Asn Arg Ala Ser
1               5

<210> SEQ ID NO 78
<211> LENGTH: 7
<212> TYPE: PRT
<213> ORGANISM: Artificial Sequence
<220> FEATURE:
<223> OTHER INFORMATION: F2 LC-CDR2

<400> SEQUENCE: 78

Glu Ala Ser Ser Leu Glu Ser
1               5

<210> SEQ ID NO 79
<211> LENGTH: 7
<212> TYPE: PRT
<213> ORGANISM: Artificial Sequence
```

<220> FEATURE:
<223> OTHER INFORMATION: F9 LC-CDR2

<400> SEQUENCE: 79

Lys Asn Thr Gln Arg Pro Ser
1               5

<210> SEQ ID NO 80
<211> LENGTH: 7
<212> TYPE: PRT
<213> ORGANISM: Artificial Sequence
<220> FEATURE:
<223> OTHER INFORMATION: G12, 2E11, 2G04 & 2G12 LC-CDR2

<400> SEQUENCE: 80

Gly Asn Asn Asn Arg Pro Ser
1               5

<210> SEQ ID NO 81
<211> LENGTH: 7
<212> TYPE: PRT
<213> ORGANISM: Artificial Sequence
<220> FEATURE:
<223> OTHER INFORMATION: G9 LC-CDR2

<400> SEQUENCE: 81

Asp Val Thr Lys Arg Pro Ser
1               5

<210> SEQ ID NO 82
<211> LENGTH: 7
<212> TYPE: PRT
<213> ORGANISM: Artificial Sequence
<220> FEATURE:
<223> OTHER INFORMATION: H7 LC-CDR2

<400> SEQUENCE: 82

Ala Ala Ser Ser Leu Gln Ser
1               5

<210> SEQ ID NO 83
<211> LENGTH: 9
<212> TYPE: PRT
<213> ORGANISM: Artificial Sequence
<220> FEATURE:
<223> OTHER INFORMATION: A4 & H7 LC-CDR3

<400> SEQUENCE: 83

Gln Gln Ser Tyr Ser Thr Pro Tyr Thr
1               5

<210> SEQ ID NO 84
<211> LENGTH: 9
<212> TYPE: PRT
<213> ORGANISM: Artificial Sequence
<220> FEATURE:
<223> OTHER INFORMATION: B12 LC-CDR3

<400> SEQUENCE: 84

Gln Gln Gly His Thr Thr Pro Tyr Thr
1               5

<210> SEQ ID NO 85
<211> LENGTH: 9
<212> TYPE: PRT
<213> ORGANISM: Artificial Sequence
<220> FEATURE:
<223> OTHER INFORMATION: C11 LC-CDR3

```
<400> SEQUENCE: 85

Gln Gln Ser Tyr Thr Thr Pro Tyr Ser
1               5

<210> SEQ ID NO 86
<211> LENGTH: 12
<212> TYPE: PRT
<213> ORGANISM: Artificial Sequence
<220> FEATURE:
<223> OTHER INFORMATION: C12 LC-CDR3

<400> SEQUENCE: 86

Gln Ser Tyr Asp Thr Ser Leu Ser Ala Pro Tyr Val
1               5                   10

<210> SEQ ID NO 87
<211> LENGTH: 9
<212> TYPE: PRT
<213> ORGANISM: Artificial Sequence
<220> FEATURE:
<223> OTHER INFORMATION: C5 LC-CDR3

<400> SEQUENCE: 87

Gln Gln Ala Asn Ser Phe Pro Tyr Thr
1               5

<210> SEQ ID NO 88
<211> LENGTH: 9
<212> TYPE: PRT
<213> ORGANISM: Artificial Sequence
<220> FEATURE:
<223> OTHER INFORMATION: C9 LC-CDR3

<400> SEQUENCE: 88

Gln Gln Asn Tyr Ser Thr Pro Leu Thr
1               5

<210> SEQ ID NO 89
<211> LENGTH: 9
<212> TYPE: PRT
<213> ORGANISM: Artificial Sequence
<220> FEATURE:
<223> OTHER INFORMATION: D12 & F2 LC-CDR3

<400> SEQUENCE: 89

Gln Gln Ser His Gly Thr Pro Tyr Thr
1               5

<210> SEQ ID NO 90
<211> LENGTH: 11
<212> TYPE: PRT
<213> ORGANISM: Artificial Sequence
<220> FEATURE:
<223> OTHER INFORMATION: E9 & F6 LC-CDR3

<400> SEQUENCE: 90

Gln Ser Tyr Asp Asn Ser Leu Ser Gly Tyr Val
1               5                   10

<210> SEQ ID NO 91
<211> LENGTH: 11
<212> TYPE: PRT
<213> ORGANISM: Artificial Sequence
<220> FEATURE:
<223> OTHER INFORMATION: F9 LC-CDR3

<400> SEQUENCE: 91
```

Ser Ala Trp Asp Asp Ser Leu Ser Ala Val Leu
1               5                   10

<210> SEQ ID NO 92
<211> LENGTH: 10
<212> TYPE: PRT
<213> ORGANISM: Artificial Sequence
<220> FEATURE:
<223> OTHER INFORMATION: G12 LC-CDR3

<400> SEQUENCE: 92

Gln Ser Tyr Asp Ser Arg Leu Gly Val Val
1               5                   10

<210> SEQ ID NO 93
<211> LENGTH: 10
<212> TYPE: PRT
<213> ORGANISM: Artificial Sequence
<220> FEATURE:
<223> OTHER INFORMATION: G9 LC-CDR3

<400> SEQUENCE: 93

Ser Ser Tyr Ser Ser Ser Thr Phe Tyr Val
1               5                   10

<210> SEQ ID NO 94
<211> LENGTH: 130
<212> TYPE: PRT
<213> ORGANISM: Artificial Sequence
<220> FEATURE:
<223> OTHER INFORMATION: VEGF A4 light chain

<400> SEQUENCE: 94

Gly Val Gly Ser Asp Ile Gln Met Thr Gln Ser Pro Ser Ser Leu Pro
1               5                   10                  15

Ala Ser Val Gly Asp Thr Val Thr Ile Ser Cys Arg Ala Ser Gln Thr
            20                  25                  30

Ile Ser Ser Tyr Leu Asn Trp Tyr Gln Gln Lys Pro Gly Lys Ala Pro
        35                  40                  45

Lys Leu Leu Ile Tyr Ala Ala Ser Arg Leu Gln Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Thr Pro Tyr Thr Phe Gly Gln Gly Thr Lys Val Asp Ile Lys Arg
            100                 105                 110

Gly Gly Ala Ser Leu Val Glu Phe Glu Gln Lys Leu Ile Ser Glu Glu
        115                 120                 125

Asp Leu
    130

<210> SEQ ID NO 95
<211> LENGTH: 130
<212> TYPE: PRT
<213> ORGANISM: Artificial Sequence
<220> FEATURE:
<223> OTHER INFORMATION: VEGF B12 light chain

<400> SEQUENCE: 95

Gly Val Gly Ser Asp Ile Gln Met Thr Gln Ser Pro Ser Ser Leu Ser
1               5                   10                  15

```
Ala Ser Val Gly Asp Arg Val Thr Ile Thr Cys Arg Ala Ser Gln Gly
            20                  25                  30

Ile Ser Ser Tyr Leu Ala Trp Tyr Gln Gln Lys Pro Gly Lys Ala Pro
        35                  40                  45

Lys Leu Leu Ile Tyr Ala Ala Ser Thr Leu Gln Ser Gly Val Pro Ser
 50                  55                  60

Arg Phe Ser Gly Ser Gly Ser Gly Ser His Phe Thr Leu Thr Ile Thr
 65                  70                  75                  80

Asn Leu Gln Pro Glu Asp Phe Ala Thr Tyr Tyr Cys Gln Gln Gly His
                85                  90                  95

Thr Thr Pro Tyr Thr Phe Gly Gln Gly Thr Lys Leu Glu Ile Lys Arg
            100                 105                 110

Gly Gly Ala Ser Leu Val Glu Phe Glu Gln Lys Leu Ile Ser Glu Glu
        115                 120                 125

Asp Leu
    130
```

<210> SEQ ID NO 96
<211> LENGTH: 130
<212> TYPE: PRT
<213> ORGANISM: Artificial Sequence
<220> FEATURE:
<223> OTHER INFORMATION: VEGF C11 light chain

<400> SEQUENCE: 96

```
Gly Val Gly Ser Asp Ile Gln Met Thr Gln Ser Pro Ser Ser Leu Ser
 1               5                  10                  15

Ala Ser Val Gly Asp Arg Val Thr Ile Thr Cys Arg Ala Ser Gln Gly
            20                  25                  30

Ile Gly Asn Tyr Leu Asn Trp Tyr Gln Gln Lys Pro Gly Lys Ala Pro
        35                  40                  45

Lys Leu Leu Val Tyr Ala Ala Ser Ser Leu Gln Arg Gly Val Pro Ser
 50                  55                  60

Arg Phe Ser Gly Arg Gly Ser Gly Thr Asp Phe Thr Leu Thr Ile Ser
 65                  70                  75                  80

Gly Leu Gln Pro Asp Asp Phe Ala Leu Tyr Tyr Cys Gln Gln Ser Tyr
                85                  90                  95

Thr Thr Pro Tyr Ser Phe Gly Pro Gly Thr Lys Val Glu Ile Lys Arg
            100                 105                 110

Gly Gly Ala Ser Leu Val Glu Phe Glu Gln Lys Leu Ile Ser Glu Glu
        115                 120                 125

Asp Leu
    130
```

<210> SEQ ID NO 97
<211> LENGTH: 134
<212> TYPE: PRT
<213> ORGANISM: Artificial Sequence
<220> FEATURE:
<223> OTHER INFORMATION: VEGF C12 light chain

<400> SEQUENCE: 97

```
Gly Val Gly Ser Gln Leu Val Leu Thr Gln Pro Pro Ser Val Ser Gly
 1               5                  10                  15

Thr Pro Gly Gln Arg Val Thr Ile Ser Cys Pro Gly Gly Thr Ser Asn
            20                  25                  30

Ile Asp Ser Lys Tyr Val His Trp Tyr Gln Gln Leu Pro Gly Thr Ala
        35                  40                  45
```

```
Pro Lys Leu Leu Ile Tyr Arg Asn Asp Gln Arg Pro Ser Gly Val Pro
        50                  55                  60

Asp Arg Phe Ser Gly Ser Lys Ser Gly Thr Ser Ala Ser Leu Ala Ile
 65                  70                  75                  80

Thr Gly Leu Gln Ala Ala Asp Glu Ala Ala Tyr Tyr Cys Gln Ser Tyr
                 85                  90                  95

Asp Thr Ser Leu Ser Ala Pro Tyr Val Phe Gly Thr Gly Thr Lys Val
            100                 105                 110

Thr Val Leu Gly Gly Gly Ala Ser Leu Val Glu Phe Glu Gln Lys Leu
        115                 120                 125

Ile Ser Glu Glu Asp Leu
    130
```

<210> SEQ ID NO 98
<211> LENGTH: 130
<212> TYPE: PRT
<213> ORGANISM: Artificial Sequence
<220> FEATURE:
<223> OTHER INFORMATION: VEGF C5 light chain

<400> SEQUENCE: 98

```
Gly Val Gly Ser Asp Ile Gln Met Thr Gln Ser Pro Ser Ser Val Ser
 1               5                  10                  15

Ala Ser Val Gly Asp Arg Val Thr Ile Thr Cys Arg Ala Ser Gln Gly
             20                  25                  30

Ile Ser Ser Trp Leu Ala Trp Tyr Gln Gln Lys Pro Gly Lys Ala Pro
         35                  40                  45

Lys Leu Leu Ile Tyr Ala Ala Ser Ile Leu Gln Thr Gly Val Pro Ser
     50                  55                  60

Arg Phe Ser Gly Ser Gly Ser Gly Thr Asp Phe Thr Leu Thr Ile Asn
 65                  70                  75                  80

Ser Leu Gln Ser Asp Asp Phe Ala Thr Tyr Tyr Cys Gln Gln Ala Asn
                 85                  90                  95

Ser Phe Pro Tyr Thr Phe Gly Gln Gly Thr Lys Val Glu Ile Lys Arg
            100                 105                 110

Gly Gly Ala Ser Leu Val Glu Phe Glu Gln Lys Leu Ile Ser Glu Glu
        115                 120                 125

Asp Leu
    130
```

<210> SEQ ID NO 99
<211> LENGTH: 130
<212> TYPE: PRT
<213> ORGANISM: Artificial Sequence
<220> FEATURE:
<223> OTHER INFORMATION: VEGF C9 light chain

<400> SEQUENCE: 99

```
Gly Val Gly Ser Asp Ile Gln Met Thr Gln Ser Pro Ser Ser Leu Ser
 1               5                  10                  15

Ala Ser Val Gly Asp Arg Val Thr Ile Thr Cys Arg Ala Ser Gln Thr
             20                  25                  30

Ile Ser Thr Phe Val Asn Trp Tyr Gln Gln Lys Pro Gly Lys Ala Pro
         35                  40                  45

Lys Leu Leu Ile Tyr Ser Ala Ser Ser Leu Gln Ser Gly Val Pro Ser
     50                  55                  60

Arg Phe Ser Gly Ser Gly Ser Gly Thr Asp Phe Thr Leu Thr Ile Asn
 65                  70                  75                  80
```

```
Ser Leu Gln Pro Glu Asp Phe Ala Thr Tyr Tyr Cys Gln Gln Asn Tyr
                85                  90                  95

Ser Thr Pro Leu Thr Phe Gly Gly Gly Thr Arg Leu Glu Ile Lys Arg
            100                 105                 110

Gly Gly Ala Ser Leu Val Glu Phe Glu Gln Lys Leu Ile Ser Glu Glu
        115                 120                 125

Asp Leu
    130

<210> SEQ ID NO 100
<211> LENGTH: 130
<212> TYPE: PRT
<213> ORGANISM: Artificial Sequence
<220> FEATURE:
<223> OTHER INFORMATION: VEGF D12 light chain

<400> SEQUENCE: 100

Gly Val Gly Ser Asp Ile Gln Met Thr Gln Ser Pro Ser Ser Leu Ser
1               5                   10                  15

Ala Ser Val Gly Asp Arg Val Thr Ile Thr Cys Arg Thr Ser Gln Thr
            20                  25                  30

Ile Thr Asn Phe Leu Asn Trp Tyr Gln Gln Lys Pro Gly Lys Ala Pro
        35                  40                  45

Lys Leu Leu Ile Tyr Gly Ala Ser Ser Leu Gln Ser Gly Val Pro Ser
50                  55                  60

Arg Phe Gly Gly Ser Gly Ser Gly Thr Asp Phe Thr Leu Thr Ile Asn
65                  70                  75                  80

Ser Leu Gln Pro Glu Asp Phe Ala Thr Tyr Tyr Cys Gln Gln Ser His
                85                  90                  95

Gly Thr Pro Tyr Thr Phe Gly Gln Gly Thr Lys Leu Glu Ile Lys Arg
            100                 105                 110

Gly Gly Ala Ser Leu Val Glu Phe Glu Gln Lys Leu Ile Ser Glu Glu
        115                 120                 125

Asp Leu
    130

<210> SEQ ID NO 101
<211> LENGTH: 134
<212> TYPE: PRT
<213> ORGANISM: Artificial Sequence
<220> FEATURE:
<223> OTHER INFORMATION: VEGF E9 & VEGF F6 light chain

<400> SEQUENCE: 101

Gly Val Gly Ser Gln Leu Val Leu Thr Gln Pro Pro Ser Val Ser Gly
1               5                   10                  15

Ala Pro Gly Gln Arg Val Thr Ile Ser Cys Thr Gly Ser Asn Ser Asn
            20                  25                  30

Ile Gly Ala Gly His Asp Val His Trp Tyr Gln Gln Leu Pro Gly Ala
        35                  40                  45

Ala Pro Lys Val Val Ile Tyr Gly Asn Thr Asn Arg Ala Ser Gly Val
50                  55                  60

Pro Glu Arg Phe Ser Gly Ser Lys Ser Ala Thr Ser Ala Ser Leu Ala
65                  70                  75                  80

Ile Thr Gly Leu Gln Ala Glu Asp Glu Ala Asp Tyr Tyr Cys Gln Ser
                85                  90                  95

Tyr Asp Asn Ser Leu Ser Gly Tyr Val Phe Gly Thr Gly Thr Lys Val
            100                 105                 110
```

Thr Val Leu Gly Gly Gly Ala Ser Leu Val Glu Phe Glu Gln Lys Leu
        115                 120                 125

Ile Ser Glu Glu Asp Leu
    130

<210> SEQ ID NO 102
<211> LENGTH: 130
<212> TYPE: PRT
<213> ORGANISM: Artificial Sequence
<220> FEATURE:
<223> OTHER INFORMATION: VEGF F2 light chain

<400> SEQUENCE: 102

Gly Val Gly Ser Asp Ile Gln Met Thr Gln Ser Pro Ser Ser Leu Ser
1               5                   10                  15

Ala Ser Val Gly Asp Arg Val Ser Ile Thr Cys Arg Ala Ser Gln Ser
            20                  25                  30

Ile Ser Asn Trp Leu Ala Trp Tyr Gln Gln Lys Pro Gly Lys Ala Pro
        35                  40                  45

Lys Leu Leu Ile Tyr Glu Ala Ser Ser Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Ser Tyr Phe Cys Gln Gln Ser His
                85                  90                  95

Gly Thr Pro Tyr Thr Phe Gly Gln Gly Thr Lys Leu Glu Ile Lys Arg
            100                 105                 110

Gly Gly Ala Ser Leu Val Glu Phe Glu Gln Lys Leu Ile Ser Glu Glu
        115                 120                 125

Asp Leu
    130

<210> SEQ ID NO 103
<211> LENGTH: 133
<212> TYPE: PRT
<213> ORGANISM: Artificial Sequence
<220> FEATURE:
<223> OTHER INFORMATION: VEGF F9 light chain

<400> SEQUENCE: 103

Gly Val Gly Ser Gln Leu Val Leu Thr Gln Pro Ser Ser Val Ser Gly
1               5                   10                  15

Thr Pro Gly Gln Arg Val Thr Ile Ser Cys Ser Gly Ser Tyr Ser Asn
            20                  25                  30

Ile Gly Thr Asn Tyr Val Tyr Trp Tyr His Gln Leu Pro Gly Thr Ala
        35                  40                  45

Pro Lys Leu Val Ile Gln Lys Asn Thr Gln Arg Pro Ser Gly Val Ser
    50                  55                  60

Asp Arg Phe Ser Gly Ser Arg Ser Gly Thr Ser Ala Ser Leu Ala Ile
65                  70                  75                  80

Ser Gly Leu Arg Ser Glu Asp Glu Gly Asn Tyr Phe Cys Ser Ala Trp
                85                  90                  95

Asp Asp Ser Leu Ser Ala Val Leu Phe Gly Gly Gly Thr Lys Leu Thr
            100                 105                 110

Val Leu Gly Gly Gly Ala Ser Leu Val Glu Phe Glu Gln Lys Leu Ile
        115                 120                 125

Ser Glu Glu Asp Leu
    130

<210> SEQ ID NO 104
<211> LENGTH: 133
<212> TYPE: PRT
<213> ORGANISM: Artificial Sequence
<220> FEATURE:
<223> OTHER INFORMATION: VEGF G12 light chain

<400> SEQUENCE: 104

Gly Val Gly Ser Gln Leu Val Leu Thr Gln Pro Pro Ser Val Ser Gly
1               5                   10                  15

Ala Pro Gly Gln Arg Val Ile Ile Ser Cys Thr Gly Ser Ser Ser Asn
            20                  25                  30

Ile Gly Ala Gly Tyr Asp Val His Trp Tyr Gln Gln Leu Pro Gly Thr
        35                  40                  45

Ala Pro Lys Leu Leu Ile Tyr Gly Asn Asn Asn Arg Pro Ser Gly Val
    50                  55                  60

Pro Asp Arg Phe Ser Gly Ser Lys Ser Gly Thr Ser Ala Ser Leu Ala
65                  70                  75                  80

Ile Thr Gly Leu Gln Ala Glu Asp Glu Ala Asp Tyr Tyr Cys Gln Ser
                85                  90                  95

Tyr Asp Ser Arg Leu Gly Val Val Phe Gly Gly Gly Thr Lys Leu Thr
            100                 105                 110

Val Leu Gly Gly Gly Ala Ser Leu Val Glu Phe Glu Gln Lys Leu Ile
        115                 120                 125

Ser Glu Glu Asp Leu
    130

<210> SEQ ID NO 105
<211> LENGTH: 133
<212> TYPE: PRT
<213> ORGANISM: Artificial Sequence
<220> FEATURE:
<223> OTHER INFORMATION: VEGF G9 light chain

<400> SEQUENCE: 105

Gly Val Gly Ser Asn Phe Met Leu Thr Gln Pro Ala Ser Val Ser Gly
1               5                   10                  15

Ser Pro Arg Gln Ser Ile Thr Ile Ser Cys Thr Gly Ser Ser Ser Asp
            20                  25                  30

Val Gly Gly Tyr Asn Tyr Val Ser Trp Tyr Gln Gln His Pro Gly Lys
        35                  40                  45

Ala Pro Gln Leu Ile Ile Tyr Asp Val Thr Lys Arg Pro Ser Gly Val
    50                  55                  60

Ser Asn Arg Phe Ser Gly Ser Lys Ser Gly Asn Ser Ala Ser Leu Thr
65                  70                  75                  80

Ile Ser Gly Leu Gln Ala Glu Asp Glu Ala Asp Tyr Tyr Cys Ser Ser
                85                  90                  95

Tyr Ser Ser Ser Thr Phe Tyr Val Phe Gly Thr Gly Thr Lys Val Thr
            100                 105                 110

Val Leu Gly Gly Gly Ala Ser Leu Val Glu Phe Glu Gln Lys Leu Ile
        115                 120                 125

Ser Glu Glu Asp Leu
    130

<210> SEQ ID NO 106
<211> LENGTH: 130
<212> TYPE: PRT
<213> ORGANISM: Artificial Sequence
<220> FEATURE:

<223> OTHER INFORMATION: VEGF H7 light chain

<400> SEQUENCE: 106

Gly Val Gly Ser Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Arg
            20                  25                  30

Ile Ala Thr Tyr Leu His Trp Tyr Gln Gln Lys Pro Gly Lys Ala Pro
        35                  40                  45

Lys Leu Leu Ile Tyr Ala Ala Ser Ser Leu Gln Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Thr Pro Tyr Thr Phe Ala Gln Gly Thr Lys Val Glu Ile Lys Arg
            100                 105                 110

Gly Gly Ala Ser Leu Val Glu Phe Glu Gln Lys Leu Ile Ser Glu Glu
        115                 120                 125

Asp Leu
    130

<210> SEQ ID NO 107
<211> LENGTH: 50
<212> TYPE: DNA
<213> ORGANISM: Artificial Sequence
<220> FEATURE:
<223> OTHER INFORMATION: NATVH7-1

<400> SEQUENCE: 107
ttggtggcca cagcggccga tgtccactcg cagatgcagc tggtggagtc        50

<210> SEQ ID NO 108
<211> LENGTH: 50
<212> TYPE: DNA
<213> ORGANISM: Artificial Sequence
<220> FEATURE:
<223> OTHER INFORMATION: NATVH3-1

<400> SEQUENCE: 108
ttggtggcca cagcggccga tgtccactcg caggtgcagc tggtggagtc        50

<210> SEQ ID NO 109
<211> LENGTH: 50
<212> TYPE: DNA
<213> ORGANISM: Artificial Sequence
<220> FEATURE:
<223> OTHER INFORMATION: NATVH1-2

<400> SEQUENCE: 109
ttggtggcca cagcggccga tgtccactcg cagatgcagc tggtgcagtc        50

<210> SEQ ID NO 110
<211> LENGTH: 50
<212> TYPE: DNA
<213> ORGANISM: Artificial Sequence
<220> FEATURE:
<223> OTHER INFORMATION: NATVH2-1

<400> SEQUENCE: 110
ttggtggcca cagcggccga tgtccactcg caggtcacct tgaaggagtc        50

```
<210> SEQ ID NO 111
<211> LENGTH: 50
<212> TYPE: DNA
<213> ORGANISM: Artificial Sequence
<220> FEATURE:
<223> OTHER INFORMATION: NATVH3-2

<400> SEQUENCE: 111
ttggtggcca cagcggccga tgtccactcg caggtgcagc tggtggagtc          50

<210> SEQ ID NO 112
<211> LENGTH: 50
<212> TYPE: DNA
<213> ORGANISM: Artificial Sequence
<220> FEATURE:
<223> OTHER INFORMATION: NATVH1-1

<400> SEQUENCE: 112
ttggtggcca cagcggccga tgtccactcg caggtgcagc tggtgcagtc          50

<210> SEQ ID NO 113
<211> LENGTH: 50
<212> TYPE: DNA
<213> ORGANISM: Artificial Sequence
<220> FEATURE:
<223> OTHER INFORMATION: NATVH7-2

<400> SEQUENCE: 113
ttggtggcca cagcggccga tgtccactcg cagatgcagc tggtaaagtc          50

<210> SEQ ID NO 114
<211> LENGTH: 26
<212> TYPE: DNA
<213> ORGANISM: Artificial Sequence
<220> FEATURE:
<223> OTHER INFORMATION: NATJH-ALL

<400> SEQUENCE: 114
gaggaggcta gctgaggaga cggtga                                    26

<210> SEQ ID NO 115
<211> LENGTH: 50
<212> TYPE: DNA
<213> ORGANISM: Artificial Sequence
<220> FEATURE:
<223> OTHER INFORMATION: NATVK1-1

<400> SEQUENCE: 115
ttggtggcca cagcggccga tgtccactcg gacatccaga tgacccagtc          50

<210> SEQ ID NO 116
<211> LENGTH: 50
<212> TYPE: DNA
<213> ORGANISM: Artificial Sequence
<220> FEATURE:
<223> OTHER INFORMATION: NATVL10

<400> SEQUENCE: 116
ttggtggcca cagcggccga tgtccactcg cagctcgtgc tgactcagcc          50

<210> SEQ ID NO 117
<211> LENGTH: 50
<212> TYPE: DNA
<213> ORGANISM: Artificial Sequence
<220> FEATURE:
<223> OTHER INFORMATION: NATVL2

<400> SEQUENCE: 117
```
ttggtggcca gcgggccga tgtccactcg cagcctgtgc tgactcagcc          50

<210> SEQ ID NO 118
<211> LENGTH: 50
<212> TYPE: DNA
<213> ORGANISM: Artificial Sequence
<220> FEATURE:
<223> OTHER INFORMATION: NATVL9

<400> SEQUENCE: 118
ttggtggcca cagcggccga tgtccactcg aattttatgc tgactcagcc          50

<210> SEQ ID NO 119
<211> LENGTH: 30
<212> TYPE: DNA
<213> ORGANISM: Artificial Sequence
<220> FEATURE:
<223> OTHER INFORMATION: NATJK-R7

<400> SEQUENCE: 119
gaggagagat cttttgatat ccaccttggt          30

<210> SEQ ID NO 120
<211> LENGTH: 31
<212> TYPE: DNA
<213> ORGANISM: Artificial Sequence
<220> FEATURE:
<223> OTHER INFORMATION: NATJK-R1

<400> SEQUENCE: 120
gaggagagat cttttgatc tctaccttgg t          31

<210> SEQ ID NO 121
<211> LENGTH: 31
<212> TYPE: DNA
<213> ORGANISM: Artificial Sequence
<220> FEATURE:
<223> OTHER INFORMATION: NATJK-R2

<400> SEQUENCE: 121
gaggagagat cttttgatc tccactttgg t          31

<210> SEQ ID NO 122
<211> LENGTH: 34
<212> TYPE: DNA
<213> ORGANISM: Artificial Sequence
<220> FEATURE:
<223> OTHER INFORMATION: NATJL1-R

<400> SEQUENCE: 122
gaggagagat ctttaggacg gtgaccttgg tccc          34

<210> SEQ ID NO 123
<211> LENGTH: 31
<212> TYPE: DNA
<213> ORGANISM: Artificial Sequence
<220> FEATURE:
<223> OTHER INFORMATION: NATJK-R5

<400> SEQUENCE: 123
gaggagagat cttttgatt tccagcttgg t          31

<210> SEQ ID NO 124
<211> LENGTH: 34
<212> TYPE: DNA
<213> ORGANISM: Artificial Sequence

```
<220> FEATURE:
<223> OTHER INFORMATION: NATJL2-R

<400> SEQUENCE: 124
gaggagagat ctttaggacg gtcagcttgg tccc                              34

<210> SEQ ID NO 125
<211> LENGTH: 23
<212> TYPE: DNA
<213> ORGANISM: Artificial Sequence
<220> FEATURE:
<223> OTHER INFORMATION: pelB5primer

<400> SEQUENCE: 125
ctagataacg agggcaaatc atg                                          23

<210> SEQ ID NO 126
<211> LENGTH: 19
<212> TYPE: DNA
<213> ORGANISM: Artificial Sequence
<220> FEATURE:
<223> OTHER INFORMATION: cla3primer

<400> SEQUENCE: 126
cgtcaccaat gaaaccatc                                               19

<210> SEQ ID NO 127
<211> LENGTH: 18
<212> TYPE: DNA
<213> ORGANISM: Artificial Sequence
<220> FEATURE:
<223> OTHER INFORMATION: CMV-proFprimer

<400> SEQUENCE: 127
aaatgggcgg taggcgtg                                                18

<210> SEQ ID NO 128
<211> LENGTH: 50
<212> TYPE: DNA
<213> ORGANISM: Artificial Sequence
<220> FEATURE:
<223> OTHER INFORMATION: NATVH7-3

<400> SEQUENCE: 128
ttggtggcca cagcggccga tgtccactcg caggtgcagc tggtaaagtc             50

<210> SEQ ID NO 129
<211> LENGTH: 30
<212> TYPE: DNA
<213> ORGANISM: Artificial Sequence
<220> FEATURE:
<223> OTHER INFORMATION: NATJK-R3

<400> SEQUENCE: 129
gaggagagat cttttgatct ccagtcgtgt                                   30

<210> SEQ ID NO 130
<211> LENGTH: 14
<212> TYPE: PRT
<213> ORGANISM: Artificial Sequence
<220> FEATURE:
<223> OTHER INFORMATION: 2B05 LC-CDR1

<400> SEQUENCE: 130

Thr Gly Gly Asp Ser Asn Ile Gly Ala Gly Tyr Asp Val Asn
 1               5                  10
```

<210> SEQ ID NO 131
<211> LENGTH: 16
<212> TYPE: PRT
<213> ORGANISM: Artificial Sequence
<220> FEATURE:
<223> OTHER INFORMATION: 2C11 LC-CDR1

<400> SEQUENCE: 131

Arg Ser Ser Gln Ser Leu Val Arg Ser Asp Gly Thr Thr Tyr Leu Ser
1               5                   10                  15

<210> SEQ ID NO 132
<211> LENGTH: 14
<212> TYPE: PRT
<213> ORGANISM: Artificial Sequence
<220> FEATURE:
<223> OTHER INFORMATION: 2D10 LC-CDR1

<400> SEQUENCE: 132

Thr Gly Ser Ser Ser Asn Leu Gly Ala Pro Asn Asp Val His
1               5                   10

<210> SEQ ID NO 133
<211> LENGTH: 14
<212> TYPE: PRT
<213> ORGANISM: Artificial Sequence
<220> FEATURE:
<223> OTHER INFORMATION: 2F01 LC-CDR1

<400> SEQUENCE: 133

Thr Gly Ser Ser Ser Asn Ile Gly Ala Pro Asn Asp Val His
1               5                   10

<210> SEQ ID NO 134
<211> LENGTH: 16
<212> TYPE: PRT
<213> ORGANISM: Artificial Sequence
<220> FEATURE:
<223> OTHER INFORMATION: 2G03 LC-CDR1

<400> SEQUENCE: 134

Arg Ser Ser Gln Ser Leu Val Arg Ser Asp Gly Thr Thr Tyr Leu Ser
1               5                   10                  15

<210> SEQ ID NO 135
<211> LENGTH: 14
<212> TYPE: PRT
<213> ORGANISM: Artificial Sequence
<220> FEATURE:
<223> OTHER INFORMATION: 2G04 LC-CDR1

<400> SEQUENCE: 135

Thr Gly Ser Arg Ser Asn Phe Gly Ala Gly His Asp Val His
1               5                   10

<210> SEQ ID NO 136
<211> LENGTH: 14
<212> TYPE: PRT
<213> ORGANISM: Artificial Sequence
<220> FEATURE:
<223> OTHER INFORMATION: 2G12 LC-CDR1

<400> SEQUENCE: 136

Thr Gly Ser Ser Ser Asn Ile Gly Ala Gly Ser Asp Val His
1               5                   10

<210> SEQ ID NO 137

```
<211> LENGTH: 14
<212> TYPE: PRT
<213> ORGANISM: Artificial Sequence
<220> FEATURE:
<223> OTHER INFORMATION: 2H07 LC-CDR1

<400> SEQUENCE: 137

Thr Gly Ser Ser Thr Asn Ile Gly Ala Gly Tyr Asp Val His
1               5                   10

<210> SEQ ID NO 138
<211> LENGTH: 14
<212> TYPE: PRT
<213> ORGANISM: Artificial Sequence
<220> FEATURE:
<223> OTHER INFORMATION: 2H08 LC-CDR1

<400> SEQUENCE: 138

Ser Glu Ser Ser Ser Asn Ile Gly Ala Gly Phe Asp Val His
1               5                   10

<210> SEQ ID NO 139
<211> LENGTH: 11
<212> TYPE: PRT
<213> ORGANISM: Artificial Sequence
<220> FEATURE:
<223> OTHER INFORMATION: 2H09 LC-CDR1

<400> SEQUENCE: 139

Arg Ala Ser Gln Gly Ile Val Ser Trp Leu Ala
1               5                   10

<210> SEQ ID NO 140
<211> LENGTH: 14
<212> TYPE: PRT
<213> ORGANISM: Artificial Sequence
<220> FEATURE:
<223> OTHER INFORMATION: 2C05 LC-CDR1

<400> SEQUENCE: 140

Gly Ser Ser Ala Gly Ala Val Thr Ser Gly His Tyr Pro Phe
1               5                   10

<210> SEQ ID NO 141
<211> LENGTH: 14
<212> TYPE: PRT
<213> ORGANISM: Artificial Sequence
<220> FEATURE:
<223> OTHER INFORMATION: 2F09 LC-CDR1

<400> SEQUENCE: 141

Thr Gly Ser Ser Ser Asn Leu Gly Ala Gly Tyr Asp Val His
1               5                   10

<210> SEQ ID NO 142
<211> LENGTH: 11
<212> TYPE: PRT
<213> ORGANISM: Artificial Sequence
<220> FEATURE:
<223> OTHER INFORMATION: 1F10 LC-CDR1

<400> SEQUENCE: 142

Arg Ala Ser Gln Pro Ile Ser Asn Trp Leu Ala
1               5                   10

<210> SEQ ID NO 143
<211> LENGTH: 7
<212> TYPE: PRT
```

```
<213> ORGANISM: Artificial Sequence
<220> FEATURE:
<223> OTHER INFORMATION: 2A09 & 2H07 LC-CDR2

<400> SEQUENCE: 143

Gly Asn Ser Asn Arg Pro Ser
1               5

<210> SEQ ID NO 144
<211> LENGTH: 7
<212> TYPE: PRT
<213> ORGANISM: Artificial Sequence
<220> FEATURE:
<223> OTHER INFORMATION: 2B05 & 2G03 LC-CDR2

<400> SEQUENCE: 144

Gly Asp Thr Phe Arg Pro Ser
1               5

<210> SEQ ID NO 145
<211> LENGTH: 7
<212> TYPE: PRT
<213> ORGANISM: Artificial Sequence
<220> FEATURE:
<223> OTHER INFORMATION: 2C11 LC-CDR2

<400> SEQUENCE: 145

Lys Ile Ser Asn Arg Phe Ser
1               5

<210> SEQ ID NO 146
<211> LENGTH: 7
<212> TYPE: PRT
<213> ORGANISM: Artificial Sequence
<220> FEATURE:
<223> OTHER INFORMATION: 2D10 LC-CDR2

<400> SEQUENCE: 146

Gly Ser Thr Asn Arg Pro Ser
1               5

<210> SEQ ID NO 147
<211> LENGTH: 7
<212> TYPE: PRT
<213> ORGANISM: Artificial Sequence
<220> FEATURE:
<223> OTHER INFORMATION: 2F01 LC-CDR2

<400> SEQUENCE: 147

Gly Asn Thr Asn Arg Pro Ser
1               5

<210> SEQ ID NO 148
<211> LENGTH: 7
<212> TYPE: PRT
<213> ORGANISM: Artificial Sequence
<220> FEATURE:
<223> OTHER INFORMATION: 2H08 LC-CDR2

<400> SEQUENCE: 148

Gly Asn Thr Asp Arg Pro Ser
1               5

<210> SEQ ID NO 149
<211> LENGTH: 7
<212> TYPE: PRT
<213> ORGANISM: Artificial Sequence
<220> FEATURE:
```

<223> OTHER INFORMATION: 2H09 LC-CDR2

<400> SEQUENCE: 149

Ala Ala Ser Glu Leu Gln Ser
1               5

<210> SEQ ID NO 150
<211> LENGTH: 7
<212> TYPE: PRT
<213> ORGANISM: Artificial Sequence
<220> FEATURE:
<223> OTHER INFORMATION: 2C05 LC-CDR2

<400> SEQUENCE: 150

Asp Thr Ser Asn Arg His Phe
1               5

<210> SEQ ID NO 151
<211> LENGTH: 7
<212> TYPE: PRT
<213> ORGANISM: Artificial Sequence
<220> FEATURE:
<223> OTHER INFORMATION: 2F09 LC-CDR2

<400> SEQUENCE: 151

Gly Asp Val Asn Arg Pro Ser
1               5

<210> SEQ ID NO 152
<211> LENGTH: 7
<212> TYPE: PRT
<213> ORGANISM: Artificial Sequence
<220> FEATURE:
<223> OTHER INFORMATION: 1F10 LC-CDR2

<400> SEQUENCE: 152

Ala Thr Ser Ile Leu Gln Ser
1               5

<210> SEQ ID NO 153
<211> LENGTH: 10
<212> TYPE: PRT
<213> ORGANISM: Artificial Sequence
<220> FEATURE:
<223> OTHER INFORMATION: 2A09 & 2D10 LC-CDR3

<400> SEQUENCE: 153

Gln Ser Tyr Asp Asn Ser Leu Ser Ala Tyr
1               5                   10

<210> SEQ ID NO 154
<211> LENGTH: 10
<212> TYPE: PRT
<213> ORGANISM: Artificial Sequence
<220> FEATURE:
<223> OTHER INFORMATION: 2B05 & 2G12 LC-CDR3

<400> SEQUENCE: 154

Gln Ser Tyr Asp Ser Ser Leu Ser Gly Tyr
1               5                   10

<210> SEQ ID NO 155
<211> LENGTH: 9
<212> TYPE: PRT
<213> ORGANISM: Artificial Sequence
<220> FEATURE:
<223> OTHER INFORMATION: 2C11 & 2G03 LC-CDR3

```
<400> SEQUENCE: 155

Met Gln Ala Thr Phe Phe Pro Phe Thr
1               5

<210> SEQ ID NO 156
<211> LENGTH: 11
<212> TYPE: PRT
<213> ORGANISM: Artificial Sequence
<220> FEATURE:
<223> OTHER INFORMATION: 2E11 LC-CDR3

<400> SEQUENCE: 156

Gln Ser Asn Asp Pro Ser Leu Gly Gly Leu His
1               5                   10

<210> SEQ ID NO 157
<211> LENGTH: 11
<212> TYPE: PRT
<213> ORGANISM: Artificial Sequence
<220> FEATURE:
<223> OTHER INFORMATION: 2F01 LC-CDR3

<400> SEQUENCE: 157

Gln Ser Tyr Asp Asn Gly Leu Ser Ala Ser Tyr
1               5                   10

<210> SEQ ID NO 158
<211> LENGTH: 10
<212> TYPE: PRT
<213> ORGANISM: Artificial Sequence
<220> FEATURE:
<223> OTHER INFORMATION: 2G04 LC-CDR3

<400> SEQUENCE: 158

Gln Ser Phe Asp Asn Thr Leu Asn Gly Trp
1               5                   10

<210> SEQ ID NO 159
<211> LENGTH: 12
<212> TYPE: PRT
<213> ORGANISM: Artificial Sequence
<220> FEATURE:
<223> OTHER INFORMATION: 2H07 LC-CDR3

<400> SEQUENCE: 159

Gln Ser Tyr Asp Ser Ser Leu Ser Gly Ser Leu Tyr
1               5                   10

<210> SEQ ID NO 160
<211> LENGTH: 10
<212> TYPE: PRT
<213> ORGANISM: Artificial Sequence
<220> FEATURE:
<223> OTHER INFORMATION: 2H08 LC-CDR3

<400> SEQUENCE: 160

Gln Ser Tyr Asp Ser Ser Leu Arg Ala Tyr
1               5                   10

<210> SEQ ID NO 161
<211> LENGTH: 9
<212> TYPE: PRT
<213> ORGANISM: Artificial Sequence
<220> FEATURE:
<223> OTHER INFORMATION: 2H09 LC-CDR3

<400> SEQUENCE: 161
```

```
Gln Gln Leu Asn Asn Phe Leu Phe Ala
1               5

<210> SEQ ID NO 162
<211> LENGTH: 8
<212> TYPE: PRT
<213> ORGANISM: Artificial Sequence
<220> FEATURE:
<223> OTHER INFORMATION: 2C05 LC-CDR3

<400> SEQUENCE: 162

Phe Val Ala Tyr Gly Ala Ile Trp
1               5

<210> SEQ ID NO 163
<211> LENGTH: 10
<212> TYPE: PRT
<213> ORGANISM: Artificial Sequence
<220> FEATURE:
<223> OTHER INFORMATION: 2F09 LC-CDR3

<400> SEQUENCE: 163

Gln Ser Tyr Asp Thr Ser Leu Val Gly Ser
1               5                   10

<210> SEQ ID NO 164
<211> LENGTH: 8
<212> TYPE: PRT
<213> ORGANISM: Artificial Sequence
<220> FEATURE:
<223> OTHER INFORMATION: 1F10 LC-CDR3

<400> SEQUENCE: 164

Gln Gln His Arg Asp Tyr Pro Leu
1               5

<210> SEQ ID NO 165
<211> LENGTH: 31
<212> TYPE: PRT
<213> ORGANISM: Artificial Sequence
<220> FEATURE:
<223> OTHER INFORMATION: VEGF LC shuffling 2A09 light chain

<400> SEQUENCE: 165

Thr Gly Ser Ser Ser Asn Ile Gly Ala Gly Tyr Asp Val His Gly Asn
1               5                   10                  15

Ser Asn Arg Pro Ser Gln Ser Tyr Asp Asn Ser Leu Ser Ala Tyr
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: VEGF LC shuffling 2B05 light chain

<400> SEQUENCE: 166

Thr Gly Gly Asp Ser Asn Ile Gly Ala Gly Tyr Asp Val Asn Gly Asp
1               5                   10                  15

Thr Phe Arg Pro Ser Gln Ser Tyr Asp Ser Ser Leu Ser Gly Tyr
            20                  25                  30

<210> SEQ ID NO 167
<211> LENGTH: 32
<212> TYPE: PRT
<213> ORGANISM: Artificial Sequence
<220> FEATURE:
```

<223> OTHER INFORMATION: VEGF LC shuffling 2C11 & 2G03 light chain

<400> SEQUENCE: 167

Arg Ser Ser Gln Ser Leu Val Arg Ser Asp Gly Thr Thr Tyr Leu Ser
1               5                   10                  15

Lys Ile Ser Asn Arg Phe Ser Met Gln Ala Thr Phe Phe Pro Phe Thr
            20                  25                  30

<210> SEQ ID NO 168
<211> LENGTH: 31
<212> TYPE: PRT
<213> ORGANISM: Artificial Sequence
<220> FEATURE:
<223> OTHER INFORMATION: VEGF LC shuffling 2D10 light chain

<400> SEQUENCE: 168

Thr Gly Ser Ser Ser Asn Leu Gly Ala Pro Asn Asp Val His Gly Ser
1               5                   10                  15

Thr Asn Arg Pro Ser Gln Ser Tyr Asp Asn Ser Leu Ser Ala Tyr
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: VEGF LC shuffling 2E11 light chain

<400> SEQUENCE: 169

Thr Gly Ser Ser Ser Asn Ile Gly Ala Gly Tyr Asp Val His Gly Asn
1               5                   10                  15

Asn Asn Arg Pro Ser Gln Ser Asn Asp Pro Ser Leu Gly Gly Leu His
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: VEGF LC shuffling 2F01 light chain

<400> SEQUENCE: 170

Thr Gly Ser Ser Ser Asn Ile Gly Ala Pro Asn Asp Val His Gly Asn
1               5                   10                  15

Thr Asn Arg Pro Ser Gln Ser Tyr Asp Asn Gly Leu Ser Ala Ser Tyr
            20                  25                  30

<210> SEQ ID NO 171
<211> LENGTH: 31
<212> TYPE: PRT
<213> ORGANISM: Artificial Sequence
<220> FEATURE:
<223> OTHER INFORMATION: VEGF LC shuffling 2G04 light chain

<400> SEQUENCE: 171

Thr Gly Ser Arg Ser Asn Phe Gly Ala Gly His Asp Val His Gly Asn
1               5                   10                  15

Asn Asn Arg Pro Ser Gln Ser Phe Asp Asn Thr Leu Asn Gly Trp
            20                  25                  30

<210> SEQ ID NO 172
<211> LENGTH: 31
<212> TYPE: PRT
<213> ORGANISM: Artificial Sequence
<220> FEATURE:

<223> OTHER INFORMATION: VEGF LC shuffling 2G12 light chain

<400> SEQUENCE: 172

Thr Gly Ser Ser Ser Asn Ile Gly Ala Gly Ser Asp Val His Gly Asn
1               5                   10                  15

Asn Asn Arg Pro Ser Gln Ser Tyr Asp Ser Ser Leu Ser Gly Tyr
            20                  25                  30

<210> SEQ ID NO 173
<211> LENGTH: 33
<212> TYPE: PRT
<213> ORGANISM: Artificial Sequence
<220> FEATURE:
<223> OTHER INFORMATION: VEGF LC shuffling 2H07 light chain

<400> SEQUENCE: 173

Thr Gly Ser Ser Thr Asn Ile Gly Ala Gly Tyr Asp Val His Gly Asn
1               5                   10                  15

Ser Asn Arg Pro Ser Gln Ser Tyr Asp Ser Ser Leu Ser Gly Ser Leu
            20                  25                  30

Tyr

<210> SEQ ID NO 174
<211> LENGTH: 31
<212> TYPE: PRT
<213> ORGANISM: Artificial Sequence
<220> FEATURE:
<223> OTHER INFORMATION: VEGF LC shuffling 2H08 light chain

<400> SEQUENCE: 174

```
Ser Glu Ser Ser Ser Asn Ile Gly Ala Gly Phe Asp Val His Gly Asn
1               5                   10                  15

Thr Asp Arg Pro Ser Gln Ser Tyr Asp Ser Ser Leu Arg Ala Tyr
            20                  25                  30
```

<210> SEQ ID NO 175
<211> LENGTH: 27
<212> TYPE: PRT
<213> ORGANISM: Artificial Sequence
<220> FEATURE:
<223> OTHER INFORMATION: VEGF LC shuffling 2H09 light chain

<400> SEQUENCE: 175

```
Arg Ala Ser Gln Gly Ile Val Ser Trp Leu Ala Ala Ala Ser Glu Leu
1               5                   10                  15

Gln Ser Gln Gln Leu Asn Asn Phe Leu Phe Ala
            20                  25
```

<210> SEQ ID NO 176
<211> LENGTH: 29
<212> TYPE: PRT
<213> ORGANISM: Artificial Sequence
<220> FEATURE:
<223> OTHER INFORMATION: VEGF LC shuffling 2C05 light chain

<400> SEQUENCE: 176

```
Gly Ser Ser Ala Gly Ala Val Thr Ser Gly His Tyr Pro Phe Asp Thr
1               5                   10                  15

Ser Asn Arg His Phe Phe Val Ala Tyr Gly Ala Ile Trp
            20                  25
```

<210> SEQ ID NO 177
<211> LENGTH: 31
<212> TYPE: PRT

<213> ORGANISM: Artificial Sequence
<220> FEATURE:
<223> OTHER INFORMATION: VEGF LC shuffling 2F09 light chain

<400> SEQUENCE: 177

Thr Gly Ser Ser Ser Asn Leu Gly Ala Gly Tyr Asp Val His Gly Asp
1               5                   10                  15

Val Asn Arg Pro Ser Gln Ser Tyr Asp Thr Ser Leu Val Gly Ser
            20                  25                  30

<210> SEQ ID NO 178
<211> LENGTH: 26
<212> TYPE: PRT
<213> ORGANISM: Artificial Sequence
<220> FEATURE:
<223> OTHER INFORMATION: VEGF LC shuffling 1F10 light chain

<400> SEQUENCE: 178

Arg Ala Ser Gln Pro Ile Ser Asn Trp Leu Ala Ala Thr Ser Ile Leu
1               5                   10                  15

Gln Ser Gln Gln His Arg Asp Tyr Pro Leu
            20                  25

<210> SEQ ID NO 179
<211> LENGTH: 50
<212> TYPE: DNA
<213> ORGANISM: Artificial Sequence
<220> FEATURE:
<223> OTHER INFORMATION: NATVH2-3

<400> SEQUENCE: 179
ttggtggcca cagcggccga tgtccactcg caggtcacct tgagggagtc          50

<210> SEQ ID NO 180
<211> LENGTH: 50
<212> TYPE: DNA
<213> ORGANISM: Artificial Sequence
<220> FEATURE:
<223> OTHER INFORMATION: NATVL13

<400> SEQUENCE: 180
ttggtggcca cagcggccga tgtccactcg cagttcgtgc tgactcagcc          50

<210> SEQ ID NO 181
<211> LENGTH: 53
<212> TYPE: DNA
<213> ORGANISM: Artificial Sequence
<220> FEATURE:
<223> OTHER INFORMATION: NATVK3

<400> SEQUENCE: 181
ttggtggcca cagcggccga tgtccactcg gatattgtga tgacccagac tcc      53

<210> SEQ ID NO 182
<211> LENGTH: 50
<212> TYPE: DNA
<213> ORGANISM: Artificial Sequence
<220> FEATURE:
<223> OTHER INFORMATION: NATVL13

<400> SEQUENCE: 182
ttggtggcca cagcggccga tgtccactcg cagttcgtgc tgactcagcc          50

<210> SEQ ID NO 183
<211> LENGTH: 50
<212> TYPE: DNA

```
<213> ORGANISM: Artificial Sequence
<220> FEATURE:
<223> OTHER INFORMATION: NATVK1-1

<400> SEQUENCE: 183
ttggtggcca cagcggccga tgtccactcg gacatccaga tgacccagtc        50

<210> SEQ ID NO 184
<211> LENGTH: 50
<212> TYPE: DNA
<213> ORGANISM: Artificial Sequence
<220> FEATURE:
<223> OTHER INFORMATION: NATVL12

<400> SEQUENCE: 184
ttggtggcca cagcggccga tgtccactcg caggctgtgg tgactcagga        50

<210> SEQ ID NO 185
<211> LENGTH: 50
<212> TYPE: DNA
<213> ORGANISM: Artificial Sequence
<220> FEATURE:
<223> OTHER INFORMATION: NATVL13

<400> SEQUENCE: 185
ttggtggcca cagcggccga tgtccactcg cagttcgtgc tgactcagcc        50

<210> SEQ ID NO 186
<211> LENGTH: 33
<212> TYPE: DNA
<213> ORGANISM: Artificial Sequence
<220> FEATURE:
<223> OTHER INFORMATION: NATJL1-R

<400> SEQUENCE: 186
gaggagagat cttaggacgg tgaccttggt ccc        33

<210> SEQ ID NO 187
<211> LENGTH: 30
<212> TYPE: DNA
<213> ORGANISM: Artificial Sequence
<220> FEATURE:
<223> OTHER INFORMATION: NATJK-R2

<400> SEQUENCE: 187
gaggagagat cttttgatct ccactttggt        30

<210> SEQ ID NO 188
<211> LENGTH: 33
<212> TYPE: DNA
<213> ORGANISM: Artificial Sequence
<220> FEATURE:
<223> OTHER INFORMATION: NATJL1-R

<400> SEQUENCE: 188
gaggagagat cttaggacgg tgaccttggt ccc        33

<210> SEQ ID NO 189
<211> LENGTH: 33
<212> TYPE: DNA
<213> ORGANISM: Artificial Sequence
<220> FEATURE:
<223> OTHER INFORMATION: NATJL1-R

<400> SEQUENCE: 189
gaggagagat cttaggacgg tgaccttggt ccc        33
```

```
<210> SEQ ID NO 190
<211> LENGTH: 30
<212> TYPE: DNA
<213> ORGANISM: Artificial Sequence
<220> FEATURE:
<223> OTHER INFORMATION: NATJK-R2

<400> SEQUENCE: 190
gaggagagat cttttgatct ccactttggt                                          30

<210> SEQ ID NO 191
<211> LENGTH: 30
<212> TYPE: DNA
<213> ORGANISM: Artificial Sequence
<220> FEATURE:
<223> OTHER INFORMATION: NATJL5-R

<400> SEQUENCE: 191
gaggagagat cttaggacgg tcagctcggt                                          30
```